(12) United States Patent
Schaus et al.

(10) Patent No.: US 9,796,748 B2
(45) Date of Patent: Oct. 24, 2017

(54) SPATIAL SEQUESTRATION OF DYNAMIC NUCLEIC ACID CIRCUITS

(75) Inventors: Thomas E. Schaus, Brookline, MA (US); David Yu Zhang, Houston, TX (US); Wei Sun, Brookline, MA (US); Peng Yin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 14 days.

(21) Appl. No.: 14/114,961

(22) PCT Filed: May 2, 2012

(86) PCT No.: PCT/US2012/036193
§ 371 (c)(1),
(2), (4) Date: Oct. 31, 2013

(87) PCT Pub. No.: WO2012/151328
PCT Pub. Date: Nov. 8, 2012

(65) Prior Publication Data
US 2014/0066610 A1    Mar. 6, 2014

Related U.S. Application Data

(60) Provisional application No. 61/481,542, filed on May 2, 2011.

(51) Int. Cl.
*C12Q 1/68*         (2006.01)
*C12N 15/11*        (2006.01)
*B82Y 15/00*        (2011.01)
*C07H 21/04*        (2006.01)
*B82Y 5/00*         (2011.01)

(52) U.S. Cl.
CPC ......... *C07H 21/04* (2013.01); *C12Q 1/6816* (2013.01); *B82Y 5/00* (2013.01); *B82Y 15/00* (2013.01); *Y10S 977/795* (2013.01)

(58) Field of Classification Search
None
See application file for complete search history.

(56) References Cited

U.S. PATENT DOCUMENTS

| | | | |
|---|---|---|---|
| 5,436,149 A | 7/1995 | Barnes | |
| 6,033,851 A | 3/2000 | Yamane | |
| 6,958,216 B2* | 10/2005 | Kelley et al. | 506/39 |
| 7,745,594 B2 | 6/2010 | Seelig et al. | |
| 7,799,522 B2 | 9/2010 | Li et al. | |
| 7,842,793 B2 | 11/2010 | Rothemund | |
| 9,284,602 B2 | 3/2016 | Zhang et al. | |
| 2002/0127575 A1 | 9/2002 | Hoke et al. | |
| 2007/0072215 A1 | 3/2007 | Seelig et al. | |
| 2007/0117109 A1* | 5/2007 | Rothemund | 435/6 |
| 2009/0011956 A1 | 1/2009 | Yin et al. | |
| 2009/0087838 A1 | 4/2009 | Reif et al. | |
| 2009/0191546 A1 | 7/2009 | Zhang et al. | |
| 2010/0069621 A1 | 3/2010 | Maune et al. | |
| 2010/0203532 A1 | 8/2010 | Makrigiorgos | |
| 2013/0224859 A1* | 8/2013 | Bachelet | C12Q 1/68 435/375 |
| 2013/0261019 A1 | 10/2013 | Lin et al. | |
| 2013/0274135 A1 | 10/2013 | Zhang et al. | |
| 2014/0213778 A1 | 7/2014 | Yin et al. | |
| 2014/0220655 A1 | 8/2014 | Sun et al. | |
| 2014/0303320 A1 | 10/2014 | Schaus et al. | |
| 2015/0152491 A1 | 6/2015 | Zhang et al. | |
| 2016/0153036 A1 | 6/2016 | Chen et al. | |

FOREIGN PATENT DOCUMENTS

| | | | |
|---|---|---|---|
| WO | WO 03/095664 A2 | 11/2003 | |
| WO | WO 2007/047572 A2 | 4/2007 | |
| WO | WO 2007/106534 A2 | 9/2007 | |
| WO | WO2008/097929 * | 8/2008 | C12Q 1/68 |
| WO | WO 2008/104794 A2 | 9/2008 | |
| WO | WO 2009/019008 A1 | 2/2009 | |
| WO | WO 2010/048002 A1 | 4/2010 | |
| WO | WO 2010/065626 A1 | 6/2010 | |
| WO | WO 2010/148085 * | 12/2010 | A61K 47/48 |
| WO | WO 2011/112534 A1 | 9/2011 | |
| WO | WO 2012/058488 A1 | 5/2012 | |
| WO | WO 2014/018675 A1 | 1/2014 | |
| WO | WO 2014/074597 A1 | 5/2014 | |
| WO | WO 2014/074648 A2 | 5/2014 | |
| WO | WO 2014/078636 A1 | 5/2014 | |

OTHER PUBLICATIONS

Yin et al., Programming biomolecular self-assembly pathways. Nature, vol. 451, p. 318-323, Jan. 2008.*
Andersen et al., Self-assembly of a nanoscale DNA box with a controllable lid. Nature. May 7, 2009;459(7243):73-6. doi: 10.1038/nature07971.
Zhang et al., Dynamic DNA nanotechnology using strand-displacement reactions. Nat Chem. Feb. 2011;3(2):103-13. doi: 10.1038/nchem.957.
Zhang et al., Optimizing the specificity of nucleic acid hybridization. Nat Chem. Jan. 22, 2012;4(3):208-14. doi: 10.1038/nchem.1246.
Amicarelli et al., FLAG assay as a novel method for real-time signal generation during PCR: application to detection and genotyping of KRAS codon 12 mutations. Nucleic Acids Res. 2007;35(19):e131. Epub Oct. 11, 2007.
Ashford, Precision Nanoscale Car Parts Self-Assembled From DNA. Popular Science. Aug. 6, 2009. Available at http://www.popsci.com/scitech/article/2009-08/nano-origami-goes-3d-and-curvy. 3 pages.
Breslauer et al., Predicting DNA duplex stability from the base sequence. Proc Natl Acad Sci U S A. Jun. 1986;83(11):3746-50.
Cha et al., Mismatch amplification mutation assay (MAMA): application to the c-H-ras gene. PCR Methods Appl. Aug. 1992;2(1):14-20.
Chen et al., Synthesis from DNA of a molecule with the connectivity of a cube. Nature. Apr. 18, 1991;350(6319):631-3.
Cho et al., Applications of aptamers as sensors. Annu Rev Anal Chem (Palo Alto Calif). 2009;2:241-64. doi:10.1146/annurev.anchem.1.031207.112851.

(Continued)

*Primary Examiner* — Christopher M Babic
*Assistant Examiner* — Arthur S Leonard
(74) *Attorney, Agent, or Firm* — Wolf, Greenfield & Sacks, P.C.

(57) ABSTRACT

The invention provides systems and methods for spatial sequestration of elements in nucleic acid circuits.

19 Claims, 15 Drawing Sheets

(56) References Cited

OTHER PUBLICATIONS

Dirks et al., Thermodynamic Analysis of Interacting Nucleic Acid Strands. SIAM Rev. 2007;49(1):65-88.

Dirks et al., Triggered amplification by hybridization chain reaction. PNAS. 2004;101: 15275-78.

Dobosy et al., RNase H-dependent PCR (rhPCR): improved specificity and single nucleotide polymorphism detection using blocked cleavable primers. BMC Biotechnol. Aug. 10, 2011;11:80. doi:10.1186/1472-6750-11-80.

Douglas et al., Rapid prototyping of 3D DNA-origami shapes with caDNAno. Nucleic Acids Res. Aug. 2009;37(15):5001-6. doi: 10.1093/nar/gkp436. Epub Jun. 16, 2009.

Douglas et al., Self-assembly of DNA into nanoscale three-dimensional shapes. Nature. May 21, 2009;459(7245):414-8. Available in PMC Nov. 21, 2009.

Genot et al., Remote Toehold: A Mechanism for Flexible Control of DNA Hybridization Kinetics. J. Am. Chem. Soc. 2011:133(7):2177-82.

Gevensleben et al., Noninvasive detection of HER2 amplification with plasma DNA digital PCR. Clin Cancer Res. Jun. 15, 2013;19(12):3276-84. doi:10.1158/1078-0432.CCR-12-3768. Epub May 1, 2013.

Goodman et al., Reconfigurable, braced, three-dimensional DNA nanostructures. Nat Nanotechnol. Feb. 2008;3(2):93-6. doi: 10.1038/nnano.2008.3. Epub Feb. 3, 2008.

Hall et al., Kinetic optimization of a protein-responsive aptamer beacon. Biotechnol Bioeng. Aug. 15, 2009;103(6):1049-59.

Han et al., Self-assembly with DNA origami. NSF NSE Grantees Conference presentation. Arlington, VA. Dec. 5-7, 2011.

Hotz, Gene Expression: Origami at the Molecular Level. The Wall Street Journal. Jun. 5, 2009. Available at http://www.wsj.com/articles/SB124413997181485425. 6 pages.

Kaboev et al., PCR hot start using primers with the structure of molecular beacons (hairpin-like structure). Nucleic Acids Res. Nov. 1, 2000;28(21):E94.

Krueger et al., Redesigning the architecture of the base pair: toward biochemical and biological function of new genetic sets. Chem Biol. Mar. 27, 2009;16(3):242-8.

Kuzuya et al., Design and construction of a box-shaped 3D-DNA origami. Chem Commun (Camb). Jul. 28, 2009;(28):4182-4. doi: 10.1039/b907800b. Epub Jun. 17, 2009.

Lang et al., Optimized allele-specific real-time PCR assays for the detection of common mutations in KRAS and BRAF. J Mol Diagn. Jan. 2011;13(1):23-8. doi:10.1016/j.jmoldx.2010.11.007. Epub Dec. 23, 2010.

Lebedev et al., Hot start PCR with heat-activatable primers: a novel approach for improved PCR performance. Nucleic Acids Res. Nov. 2008;36(20):e131. Epub Sep. 16, 2008.

Li et al., Genotyping with TaqMAMA. Genomics. Feb. 2004;83(2):311-20.

Li et al., Replacing PCR with COLD-PCR enriches variant DNA sequences and redefines the sensitivity of genetic testing. Nat Med. May 2008;14(5):579-84. doi: 10.1038/nm1708. Epub Apr. 13, 2008.

Liu et al., Pyrophosphorolysis-activated polymerization (PAP):application to allele-specific amplification. Biotechniques. Nov. 2000;29(5):1072-4, 1076, 1078, 1080, 1082-3 passim.

Lizardi et al., Mutation detection and single-molecule counting using isothermal rolling-circle amplification. Nat Genet. Jul. 1998;19(3):225-32.

Mann et al., A thermodynamic approach to PCR primer design. Nucleic Acids Res. Jul. 2009;37(13):e95. Epub Jun. 15, 2009.

McKeen et al., Synthesis of fluorophore and quencher monomers for use in scorpion primers and nucleic acid structural probes. Org Biomol Chem. Jul. 7, 2003;1(13):2267-75.

Milbury et al., Multiplex amplification coupled with COLD-PCR and high resolution melting enables identification of low-abundance mutations in cancer samples with low DNA content. J Mol Diagn. Mar. 2011;13(2):220-32. doi: 10.1016/j.jmoldx.2010.10.008.

Milbury et al., PCR-based methods for the enrichment of minority alleles and mutations. Clin Chem. Apr. 2009;55(4):632-40. doi:10.1373/clinchem.2008.113035. Epub Feb. 6, 2009.

Morandi et al., Allele specific locked nucleic acid quantitative PCR (ASLNAqPCR):an accurate and cost-effective assay to diagnose and quantify KRAS and BRAF mutation. PLoS One. 2012;7(4):e36084. doi: 10.1371/journal.pone.0036084. Epub Apr. 30, 2012.

Morlan et al., Mutation detection by real-time PCR: a simple, robust and highly selective method. PLoS One. 2009;4(2):e4584. doi:10.1371/journal.pone.0004584. Epub Feb. 25, 2009.

Newton et al., Analysis of any point mutation in DNA. The amplification refractory mutation system (ARMS). Nucleic Acids Res. Apr. 11, 1989;17(7):2503-16.

Orum et al., Single base pair mutation analysis by PNA directed PCR clamping. Nucleic Acids Res. Nov. 25, 1993;21(23):5332-6.

Petersen et al., LNA: a versatile tool for therapeutics and genomics. Trends Biotechnol. Feb. 2003;21(2):74-81.

Pinzani et al., BRAFV600E detection in melanoma is highly improved by COLD-PCR. Clin Chim Acta. May 12, 2011;412(11-12):901-5. doi:10.1016/j.cca.2011.01.014. Epub Jan. 22, 2011.

Reif et al., Complexity of Graph Self-assembly in Accretive Systems and Self-destructible Systems. Lecture Notes on Computer Science. 2006;3892:257-74.

Rothemund, Folding DNA to create nanoscale shapes and patterns. Nature. Mar. 16, 2006;440:297-302.

Saiki et al., Primer-directed enzymatic amplification of DNA with a thermostable DNA polymerase. Science. Jan. 29, 1988;239(4839):487-91.

Santalucia Jr et al., The thermodynamics of DNA structural motifs. Annu Rev Biophys Biomol Struct. 2004;33:415-40.

Seeman, An overview of structural DNA nanotechnology. Mol Biotechnol. Nov. 2007;37(3):246-57. Epub Jul. 12, 2007.

Seyama et al., A novel blocker-PCR method for detection of rare mutant alleles in the presence of an excess amount of normal DNA. Nucleic Acids Res. May 25, 1992;20(10):2493-6.

Shih et al., Knitting complex weaves with DNA origami. Current Opinion in Structural Biology. Jun. 2010;20(3):276-82. Author manuscript available in PMC Jun. 1, 2011.

Tulpan et al., Free energy estimation of short DNA duplex hybridizations. BMC Bioinformatics. Feb. 24, 2010;11:105. doi:10.1186/1471-2105-11-105.

Tyagi et al., Molecular beacons: probes that fluoresce upon hybridization. Nat Biotechnol. Mar. 1996;14(3):303-8.

Winfree et al., Design and self-assembly of two-dimensional DNA crystals. Nature. Aug. 6, 1998;394(6693):539-44.

Yin et al., Programming DNA tube circumferences. Science. Aug. 8, 2008;321(5890):824-6.

Zadeh et al., NUPACK: Analysis and design of nucleic acid systems. J Comput Chem. Jan. 15, 2011;32(1):170-3. doi:10.1002/jcc.21596.

Zhang et al., A DNA-Origami chip platform for label-free SNP genotyping using toehold-mediated strand displacement. Small. Sep. 6, 2010;6(17):1854-8.

Zhang et al., Integrating DNA strand-displacement circuitry with DNA tile self-assembly. Nat Commun. 2013;4:1965.

Zhang et al., Control of DNA strand displacement kinetics using toehold exchange. J Am Chem Soc. Dec. 2, 2009;131(47):17303-14.

Zhang et al., Robustness and modularity properties of a non-covalent DNA catalytic reaction. Nucleic Acids Res. Jul. 2010;38(12):4182-97. doi:10.1093/nar/gkq088. Epub Mar. 1, 2010.

Zhang, Cooperative Hybridization of Oligonucleotides. J. Am. Chem. Soc. 2011;133 (4):1077-86.

Zhang, Dynamic DNA Strand Displacement Circuits. Doctoral Thesis, California Institute of Technology. May 2010.

Zhou et al., Enrichment and detection of rare alleles by means of snapback primers and rapid-cycle PCR. Clin Chem. May 2010;56(5):814-22. doi: 10.1373/clinchem.2009.142034. Epub Mar. 18, 2010.

(56) References Cited

OTHER PUBLICATIONS

Zhou et al., Rare allele enrichment and detection by allele-specific PCR, competitive probe blocking, and melting analysis. BioTechniques. May 2011;50(5):311-8.

* cited by examiner

SEQUENCE LISTING

<160> NUMBER OF SEQ ID NOS: 317

<210> SEQ ID NO 1
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 1
gcccacgatt gtatgatggt ca                                              22

<210> SEQ ID NO 2
<211> LENGTH: 27
<212> TYPE: DNA
<213> ORGANISM: Artificial Sequence
<220> FEATURE:
<223> OTHER INFORMATION: Synethetic polynucleotide

<400> SEQUENCE: 2 acggggatg gctcttttga gccagtt                                          27

<210> SEQ ID NO 3
<211> LENGTH: 28
<212> TYPE: DNA
<213> ORGANISM: Artificial Sequence
<220> FEATURE:
<223> OTHER INFORMATION: Synethetic polynucleotide

<400> SEQUENCE: 3
gtcaccagtt ttcaaggtca ggaaccac                                        28

<210> SEQ ID NO 4
<211> LENGTH: 28
<212> TYPE: DNA
<213> ORGANISM: Artificial Sequence
<220> FEATURE:
<223> OTHER INFORMATION: Synethetic polynucleotide

<400> SEQUENCE: 4
tgacggaccg acttccagta gtattcat                                        28

<210> SEQ ID NO 5
<211> LENGTH: 29
<212> TYPE: DNA
<213> ORGANISM: Artificial Sequence
<220> FEATURE:
<223> OTHER INFORMATION: Synethetic polynucleotide

<400> SEQUENCE: 5
atcacctacc gaaagcccta aaacatcgc                                       29

<210> SEQ ID NO 6
<211> LENGTH: 29
<212> TYPE: DNA
<213> ORGANISM: Artificial Sequence
<220> FEATURE:
<223> OTHER INFORMATION: Synethetic polynucleotide

<400> SEQUENCE: 6
cctttatccg gagatggcat ctcatttgg                                       29

<210> SEQ ID NO 7
<211> LENGTH: 30
<212> TYPE: DNA
<213> ORGANISM: Artificial Sequence

```
<220> FEATURE:
<223> OTHER INFORMATION: Synethetic polynucleotide

<400> SEQUENCE: 7
taaccacatt tacagacgct caatcgtctg                                      30

<210> SEQ ID NO 8
<211> LENGTH: 34
<212> TYPE: DNA
<213> ORGANISM: Artificial Sequence
<220> FEATURE:
<223> OTHER INFORMATION: Synethetic polynucleotide

<400> SEQUENCE: 8
aaggcttgaa ctggctcatt agacgttgtt ggga                                 34

<210> SEQ ID NO 9
<211> LENGTH: 34
<212> TYPE: DNA
<213> ORGANISM: Artificial Sequence
<220> FEATURE:
<223> OTHER INFORMATION: Synethetic polynucleotide

<400> SEQUENCE: 9
tcatttcaat tcactacaaa ggtaatcacc aggc                                 34

<210> SEQ ID NO 10
<211> LENGTH: 34
<212> TYPE: DNA
<213> ORGANISM: Artificial Sequence
<220> FEATURE:
<223> OTHER INFORMATION: Synethetic polynucleotide

<400> SEQUENCE: 10
aataaatcaa aatttcatca aattacatgg aaac                                 34

<210> SEQ ID NO 11
<211> LENGTH: 35
<212> TYPE: DNA
<213> ORGANISM: Artificial Sequence
<220> FEATURE:
<223> OTHER INFORMATION: Synethetic polynucleotide

<400> SEQUENCE: 11
gttttgtgcc ccctatggct ttttaccgca gaatg                                35

<210> SEQ ID NO 12
<211> LENGTH: 35
<212> TYPE: DNA
<213> ORGANISM: Artificial Sequence
<220> FEATURE:
<223> OTHER INFORMATION: Synethetic polynucleotide

<400> SEQUENCE: 12
tgaaaataga aggtcaaca gcttcatcta cccaa                                 35

<210> SEQ ID NO 13
<211> LENGTH: 35
<212> TYPE: DNA
<213> ORGANISM: Artificial Sequence
<220> FEATURE:
<223> OTHER INFORMATION: Synethetic polynucleotide

<400> SEQUENCE: 13
ttagtaagtg cccggtgtac tggtaatacg gaaac                                35
```

<210> SEQ ID NO 14
<211> LENGTH: 35
<212> TYPE: DNA
<213> ORGANISM: Artificial Sequence
<220> FEATURE:
<223> OTHER INFORMATION: Synethetic polynucleotide

<400> SEQUENCE: 14
tggtgctggt cgtgcagcct agggtaattc ggttg                               35

<210> SEQ ID NO 15
<211> LENGTH: 35
<212> TYPE: DNA
<213> ORGANISM: Artificial Sequence
<220> FEATURE:
<223> OTHER INFORMATION: Synethetic polynucleotide

<400> SEQUENCE: 15
aatacataca taatacccaa agaaaagatt aagcc                               35

<210> SEQ ID NO 16
<211> LENGTH: 35
<212> TYPE: DNA
<213> ORGANISM: Artificial Sequence
<220> FEATURE:
<223> OTHER INFORMATION: Synethetic polynucleotide

<400> SEQUENCE: 16
agtacattca ttccgtagat ttagtttgag gagcg                               35

<210> SEQ ID NO 17
<211> LENGTH: 35
<212> TYPE: DNA
<213> ORGANISM: Artificial Sequence
<220> FEATURE:
<223> OTHER INFORMATION: Synethetic polynucleotide

<400> SEQUENCE: 17
gggcttaatt gaaagttcag tcaaaaaaaa gttaa                               35

<210> SEQ ID NO 18
<211> LENGTH: 35
<212> TYPE: DNA
<213> ORGANISM: Artificial Sequence
<220> FEATURE:
<223> OTHER INFORMATION: Synethetic polynucleotide

<400> SEQUENCE: 18
cggtatgagc cgggcgtcgg taccgcaaaa aagga                               35

<210> SEQ ID NO 19
<211> LENGTH: 35
<212> TYPE: DNA
<213> ORGANISM: Artificial Sequence
<220> FEATURE:
<223> OTHER INFORMATION: Synethetic polynucleotide

<400> SEQUENCE: 19
ccagagccta attttaagag gactttttca aatat                               35

<210> SEQ ID NO 20
<211> LENGTH: 35
<212> TYPE: DNA
<213> ORGANISM: Artificial Sequence
<220> FEATURE:
<223> OTHER INFORMATION: Synethetic polynucleotide

```
<400> SEQUENCE: 20
gtgctgtccc agtctttcag tgaggatcca gcacg                              35

<210> SEQ ID NO 21
<211> LENGTH: 35
<212> TYPE: DNA
<213> ORGANISM: Artificial Sequence
<220> FEATURE:
<223> OTHER INFORMATION: Synethetic polynucleotide

<400> SEQUENCE: 21
gtaagaatta gtctttaatg aagggaagca gacga                              35

<210> SEQ ID NO 22
<211> LENGTH: 35
<212> TYPE: DNA
<213> ORGANISM: Artificial Sequence
<220> FEATURE:
<223> OTHER INFORMATION: Synethetic polynucleotide

<400> SEQUENCE: 22
cagagatata ataaacctgc agacgtataa cgtgc                              35

<210> SEQ ID NO 23
<211> LENGTH: 35
<212> TYPE: DNA
<213> ORGANISM: Artificial Sequence
<220> FEATURE:
<223> OTHER INFORMATION: Synethetic polynucleotide

<400> SEQUENCE: 23
gtcaatactc gtatcatgga gcaaacaaca ttcag                              35

<210> SEQ ID NO 24
<211> LENGTH: 35
<212> TYPE: DNA
<213> ORGANISM: Artificial Sequence
<220> FEATURE:
<223> OTHER INFORMATION: Synethetic polynucleotide

<400> SEQUENCE: 24
caaatcataa attagggtag ctcaatcagc accgc                              35

<210> SEQ ID NO 25
<211> LENGTH: 36
<212> TYPE: DNA
<213> ORGANISM: Artificial Sequence
<220> FEATURE:
<223> OTHER INFORMATION: Synethetic polynucleotide

<400> SEQUENCE: 25
accgttccca agttacaaaa tagtaacaaa attaga                             36

<210> SEQ ID NO 26
<211> LENGTH: 36
<212> TYPE: DNA
<213> ORGANISM: Artificial Sequence
<220> FEATURE:
<223> OTHER INFORMATION: Synethetic polynucleotide

<400> SEQUENCE: 26
attatagcaa aaatttaccg cttaccagaa ccaagt                             36

<210> SEQ ID NO 27
```

<211> LENGTH: 37
<212> TYPE: DNA
<213> ORGANISM: Artificial Sequence
<220> FEATURE:
<223> OTHER INFORMATION: Synethetic polynucleotide

<400> SEQUENCE: 27
ccgtaatgtc atacgcctat tttattcttc aagagaa 37

<210> SEQ ID NO 28
<211> LENGTH: 38
<212> TYPE: DNA
<213> ORGANISM: Artificial Sequence
<220> FEATURE:
<223> OTHER INFORMATION: Synethetic polynucleotide

<400> SEQUENCE: 28
acaggaagtt gatatagcat gtattttta tatttaat 38

<210> SEQ ID NO 29
<211> LENGTH: 39
<212> TYPE: DNA
<213> ORGANISM: Artificial Sequence
<220> FEATURE:
<223> OTHER INFORMATION: Synethetic polynucleotide

<400> SEQUENCE: 29
gctcaacata gttgattttt taatttaaca atttcattt 39

<210> SEQ ID NO 30
<211> LENGTH: 38
<212> TYPE: DNA
<213> ORGANISM: Artificial Sequence
<220> FEATURE:
<223> OTHER INFORMATION: Synethetic polynucleotide

<400> SEQUENCE: 30
agcgtaacga tctaaagaca gccattagga gtttagta 38

<210> SEQ ID NO 31
<211> LENGTH: 39
<212> TYPE: DNA
<213> ORGANISM: Artificial Sequence
<220> FEATURE:
<223> OTHER INFORMATION: Synethetic polynucleotide

<400> SEQUENCE: 31
ctacagaggc tttgagacga gggtgagaat ctccaaaaa 39

<210> SEQ ID NO 32
<211> LENGTH: 41
<212> TYPE: DNA
<213> ORGANISM: Artificial Sequence
<220> FEATURE:
<223> OTHER INFORMATION: Synethetic polynucleotide

<400> SEQUENCE: 32
aaaattgatt caatagtagc ataacctgtt tagcgagaga t 41

<210> SEQ ID NO 33
<211> LENGTH: 41
<212> TYPE: DNA
<213> ORGANISM: Artificial Sequence
<220> FEATURE:
<223> OTHER INFORMATION: Synethetic polynucleotide

<400> SEQUENCE: 33
tgaaacttat acttgcctga gagtcgaacc attacatgtc t     41

<210> SEQ ID NO 34
<211> LENGTH: 41
<212> TYPE: DNA
<213> ORGANISM: Artificial Sequence
<220> FEATURE:
<223> OTHER INFORMATION: Synethetic polynucleotide

<400> SEQUENCE: 34
ttcgcgtgta aacctcagga ttctggtgcc ggaagtaaaa c     41

<210> SEQ ID NO 35
<211> LENGTH: 41
<212> TYPE: DNA
<213> ORGANISM: Artificial Sequence
<220> FEATURE:
<223> OTHER INFORMATION: Synethetic polynucleotide

<400> SEQUENCE: 35
aacagcacct ttacgaacca gaccggatta attcacaaag t     41

<210> SEQ ID NO 36
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 36
attttagatt gctctagagc tacatagctg tgagtgaata ac    42

<210> SEQ ID NO 37
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 37
agaagaactc aaacaacatc acttacggct ggaggttcgc ac    42

<210> SEQ ID NO 38
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 38
caggtcagga ttaatgctgt ttccctctgt aaatcgtcgc ta    42

<210> SEQ ID NO 39
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 39 ccttttcgt cttttaacat aaatagttgc tatttccaac gc    42

<210> SEQ ID NO 40
<211> LENGTH: 42
<212> TYPE: DNA

<213> ORGANISM: Artificial Sequence
<220> FEATURE:
<223> OTHER INFORMATION: Synethetic polynucleotide

<400> SEQUENCE: 40
aggcgcttgt ccagctttga taggtgaagg aaccccaaac ta                              42

<210> SEQ ID NO 41
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 41
aaaagcccat atgcgttata cttttcgatc aagaataat cg                              42

<210> SEQ ID NO 42
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 42
gcctgtgcgg gttaagggac aagttaaacg atgcttcgtc tc                              42

<210> SEQ ID NO 43
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 43
tcctgagaag tgtttttatg gagggattgg cgcgtgcgcg cg                              42

<210> SEQ ID NO 44
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 44
aaagaagttt tgcccggaat aatataaaag aaacgttagc aa                              42

<210> SEQ ID NO 45
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 45 attttttgtta aagtaccgtg cgctgcgcaa ctgttaaacc ac                              42

<210> SEQ ID NO 46
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 46
aaaggttaga ggcaaaattc tttataatta ctagattatt tt                              42

<210> SEQ ID NO 47
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 47
aagagtaatg aacggacttt ttcatgaggc agcgaaaagg aa                              42

<210> SEQ ID NO 48
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 48
atgaaactac aggatataaa cttccactac gaaggcacca tg                              42

<210> SEQ ID NO 49
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 49
taaatatatt caactgagat ttaggaatac ggaacaaatc ta                              42

<210> SEQ ID NO 50
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 50
gctgtcttgt tcaggtccag aaccggaaca aaatcgtttg cc                              42

<210> SEQ ID NO 51
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 51
accacatgac aaaatttgtc attttgcacc agaatcgcca ta                              42

<210> SEQ ID NO 52
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 52
cagagccacg agccgccacc ctcagaacag agccaaaaca aa                              42

<210> SEQ ID NO 53
<211> LENGTH: 42
<212> TYPE: DNA
<213> ORGANISM: Artificial Sequence
<220> FEATURE:

<223> OTHER INFORMATION: Synethetic polynucleotide

<400> SEQUENCE: 53
caccagatac ataaaaatgg tttaccaggg gtcatagccc cc    42

<210> SEQ ID NO 54
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 54
cctcattaaa gcttccagtt tataccaaca ctcatctttg ac    42

<210> SEQ ID NO 55
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 55
ctcatcgaga acaattatca tgccagtaat aaagtaccga ca    42

<210> SEQ ID NO 56
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 56
gaaagcggcc ttgatcagac tcatcttttc ataatccgcc tc    42

<210> SEQ ID NO 57
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 57
ctcatttaac cgccccaccc tcagaacctc aggagttagc gg    42

<210> SEQ ID NO 58
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 58
gggcttgaga tggtgtacaa cagaggcaaa agaatgaaag ta    42

<210> SEQ ID NO 59
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 59
tagcagcctt tacaagacgg gcttctgaca aagcggattg ca    42

<210> SEQ ID NO 60
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 60
catattagtt taacgtcaaa aaccctgaga gcttcgatta ag                          42

<210> SEQ ID NO 61
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 61
ttgatgacat cgatagcagc atttagcgta ttcacccacc ct                          42

<210> SEQ ID NO 62
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 62
agttaatcgt ctttccagac gcaacgccct cagtagtgta tc                          42

<210> SEQ ID NO 63
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 63
atcagaagta cctttacat cttgaatata gctgaccatc aa                           42

<210> SEQ ID NO 64
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 64
agactccgaa acatacacta aaagcgcgaa acaaactctg aa                          42

<210> SEQ ID NO 65
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 65
gactaaagtg tacaaacgag ggacctgctc catgtagtga at                          42

<210> SEQ ID NO 66
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 66
acgacagaat gggacctgca accagcagcc cactataaat cg                                42

<210> SEQ ID NO 67
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 67
gataagtacc agtaatgtac cgtaacactc agctttgaca ac                                42

<210> SEQ ID NO 68
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 68
ggaagttaaa tcaaaagaaa acaaaattat ataatgaatt at                                42

<210> SEQ ID NO 69
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 69
agcgagtggc ggattgaccg ttatcggcgt taatacccaa aa                                42

<210> SEQ ID NO 70
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 70
ttgctaaaca acttaacaac taagacaggc gggatcgtca cc                                42

<210> SEQ ID NO 71
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 71
cattttaaat gaaaaatcta ttgtaaaggc gcatcggggg at                                42

<210> SEQ ID NO 72
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 72
gattcgcctg attgctggga gaatacccccg gattgtataa gc                               42

<210> SEQ ID NO 73
<211> LENGTH: 42

```
<212> TYPE: DNA
<213> ORGANISM: Artificial Sequence
<220> FEATURE:
<223> OTHER INFORMATION: Synethetic polynucleotide

<400> SEQUENCE: 73
gaaccgaaca cctaaaacga aggagatttg tatcagtaaa tt                     42

<210> SEQ ID NO 74
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 74
ctgagtaatc atagatacat ttcgcaaagg tcattcaatt at                     42

<210> SEQ ID NO 75
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 75
aacaaggggg aaggagctgg cgaaagtatg aaaggtagag cc                     42

<210> SEQ ID NO 76
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 76
cctgatttag aacctaccat agaaattgtt tgcccaatag at                     42

<210> SEQ ID NO 77
<211> LENGTH: 43
<212> TYPE: DNA
<213> ORGANISM: Artificial Sequence
<220> FEATURE:
<223> OTHER INFORMATION: Synethetic polynucleotide

<400> SEQUENCE: 77
taacccacaa gaattgagta tactgaacat gaaaaacaaa ata                    43

<210> SEQ ID NO 78
<211> LENGTH: 43
<212> TYPE: DNA
<213> ORGANISM: Artificial Sequence
<220> FEATURE:
<223> OTHER INFORMATION: Synethetic polynucleotide

<400> SEQUENCE: 78
tttaaattct ggcccagctt tcatcaacat taagtaaaaa taa                    43

<210> SEQ ID NO 79
<211> LENGTH: 43
<212> TYPE: DNA
<213> ORGANISM: Artificial Sequence
<220> FEATURE:
<223> OTHER INFORMATION: Synethetic polynucleotide

<400> SEQUENCE: 79
```
tgagaataga cgctccctca tatattttaa atgtagatag ctt         43

<210> SEQ ID NO 80
<211> LENGTH: 43
<212> TYPE: DNA
<213> ORGANISM: Artificial Sequence
<220> FEATURE:
<223> OTHER INFORMATION: Synethetic polynucleotide

<400> SEQUENCE: 80
tacagcgtgc caagcacgac gaagcatcaa atcaacatca gct         43

<210> SEQ ID NO 81
<211> LENGTH: 43
<212> TYPE: DNA
<213> ORGANISM: Artificial Sequence
<220> FEATURE:
<223> OTHER INFORMATION: Synethetic polynucleotide

<400> SEQUENCE: 81
caagtgtagc ggtcacgcta taaagcgaaa agcaccgtga acc         43

<210> SEQ ID NO 82
<211> LENGTH: 43
<212> TYPE: DNA
<213> ORGANISM: Artificial Sequence
<220> FEATURE:
<223> OTHER INFORMATION: Synethetic polynucleotide

<400> SEQUENCE: 82
cttgctttag aatccttgaa ataattgcat atgcaactaa agt         43

<210> SEQ ID NO 83
<211> LENGTH: 44
<212> TYPE: DNA
<213> ORGANISM: Artificial Sequence
<220> FEATURE:
<223> OTHER INFORMATION: Synethetic polynucleotide

<400> SEQUENCE: 83
aaacaccgga atcactaccg acccaatcgg gcttagtgtt tatc         44

<210> SEQ ID NO 84
<211> LENGTH: 46
<212> TYPE: DNA
<213> ORGANISM: Artificial Sequence
<220> FEATURE:
<223> OTHER INFORMATION: Synethetic polynucleotide

<400> SEQUENCE: 84
agaaaggttc aacgatactt ttgcgggaaa acattcataa agctaa       46

<210> SEQ ID NO 85
<211> LENGTH: 46
<212> TYPE: DNA
<213> ORGANISM: Artificial Sequence
<220> FEATURE:
<223> OTHER INFORMATION: Synethetic polynucleotide

<400> SEQUENCE: 85
aattgagagt tggcaccttg ctgaacctag ggtttcaagg cgatta       46

<210> SEQ ID NO 86
<211> LENGTH: 47
<212> TYPE: DNA
<213> ORGANISM: Artificial Sequence
<220> FEATURE:
<223> OTHER INFORMATION: Synethetic polynucleotide

<400> SEQUENCE: 86
ctgccgtaga tgacgcggtc agtattcagc agcttaacca ataggaa        47

<210> SEQ ID NO 87
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 87
accgagcggc cagccatgtt taccagtggt gaagggcgaa cactgcgc        48

<210> SEQ ID NO 88
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 88
cgatggaaga taatttgtga gagcgcgaac tgatcgaacc acaatgtg        48

<210> SEQ ID NO 89
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 89
accgcacatc gtattttagc ttaaatcaag ataatttgaa acctgact        48

<210> SEQ ID NO 90
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 90
gcagcaggtg ccatcccacg gcggttgttc gttagaatca ggtcgctg        48

<210> SEQ ID NO 91
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 91
ctttacgatg aacggctatc atggtcaatt aacaagcaaa ataggtc        48

<210> SEQ ID NO 92
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 92
tctactcaga gatgacccgt tgggtaatct tatgcaccca gctacaat        48

<210> SEQ ID NO 93
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 93
cgtgcctcat accagacgca tttgccgcca gcagttgggc ttctcacg        48

<210> SEQ ID NO 94
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 94
catcagcgga atcagtgagg cttaaccgcc ctcagtcagg gattccaca        49

<210> SEQ ID NO 95
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 95
ctaaacgacg agcccagcgg cagtgtcgtg gcgaaaaggg atctcaggg        49

<210> SEQ ID NO 96
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 96
agattatttt gcgcaaggca aagaatttcc aataaatgtg tgaagatga        49

<210> SEQ ID NO 97
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 97
gagaggccaa tcaagaacaa gaaaaaggtg gcaacagttt atgggcgac        49

<210> SEQ ID NO 98
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 98
aaaatcttaa gcaataaagc ctaatagaag ggtgtatgat attacctga        49

<210> SEQ ID NO 99
<211> LENGTH: 49
<212> TYPE: DNA
<213> ORGANISM: Artificial Sequence
<220> FEATURE:
<223> OTHER INFORMATION: Synethetic polynucleotide

```
<400> SEQUENCE: 99
agcgggatca atccgccggg ccaaccagct tgcctcggtt tatgaataa              49

<210> SEQ ID NO 100
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 100
tatcggccgt ttttgattgc ccgaccagga acccttctcc gtcccggaa              49

<210> SEQ ID NO 101
<211> LENGTH: 79
<212> TYPE: DNA
<213> ORGANISM: Artificial Sequence
<220> FEATURE:
<223> OTHER INFORMATION: Synethetic polynucleotide

<400> SEQUENCE: 101
tttcatagaa ttaagaaggc ttatccgagc aagcgaatga ccaacagtat ttcacacgtc  60
aactcataca actctgatc                                               79

<210> SEQ ID NO 102
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 102
tttgcggcat catacgaacg aatataacgt tttaatgaat atagagagt              49

<210> SEQ ID NO 103
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 103
actatggttg ctttaggagg ccgcggtcct tgctggtaat ataatactt              49

<210> SEQ ID NO 104
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 104
aatataccgc gcagaggcgt gaataatgtt taacgtcgac aagataata              49

<210> SEQ ID NO 105
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 105
aggaagccaa atgctaagag ccgaagccct ttttaaagaa ctatagcgt              49
```

<210> SEQ ID NO 106
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 106
atcaatatct ggtcgaaggt tttacgccgc gatcggtgcg ggttatcat        49

<210> SEQ ID NO 107
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 107
tttccttgca gatgccactc tgtcacgggg aaagccggat agcggccaa        49

<210> SEQ ID NO 108
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 108
aaatcccgta gattttcagg gaagggtgtt tggaaaacat ctacaatgc        49

<210> SEQ ID NO 109
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 109
aaaaaaactg ctcagaaaca gccggaaagc cgccataacg cccaaatat        49

<210> SEQ ID NO 110
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 110
ttgcgagtgg gattcagtca gtgccttgac caactccatt aaacgggta        49

<210> SEQ ID NO 111
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 111
gcggccaatc gttatcgaca tgcctttagt gatgaccggc caaggtttc        49

<210> SEQ ID NO 112
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 112
gctacagtta gacaggaaaa aaatattacc gccagacgca aacaccgag        49

<210> SEQ ID NO 113
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 113
tgtacaacgg catctcgtca taaacattgg gtaagagcac acgtcagcg        49

<210> SEQ ID NO 114
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 114
tccagcgtgc cggtagtcac agttccggca tacctacatt ttttggcag        49

<210> SEQ ID NO 115
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 115
gcaaaaaggt aaatttagaa gagaagagtc aatagtgaat acaaggata        49

<210> SEQ ID NO 116
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 116
aaccatcctg ttgatataag tatagccccc gacaagcttt cgtagtaat        49

<210> SEQ ID NO 117
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 117
taaaggctcg gtcgaggctc cgaatgcctg tagaatcctc atacaggcg        49

<210> SEQ ID NO 118
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 118
accgtacgcc ttgataccga tagttgcggg aatagccagg cgaaatacg        49

<210> SEQ ID NO 119

```
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 119
agatcgcaac aaacaacaac cttaaaaaca aatcaggtcg aggtgccgt          49

<210> SEQ ID NO 120
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 120
gaaccctgaa aggatagact ttctgacctg aaagcattca ccgcccct          49

<210> SEQ ID NO 121
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 121
acagaggtga ggactcgaat gcccccgatt tagagcttgt gccccgggt          49

<210> SEQ ID NO 122
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 122
taatgaagag gctgggtttt gtgtagcata gcaagcccaa tatttctta          49

<210> SEQ ID NO 123
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 123
tcgctaatct aaagagcact aacaactgaa cgttattaat taaaacaga          49

<210> SEQ ID NO 124
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 124
ttgaaagcat aaggataaat tgtgtcgacg agaaaaaccg gacaccatt          49

<210> SEQ ID NO 125
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 125
```
taacgagaac ctcccaagac aaagaacgtt aatggcaggg aaaagaacg          49

<210> SEQ ID NO 126
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 126
agtaacaatg aattttctgt atttcgtcgc cgtcgagagg cagaagttt           49

<210> SEQ ID NO 127
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 127
aaaacgaaaa tcagtaagca gatagccgca ataattttaa caaaatagc           49

<210> SEQ ID NO 128
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 128
atcaacgagc cagcaaaatc agagccatgg aagaaaacat tattacagg           49

<210> SEQ ID NO 129
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 129
acgggagcac cagaaattac cttatgcgcg ttaataccgt caaattatt           49

<210> SEQ ID NO 130
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 130
acgccaacaa cgctcataaa ttcagaagcc taaatcgaga aatcgacta           49

<210> SEQ ID NO 131
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 131
taattttttc acgtgccttt acataaccga tatatcgctt ttcatcgga           49

<210> SEQ ID NO 132
<211> LENGTH: 49
<212> TYPE: DNA

```
<213> ORGANISM: Artificial Sequence
<220> FEATURE:
<223> OTHER INFORMATION: Synethetic polynucleotide

<400> SEQUENCE: 132
cgaggcggga atcacaggtc ttaccagtat aaagccatgt aaaaaccga         49

<210> SEQ ID NO 133
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 133
attttaagcc ctgaaatccg ccgcagacgg tcaataggac agatcttga          49

<210> SEQ ID NO 134
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 134
atttcaactt taatttgagg ctcggcattt tcgtggcaag gcagtttta          49

<210> SEQ ID NO 135
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 135
caataattta aactactgcg gaatcgtaga ctggggcatg aacgtagaa          49

<210> SEQ ID NO 136
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 136
tgtaaatgct gatgcaaatc gtgtgatgaa gccgaacctc ccgacttgc          49

<210> SEQ ID NO 137
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 137
ttaaaggttt aggcaccaga cgacgatact atcattatca acaatagat          49

<210> SEQ ID NO 138
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 138
aacggaaata atatcccatc caagtcctta gaaaattcat caaaaacca          49
```

<210> SEQ ID NO 139
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 139 ttaagcatc ttacaagaaa cagagagaca gagggatttt ttttatcc                49

<210> SEQ ID NO 140
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 140
cctcagagtt aaagtaattc tctaatgcag aacgcccaat caacgggta                49

<210> SEQ ID NO 141
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 141
cgagcatgta gaaagcctgt taaccctcgg catagcgttt gcgtagcgc                49

<210> SEQ ID NO 142
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 142
aaggagcatg gctatacgtg gcacagacat ggattcacac ccatgcgcc                49

<210> SEQ ID NO 143
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 143
cattaaacgc caaatcaact aatgcagagc cgccgccagc aacgaacta                49

<210> SEQ ID NO 144
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 144
ttattagtaa gagccgccaa aaggaattgc caccaacgat tgcagttta                49

<210> SEQ ID NO 145
<211> LENGTH: 49
<212> TYPE: DNA
<213> ORGANISM: Artificial Sequence
<220> FEATURE:

<223> OTHER INFORMATION: Synethetic polynucleotide

<400> SEQUENCE: 145
accattaaat tatcaaattg acaggaggca ttgtgacgag tatcgcctg         49

<210> SEQ ID NO 146
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 146
aacagcattg tagcccagaa ccgctcatgg aaaaacgatt aatcattgc         49

<210> SEQ ID NO 147
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 147
taatttagga aacgaacaaa ggcccaatgt attctgcgca ttgagagaa         49

<210> SEQ ID NO 148
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 148
tcacagtagg tggacaatcg gcgaaacgga aaaggggggg tttggtgct         49

<210> SEQ ID NO 149
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 149
aaaattcggg gacgaaagcg ccattcgcga gaatcaaaca attcagatg         49

<210> SEQ ID NO 150
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 150
cacactccta ctccaacatc cacccttgat cagagttgta tg               42

<210> SEQ ID NO 151
<211> LENGTH: 8064
<212> TYPE: DNA
<213> ORGANISM: Artificial Sequence
<220> FEATURE:
<223> OTHER INFORMATION: Scaffold sequence M13 viral DNA

<400> SEQUENCE: 151
gaattcgagc tcggtacccg gggatcctca actgtgagga ggctcacgga cgcgaagaac    60
aggcacgcgt gctggcagaa accccggta tgaccgtgaa aacggcccgc cgcattctgg   120

```
ccgcagcacc acagagtgca caggcgcgca gtgacactgc gctggatcgt ctgatgcagg      180
gggcaccggc accgctggct gcaggtaacc cggcatctga tgccgttaac gatttgctga      240
acacaccagt gtaagggatg tttatgacga gcaaagaaac ctttacccat taccagccgc      300
agggcaacag tgacccggct cataccgcaa ccgcgcccgg cggattgagt gcgaaagcgc      360
ctgcaatgac cccgctgatg ctggacacct ccagccgtaa gctggttgcg tgggatggca      420
ccaccgacgg tgctgccgtt ggcattcttg cggttgctgc tgaccagacc agcaccacgc      480
tgacgttcta caagtccggc acgttccgtt atgaggatgt gctctggccg gaggctgcca      540
gcgacgagac gaaaaaacgg accgcgtttg ccggaacggc aatcagcatc gtttaacttt      600
acccttcatc actaaaggcc gcctgtgcgg ctttttttac gggattttttt tatgtcgatg      660 tacacaaccg cccaactgct ggcggcaaat gagcagaaat ttaagtttga tccgctgttt      720
ctgcgtctct ttttccgtga gagctatccc ttcaccacgg agaaagtcta tctctcacaa      780
attccgggac tggtaaacat ggcgctgtac gtttcgccga ttgtttccgg tgaggttatc      840
cgttcccgtg gcggctccac ctctgaaagc ttggcactgg ccgtcgtttt acaacgtcgt      900
gactgggaaa accctggcgt tacccaactt aatcgccttg cagcacatcc ccctttcgcc      960
agctggcgta atagcgaaga ggcccgcacc gatcgccctt cccaacagtt gcgcagcctg     1020
aatggcgaat ggcgctttgc ctggtttccg gcaccagaag cggtgccgga agctggctg      1080 gagtgcgatc ttcctgaggc cgatactgtc gtcgtcccct caaactggca gatgcacggt     1140
tacgatgcgc ccatctacac caacgtgacc tatcccatta cggtcaatcc gccgtttgtt     1200
cccacggaga atccgacggg ttgttactcg ctcacattta atgttgatga agctggcta      1260 caggaaggcc agacgcgaat tattttttgat ggcgttccta ttggttaaaa atgagctga     1320 tttaacaaaa atttaatgcg aattttaaca aaatattaac gtttacaatt taaatatttg     1380
cttatacaat cttcctgttt ttggggcttt tctgattatc aaccggggta catatgattg     1440
acatgctagt tttacgatta ccgttcatcg attctcttgt ttgctccaga ctctcaggca     1500
atgacctgat agcctttgta gatctctcaa aaatagctac cctctccggc attaatttat     1560
cagctagaac ggttgaatat catattgatg gtgatttgac tgtctccggc ctttctcacc     1620
cttttgaatc tttacctaca cattactcag gcattgcatt taaaatatat gagggttcta     1680 aaaatttta tccttgcgtt gaaataaagg cttctcccgc aaaagtatta cagggtcata     1740 atgttttttgg tacaaccgat ttagctttat gctctgaggc tttattgctt aattttgcta     1800
attctttgcc ttgcctgtat gatttattgg atgttaatgc tactactatt agtagaattg     1860
atgccaccct ttcagctcgc gccccaaatg aaaatatagc taaacaggtt attgaccatt     1920
tgcgaaatgt atctaatggt caaactaaat ctactcgttc gcagaattgg gaatcaactg     1980
ttatatggaa tgaaacttcc agacaccgta ctttagttgc atatttaaaa catgttgagc     2040
tacagcatta tattcagcaa ttaagctcta agccatccgc aaaaatgacc tcttatcaaa     2100
aggagcaatt aaaggtactc tctaatcctg acctgttgga gtttgcttcc ggtctggttc     2160
gctttgaagc tcgaattaaa acgcgatatt tgaagtcttt cgggcttcct cttaatcttt     2220
ttgatgcaat ccgctttgct tctgactata atagtcaggg taaagacctg attttttgatt     2280 tatggtcatt ctcgttttct gaactgttta aagcatttga gggggattca atgaatattt     2340
atgacgattc cgcagtattg gacgctatcc agtctaaaca ttttactatt accccctctg     2400
gcaaaacttc ttttgcaaaa gcctctcgct attttggttt ttatcgtcgt ctggtaaacg     2460
```

| | |
|---|---|
| agggttatga tagtgttgct cttactatgc ctcgtaattc cttttggcgt tatgtatctg | 2520 |
| cattagttga atgtggtatt cctaaatctc aactgatgaa tctttctacc tgtaataatg | 2580 |
| ttgttccgtt agttcgtttt attaacgtag attttttctt ccaacgtcct gactggtata | 2640 |
| atgagccagt tcttaaaatc gcataaggta attcacaatg attaaagttg aaattaaacc | 2700 |
| atctcaagcc caatttacta ctcgttctgg tgtttctcgt cagggcaagc cttattcact | 2760 |
| gaatgagcag ctttgttacg ttgatttggg taatgaatat ccggttcttg tcaagattac | 2820 |
| tcttgatgaa ggtcagccag cctatgcgcc tggtctgtac accgttcatc tgtcctcttt | 2880 |
| caaagttggt cagttcggtt cccttatgat tgaccgtctg cgcctcgttc cggctaagta | 2940 |
| acatggagca ggtcgcggat tcgacacaa tttatcaggc gatgatacaa atctccgttg | 3000 |
| tactttgttt cgcgcttggt ataatcgctg ggggtcaaag atgagtgttt tagtgtattc | 3060 |
| ttttgcctct ttcgttttag gttggtgcct tcgtagtggc attacgtatt ttacccgttt | 3120 |
| aatggaaact tcctcatgaa aaagtcttta gtcctcaaag cctctgtagc cgttgctacc | 3180 |
| ctcgttccga tgctgtcttt cgctgctgag ggtgacgatc ccgcaaaagc ggcctttaac | 3240 |
| tccctgcaag cctcagcgac cgaatatatc ggttatgcgt gggcgatggt tgttgtcatt | 3300 |
| gtcggcgcaa ctatcggtat caagctgttt aagaaattca cctcgaaagc aagctgataa | 3360 |
| accgatacaa ttaaaggctc cttttggagc cttttttttg gagattttca acgtgaaaaa | 3420 |
| attattattc gcaattcctt tagttgttcc tttctattct cactccgctg aaactgttga | 3480 |
| aagttgttta gcaaaatccc atacagaaaa ttcatttact aacgtctgga agacgacaa | 3540 |
| aactttagat cgttacgcta actatgaggg ctgtctgtgg aatgctacag gcgttgtagt | 3600 |
| ttgtactggt gacgaaactc agtgttacgg tacatgggtt cctattgggc ttgctatccc | 3660 |
| tgaaaatgag ggtggtggct ctgagggtgg cggttctgag ggtggcggtt ctgagggtgg | 3720 |
| cggtactaaa cctcctgagt acggtgatac acctattccg ggctatactt atatcaaccc | 3780 |
| tctcgacggc acttatccgc ctggtactga gcaaaacccc gctaatccta atccttctct | 3840 |
| tgaggagtct cagcctctta atactttcat gtttcagaat aataggttcc gaaataggca | 3900 |
| gggggcatta actgtttata cgggcactgt tactcaaggc actgaccccg ttaaaactta | 3960 |
| ttaccagtac actcctgtat catcaaaagc catgtatgac gcttactgga acggtaaatt | 4020 |
| cagagactgc gctttccatt ctggctttaa tgaggattta tttgtttgtg aatatcaagg | 4080 |
| ccaatcgtct gacctgcctc aacctcctgt caatgctggc ggcggctctg gtggtggttc | 4140 |
| tggtggcggc tctgagggtg gtggctctga gggtggcggt tctgagggtg cggctctga | 4200 |
| gggaggcggt tccggtggtg gctctggttc cggtgatttt gattatgaaa agatggcaaa | 4260 |
| cgctaataag ggggctatga ccgaaaatgc cgatgaaaac gcgctacagt ctgacgctaa | 4320 |
| aggcaaactt gattctgtcg ctactgatta cggtgctgct atcgatggtt tcattggtga | 4380 |
| cgtttccggc cttgctaatg gtaatggtgc tactggtgat tttgctggct ctaattccca | 4440 |
| aatggctcaa gtcggtgacg gtgataattc acctttaatg aataatttcc gtcaatattt | 4500 |
| accttccctc cctcaatcgg ttgaatgtcg cccttttgtc tttggcgctg gtaaaccata | 4560 |
| tgaattttct attgattgtg acaaaataaa cttattccgt ggtgtctttg cgtttctttt | 4620 |
| atatgttgcc acctttatgt atgtattttc tacgtttgct aacatactgc gtaataagga | 4680 |
| gtcttaatca tgccagttct tttgggtatt ccgttattat tgcgtttcct cggtttcctt | 4740 |
| ctggtaactt tgttcggcta tctgcttact ttcttaaaaa agggcttcgg taagatagc | 4800 |
| attgctattt cattgtttct tgctcttatt attgggctta actcaattct gtgggttat | 4860 |

```
ctctctgata ttagcgctca attaccctct gactttgttc agggtgttca gttaattctc    4920
ccgtctaatg cgcttccctg tttttatgtt attctctctg taaaggctgc tattttcatt    4980
tttgacgtta aacaaaaaat cgtttcttat ttggattggg ataaataata tggctgttta    5040
ttttgtaact ggcaaattag gctctggaaa gacgctcgtt agcgttggta agattcagga    5100
taaaattgta gctgggtgca aaatagcaac taatcttgat ttaaggcttc aaaacctccc    5160
gcaagtcggg aggttcgcta aaacgcctcg cgttcttaga ataccggata agccttctat    5220
atctgatttg cttgctattg ggcgcggtaa tgattcctac gatgaaaata aaaacggctt    5280
gcttgttctc gatgagtgcg gtacttggtt taatacccgt tcttggaatg ataaggaaag    5340
acagccgatt attgattggt ttctacatgc tcgtaaatta ggatgggata ttattttctct   5400 tgttcaggac ttatctattg ttgataaaca ggcgcgttct gcattagctg aacatgttgt    5460
ttattgtcgt cgtctggaca gaattacttt acctttgtc ggtactttat attctcttat     5520
tactggctcg aaaatgcctc tgcctaaatt acatgttggc gttgttaaat atggcgattc    5580
tcaattaagc cctactgttg agcgttggct ttatactggt aagaatttgt ataacgcata    5640
tgatactaaa caggcttttt ctagtaatta tgattccggt gtttattctt atttaacgcc    5700
ttatttatca cacggtcggt atttcaaacc attaaattta ggtcagaaga tgaaattaac    5760
taaaatatat ttgaaaaagt tttctcgcgt tctttgtctt gcgattggat ttgcatcagc    5820
atttacatat agttatataa cccaacctaa gccggaggtt aaaaaggtag tctctcagac    5880
ctatgatttt gataaattca ctattgactc ttctcagcgt cttaatctaa gctatcgcta    5940
tgttttcaag gattctaagg gaaaattaat taatagcgac gatttacaga agcaaggtta    6000
ttcactcaca tatattgatt tatgtactgt ttccattaaa aaaggtaatt caaatgaaat    6060
tgttaaatgt aattaatttt gttttcttga tgtttgtttc atcatcttct tttgctcagg    6120
taattgaaat gaataattcg cctctgcgcg attttgtaac ttggtattca agcaatcag    6180 gcgaatccgt tattgtttct cccgatgtaa aaggtactgt tactgtatat tcatctgacg    6240
ttaaacctga aaatctacgc aatttcttta tttctgtttt acgtgcaaat aatttttgata    6300 tggtaggttc taaccettcc attattcaga agtataatcc aaacaatcag gattatattg    6360
atgaattgcc atcatctgat aatcaggaat atgatgataa ttccgctcct tctggtggtt    6420
tctttgttcc gcaaaatgat aatgttactc aaacttttaa aattaataac gttcgggcaa    6480
aggatttaat acgagttgtc gaattgtttg taaagtctaa tacttctaaa tcctcaaatg    6540
tattatctat tgacggctct aatctattag ttgttagtgc tcctaaagat attttagata    6600
accttcctca attcctttca actgttgatt tgccaactga ccagatattg attgagggtt    6660
tgatatttga ggttcagcaa ggtgatgctt tagattttc atttgctgct ggctctcagc     6720
gtggcactgt tgcaggcggt gttaatactg accgcctcac ctctgtttta tcttctgctg    6780
gtggttcgtt cggtattttt aatggcgatg tttagggct atcagttcgc gcattaaaga    6840
ctaatagcca ttcaaaaata ttgtctgtgc cacgtattct tacgctttca ggtcagaagg    6900
gttctatctc tgttggccag aatgtcccct ttattactgg tcgtgtgact ggtgaatctg    6960
ccaatgtaaa taatccattt cagacgattg agcgtcaaaa tgtaggtatt tccatgagcg    7020 ttttcctgt tgcaatggct ggcggtaata ttgttctgga tattaccagc aaggccgata    7080
gtttgagttc ttctactcag gcaagtgatg ttattactaa tcaaagaagt attgctacaa    7140
cggttaattt gcgtgatgga cagactcttt tactcggtgg cctcactgat tataaaaaca    7200
```

```
cttctcagga ttctggcgta ccgttcctgt ctaaatccc tttaatcggc ctcctgttta    7260
gctcccgctc tgattctaac gaggaaagca cgttatacgt gctcgtcaaa gcaaccatag    7320
tacgcgccct gtagcggcgc attaagcgcg gcgggtgtgg tggttacgcg cagcgtgacc    7380
gctacacttg ccagcgccct agcgcccgct cctttcgctt tcttcccttc ctttctcgcc    7440
acgttcgccg gctttccccg tcaagctcta atcggggggc tccctttagg gttccgattt    7500
agtgctttac ggcacctcga ccccaaaaaa cttgatttgg gtgatggttc acgtagtggg    7560
ccatcgccct gatagacggt ttttcgccct ttgacgttgg agtccacgtt ctttaatagt    7620
ggactcttgt tccaaactgg aacaacactc aaccctatct cgggctattc ttttgattta    7680
taagggattt tgccgatttc ggaaccacca tcaaacagga ttttcgcctg ctggggcaaa    7740
ccagcgtgga ccgcttgctg caactctctc agggccaggc ggtgaagggc aatcagctgt    7800
tgcccgtctc actggtgaaa agaaaaacca ccctggcgcc caatacgcaa accgcctctc    7860
cccgcgcgtt ggccgattca ttaatgcagc tggcacgaca ggtttcccga ctggaaagcg    7920
ggcagtgagc gcaacgcaat taatgtgagt tagctcactc attaggcacc ccaggcttta    7980
cactttatgc ttccggctcg tatgttgtgt ggaattgtga gcggataaca atttcacaca    8040
ggaaacagct atgaccatga ttac                                           8064
```

```
<210> SEQ ID NO 152
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 152
gcgcgtaaag cccccgattt agagcttgac ggggaaagcc gctggcaa                 48

<210> SEQ ID NO 153
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 153
ccagcgcacc ggtgccccct gcatttcgca ctcaatccgc ggtcattg                 48

<210> SEQ ID NO 154
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 154
tgtggtgcat cagatgccgg gttaatgagc cg                                  32

<210> SEQ ID NO 155
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 155
gtgagcctcc tcacagttga ggatgtgcac tc                                  32
```

<210> SEQ ID NO 156
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 156
gtgtagcggc ttaatgcgcc gctaagaatc agagcgggag caggaacg        48

<210> SEQ ID NO 157
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 157
tcctcgttca gggcgcgtac tatggagcgg gcgctagggc ggcgaacg        48

<210> SEQ ID NO 158
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 158
gaggccgacc accacacccg ccgcgtcacg ct        32

<210> SEQ ID NO 159
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 159
ggtcactgag cttacggctg gaggaacgtg ccggacttgt tgattgcc        48

<210> SEQ ID NO 160
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 160
ttaacggctg cggccagaat gcggtcgcgt cc        32

<210> SEQ ID NO 161
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 161
cataacggtg tccagcatca gcggcgggcg cggttgcggt cctgcagc        48

<210> SEQ ID NO 162
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 162
agcgtggtgc catcccacgc aaccttgccc tgcggctggt gcaaatcg                48

<210> SEQ ID NO 163
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 163
gtacgccacc atcacgcaaa ttaaacatca cttgcctgag cagccatt                48

<210> SEQ ID NO 164
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 164
caggcgctca gcctccggcc agagttcgtc tc                                 32

<210> SEQ ID NO 165
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 165
ctcaaactga gtaaaagagt ctgtgaatcc tgagaagtgt acgtgctt                48

<210> SEQ ID NO 166
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 166
gtcgctggaa cagcggatca aacttggtga agggatagct                         40

<210> SEQ ID NO 167
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 167
gttccggctg ccgccagcag ttggtcccgg aatttgtgag taaaacga                48

<210> SEQ ID NO 168
<211> LENGTH: 43
<212> TYPE: DNA
<213> ORGANISM: Artificial Sequence
<220> FEATURE:
<223> OTHER INFORMATION: Synethetic polynucleotide

<400> SEQUENCE: 168
gcaacaggaa aaagagacg cagatctttg attagtaata ccg                      43

<210> SEQ ID NO 169
<211> LENGTH: 40

<212> TYPE: DNA
<213> ORGANISM: Artificial Sequence
<220> FEATURE:
<223> OTHER INFORMATION: Synethetic polynucleotide

<400> SEQUENCE: 169
ctcacggaaa acgctcatgg aaatacctac atcacgacca        40

<210> SEQ ID NO 170
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 170
tttctccgta aatttctgct cattaaacgc ggtccgtttt cacatcct        48

<210> SEQ ID NO 171
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 171
tttaccaggc ggttgtgtac atcgtaaagt taaacgatgc agaacgtc        48

<210> SEQ ID NO 172
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 172
accagtcatt tgacgctcaa tcgtagaaca atattaccgc tagaagaa        48

<210> SEQ ID NO 173
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 173
tctgtaaatc gtcgcttgaa tttatcaaaa tc        32

<210> SEQ ID NO 174
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 174
agggttttcc cagtcacgac gttgagatag ac        32

<210> SEQ ID NO 175
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 175
cggccagtgc caagctttca gagggcgcca tg                32

<210> SEQ ID NO 176
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 176
gatagaaccc ttctgattta atgcaaatta tt                32

<210> SEQ ID NO 177
<211> LENGTH: 45
<212> TYPE: DNA
<213> ORGANISM: Artificial Sequence
<220> FEATURE:
<223> OTHER INFORMATION: Synethetic polynucleotide

<400> SEQUENCE: 177
gatgtgctgc aaggcgatta atcgcactcc agccagcatc ggcct    45

<210> SEQ ID NO 178
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 178
cgctattacg ccagcttggt gccggaaacc agtgcatctg         40

<210> SEQ ID NO 179
<211> LENGTH: 24
<212> TYPE: DNA
<213> ORGANISM: Artificial Sequence
<220> FEATURE:
<223> OTHER INFORMATION: Synethetic polynucleotide

<400> SEQUENCE: 179
ctgttgggaa gggcgacatt cagg                          24

<210> SEQ ID NO 180
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 180
gcgaactgaa cgaaccacca gcagacaccg ccatacataa         40

<210> SEQ ID NO 181
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 181
acagaggttg aatggctatt agtccctgaa agaaagtaat         40

<210> SEQ ID NO 182
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 182
aaataccgat agccctaaaa catccattct ggccaacaga                          40

<210> SEQ ID NO 183
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 183
caggaagaat caaaaataat tcgcaaccaa taggaacgcc actagcat                 48

<210> SEQ ID NO 184
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 184
ccagtttggc cagctttcat caaccattaa at                                  32

<210> SEQ ID NO 185
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 185
cgtaaccggc aaagcgccat tcgctcggtg cgggcctctt                          40

<210> SEQ ID NO 186
<211> LENGTH: 45
<212> TYPE: DNA
<213> ORGANISM: Artificial Sequence
<220> FEATURE:
<223> OTHER INFORMATION: Synethetic polynucleotide

<400> SEQUENCE: 186
gaggcggtca gtattaaaga taaagtagaa actctgtcca gacga                    45

<210> SEQ ID NO 187
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 187
tgcaacagtc taaagcatca ccttatctgg tccaaagtta                          40

<210> SEQ ID NO 188
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 188
ttttgttata atcagaaaag ccccccctgag ag                                 32

<210> SEQ ID NO 189
<211> LENGTH: 34
<212> TYPE: DNA
<213> ORGANISM: Artificial Sequence
<220> FEATURE:
<223> OTHER INFORMATION: Synethetic polynucleotide

<400> SEQUENCE: 189
gtaccgagct cgaattccct aaagggcaga cgat                           34

<210> SEQ ID NO 190
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 190
agttggcatc taaaatatct ttagtagaag ta                             32

<210> SEQ ID NO 191
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 191
gttgaaagag cagcaaatga aaaatgccac gctgagagcc gccattaa            48

<210> SEQ ID NO 192
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 192
gtcaatcaga acggtaatcg taaagccgga gacagtcaaa caaaaggg            48

<210> SEQ ID NO 193
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 193
gaagattgat tttgttaaaa ttcgattaaa tgtgagcgag gggcgcat            48

<210> SEQ ID NO 194
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 194
acaactaaca aaccctcaat caatgctgaa cctaagaacg caatcaat            48

<210> SEQ ID NO 195
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 195
gaatcgatta tgtaccccgg ttgaaatcag ctcattttt gtctggcc　　　　　　　　48

<210> SEQ ID NO 196
<211> LENGTH: 41
<212> TYPE: DNA
<213> ORGANISM: Artificial Sequence
<220> FEATURE:
<223> OTHER INFORMATION: Synethetic polynucleotide

<400> SEQUENCE: 196
tctggagcat tcaaccgttc tagctgcaat gcctgagtaa t　　　　　　　　　　41

<210> SEQ ID NO 197
<211> LENGTH: 24
<212> TYPE: DNA
<213> ORGANISM: Artificial Sequence
<220> FEATURE:
<223> OTHER INFORMATION: Synethetic polynucleotide

<400> SEQUENCE: 197
ttgagagatc tacaaagaga gggt　　　　　　　　　　　　　　　　　　　　24

<210> SEQ ID NO 198
<211> LENGTH: 45
<212> TYPE: DNA
<213> ORGANISM: Artificial Sequence
<220> FEATURE:
<223> OTHER INFORMATION: Synethetic polynucleotide

<400> SEQUENCE: 198
aatacatttg aggattgagc actagaatct tacgaggcgt tttag　　　　　　　　45

<210> SEQ ID NO 199
<211> LENGTH: 37
<212> TYPE: DNA
<213> ORGANISM: Artificial Sequence
<220> FEATURE:
<223> OTHER INFORMATION: Synethetic polynucleotide

<400> SEQUENCE: 199
ttagactttt gcccgaacgt tattaatttt aaaagtt　　　　　　　　　　　　37

<210> SEQ ID NO 200
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 200
attcgacaga attgaggaag gttaaatcaa ca　　　　　　　　　　　　　　32

<210> SEQ ID NO 201
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 201
taatgccggg ctatcaggtc attgaaaaac ag　　　　　　　　　　　　　　32

<210> SEQ ID NO 202

<210> SEQ ID NO 202
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 202
tgagaaagac tcgtatcaga aggagcgggc aaggcaaaga                              40

<210> SEQ ID NO 203
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 203
aggccggatt aacaacgcca acatttgaga at                                      32

<210> SEQ ID NO 204
<211> LENGTH: 37
<212> TYPE: DNA
<213> ORGANISM: Artificial Sequence
<220> FEATURE:
<223> OTHER INFORMATION: Synethetic polynucleotide

<400> SEQUENCE: 204
tgagtaacat tatccaacgc taaaacaggt aaatcct                                 37

<210> SEQ ID NO 205
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 205
attagcaata aagatttcac catcaatatg ataaacaaga                              40

<210> SEQ ID NO 206
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 206
tgtaccaagg gcgcgagctg aaaacaaatg gtcaataacc tgtagctc                     48

<210> SEQ ID NO 207
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 207
gattatcagg aacaaagaaa ccactaaatc cttacaaaca                              40

<210> SEQ ID NO 208
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 208

-continued atacagaatt atcatcaagg gttagaagat tc                                         32

<210> SEQ ID NO 209
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 209
agtagcatgt agatttagtt tgacagtacg gtgtctggaa ctttaatt                        48

<210> SEQ ID NO 210
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 210
caattctact cagagcataa agctatttta aatgataaat                                 40

<210> SEQ ID NO 211
<211> LENGTH: 37
<212> TYPE: DNA
<213> ORGANISM: Artificial Sequence
<220> FEATURE:
<223> OTHER INFORMATION: Synethetic polynucleotide

<400> SEQUENCE: 211
taatcctgat tgtataacat aaaaatagcc tgctaca                                    37

<210> SEQ ID NO 212
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 212
ccaattctgc gaacgataac atccaataaa tc                                         32

<210> SEQ ID NO 213
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 213
cagttcctac catatcagaa acaataacag gt                                         32

<210> SEQ ID NO 214
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 214
aacatgtttt gcggatggct tagacccgaa agacttcaaa cataaatc                        48

<210> SEQ ID NO 215
<211> LENGTH: 48
<212> TYPE: DNA

<213> ORGANISM: Artificial Sequence
<220> FEATURE:
<223> OTHER INFORMATION: Synethetic polynucleotide

<400> SEQUENCE: 215
acatcgggaa aattatttgc acgttacttc tgaataatgg atattcct                48

<210> SEQ ID NO 216
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 216
caggattaga gagtacgttt cattccatat aa                                 32

<210> SEQ ID NO 217
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 217
gctcctttga gcttcaaagc gaacatgctt taaacagttc gactggat                48

<210> SEQ ID NO 218
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 218 ggtcatttt aaatatgcaa ctaacattag atacatttcg ggtggcat                 48

<210> SEQ ID NO 219
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 219
tccaacggat tcgccttgat gaaacaatat tc                                 32

<210> SEQ ID NO 220
<211> LENGTH: 26
<212> TYPE: DNA
<213> ORGANISM: Artificial Sequence
<220> FEATURE:
<223> OTHER INFORMATION: Synethetic polynucleotide

<400> SEQUENCE: 220
gcgaattatt catatccaaa tagtta                                        26

<210> SEQ ID NO 221
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 221
attgaatccc cctcaacaga ccggaagcaa ac                                 32

<210> SEQ ID NO 222
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 222
aaaaatcatt ttgccagagg gggtataaaa acagttgaga                              40

<210> SEQ ID NO 223
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 223
aattacatcc tgagcaaaag aagagattgc tttgaatacc tacctttt                    48

<210> SEQ ID NO 224
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 224
ataaaacatc aagaaatgag tgaataacca cg                                      32

<210> SEQ ID NO 225
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 225
agcgtccaac actatctgca gatacataac gctcattata                              40

<210> SEQ ID NO 226
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 226
aatgtttaag aaaacgagaa tgactatcgc gttttaattc tgataaga                    48

<210> SEQ ID NO 227
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 227
ttcctgtaag gggacgacga cagttttccg gcaccgcttc ggcgaaag                    48

<210> SEQ ID NO 228
<211> LENGTH: 32
<212> TYPE: DNA
<213> ORGANISM: Artificial Sequence
<220> FEATURE:

<223> OTHER INFORMATION: Synethetic polynucleotide

<400> SEQUENCE: 228
aggcatagta agagcaatac tgcggaatcg tc                                    32

<210> SEQ ID NO 229
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 229
tcaactaaat aaccctcgtt taccagacga cgaatagtaa                            40

<210> SEQ ID NO 230
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 230
tttaggaaat ctacgttaat aaaaattggg ct                                    32

<210> SEQ ID NO 231
<211> LENGTH: 27
<212> TYPE: DNA
<213> ORGANISM: Artificial Sequence
<220> FEATURE:
<223> OTHER INFORMATION: Synethetic polynucleotide

<400> SEQUENCE: 231
gattcatcca aaatagcgag aggcttt                                          27

<210> SEQ ID NO 232
<211> LENGTH: 37
<212> TYPE: DNA
<213> ORGANISM: Artificial Sequence
<220> FEATURE:
<223> OTHER INFORMATION: Synethetic polynucleotide

<400> SEQUENCE: 232
ttacaggtag aaagtgcctt gaaaagaagg gtcttta                               37

<210> SEQ ID NO 233
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 233
ataggtaaga actggccaaa aggaattttg ct                                    32

<210> SEQ ID NO 234
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 234
ccagtcagat cattgtgaat tacctcaaga gtaatcttga cggtgtac                   48

<210> SEQ ID NO 235
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 235
gagactacct ttttaatcgc aagacaaaga ac                            32

<210> SEQ ID NO 236
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 236
tgagatggat tacccaaatc aacggaactg accaactttg gacctgct           48

<210> SEQ ID NO 237
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 237
gcgaggctga ccttcattat gcgattttct ga                            32

<210> SEQ ID NO 238
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 238
ggatattctt taatttcaac tttagacgtt gggaagaaaa taccacat           48

<210> SEQ ID NO 239
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 239
tttttcaaat atatttataa ataaggcgtt aa                            32

<210> SEQ ID NO 240
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 240
agaccaggat catcgcctga taaattatac ca                            32

<210> SEQ ID NO 241
<211> LENGTH: 43
<212> TYPE: DNA
<213> ORGANISM: Artificial Sequence
<220> FEATURE:
<223> OTHER INFORMATION: Synethetic polynucleotide

<400> SEQUENCE: 241
agggaaccta acaaagctgc tcatccagaa cgtcttagcc cgg 43

<210> SEQ ID NO 242
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 242
ataagcggag atttgtcgca taggctgaaa ac 32

<210> SEQ ID NO 243
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 243
aaatccgcaa agaggacaga tgaacaagaa cc 32

<210> SEQ ID NO 244
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 244
ccatgttaac actaaaacac tcatgtaaaa tacgaaagac 40

<210> SEQ ID NO 245
<211> LENGTH: 35
<212> TYPE: DNA
<213> ORGANISM: Artificial Sequence
<220> FEATURE:
<223> OTHER INFORMATION: Synethetic polynucleotide

<400> SEQUENCE: 245
cttagccgga acgaggcaat catagagcct gtagc 35

<210> SEQ ID NO 246
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 246
acaccggaat cataatgggc ttaagtaatt ta 32

<210> SEQ ID NO 247
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 247
agcgcgaaga cttttttgcta cagaggcttt gaaacgtcac caatgaaa 48

<210> SEQ ID NO 248
<211> LENGTH: 32

```
<212> TYPE: DNA
<213> ORGANISM: Artificial Sequence
<220> FEATURE:
<223> OTHER INFORMATION: Synethetic polynucleotide

<400> SEQUENCE: 248
cgccatatgg actaaaacaa agtacaaaat aa                                    32

<210> SEQ ID NO 249
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 249
caaactacaa cgccggagtt tcgaggatta aagccagaat gg                         42

<210> SEQ ID NO 250
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 250
ggcagaggcc agtagcacca ttaccattag ca                                    32

<210> SEQ ID NO 251
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 251
agcatcggcg taatcagtag cgacagaatc aa                                    32

<210> SEQ ID NO 252
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 252
ctcagcagcg taatgccact acgaaggcac caaaagaggc cggttcacg                  49

<210> SEQ ID NO 253
<211> LENGTH: 35
<212> TYPE: DNA
<213> ORGANISM: Artificial Sequence
<220> FEATURE:
<223> OTHER INFORMATION: Synethetic polynucleotide

<400> SEQUENCE: 253
ttgcgggacc gatataaatt tgccatcttt tcata                                 35

<210> SEQ ID NO 254
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 254
```
caaaatcaca ttttcgagtt tattaaagcc tgaaataccg                    40

<210> SEQ ID NO 255
<211> LENGTH: 31
<212> TYPE: DNA
<213> ORGANISM: Artificial Sequence
<220> FEATURE:
<223> OTHER INFORMATION: Synethetic polynucleotide

<400> SEQUENCE: 255
attttcaggg atagctcaga gccttttcac a                             31

<210> SEQ ID NO 256
<211> LENGTH: 38
<212> TYPE: DNA
<213> ORGANISM: Artificial Sequence
<220> FEATURE:
<223> OTHER INFORMATION: Synethetic polynucleotide

<400> SEQUENCE: 256
ccatcgatag cagcacaacg agggtagcaa cgcatgag                      38

<210> SEQ ID NO 257
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 257
gtttgccttc gtcaccaaaa tcacaaaaga at                            32

<210> SEQ ID NO 258
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 258
cgcccacgca taacgacaat gaaattattc ccccggctcc                    40

<210> SEQ ID NO 259
<211> LENGTH: 39
<212> TYPE: DNA
<213> ORGANISM: Artificial Sequence
<220> FEATURE:
<223> OTHER INFORMATION: Synethetic polynucleotide

<400> SEQUENCE: 259
taccgatagt tgcgctttct taaaggcata gtcggtagc                     39

<210> SEQ ID NO 260
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 260
attatcactt gagccacagc gccaaagaca aa                            32

<210> SEQ ID NO 261
<211> LENGTH: 30
<212> TYPE: DNA
<213> ORGANISM: Artificial Sequence

```
<220> FEATURE:
<223> OTHER INFORMATION: Synethetic polynucleotide

<400> SEQUENCE: 261
tgctttcgag gtgaagcatc ggtttatcag                              30

<210> SEQ ID NO 262
<211> LENGTH: 49
<212> TYPE: DNA
<213> ORGANISM: Artificial Sequence
<220> FEATURE:
<223> OTHER INFORMATION: Synethetic polynucleotide

<400> SEQUENCE: 262
attgtatttc tgcgcaatca cgttggtgta gattaacaac caccgccac          49

<210> SEQ ID NO 263
<211> LENGTH: 29
<212> TYPE: DNA
<213> ORGANISM: Artificial Sequence
<220> FEATURE:
<223> OTHER INFORMATION: Synethetic polynucleotide

<400> SEQUENCE: 263
cgacaaggta aataggaagg tgacaatga                               29

<210> SEQ ID NO 264
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 264
caacatggtt tactttgtac cataaaggga at                           32

<210> SEQ ID NO 265
<211> LENGTH: 21
<212> TYPE: DNA
<213> ORGANISM: Artificial Sequence
<220> FEATURE:
<223> OTHER INFORMATION: Synethetic polynucleotide

<400> SEQUENCE: 265
agctaatgca gaaagcagaa t                                       21

<210> SEQ ID NO 266
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 266
aagtcctgag ccagtagtat aaagccaacg ctcaacagta tactagaa          48

<210> SEQ ID NO 267
<211> LENGTH: 30
<212> TYPE: DNA
<213> ORGANISM: Artificial Sequence
<220> FEATURE:
<223> OTHER INFORMATION: Synethetic polynucleotide

<400> SEQUENCE: 267
aataataatt ttaaccaact aaaggaattg                              30
```

<210> SEQ ID NO 268
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 268
agcgctaatt aggttgtgag aagagtcaat agattaatta                    40

<210> SEQ ID NO 269
<211> LENGTH: 31
<212> TYPE: DNA
<213> ORGANISM: Artificial Sequence
<220> FEATURE:
<223> OTHER INFORMATION: Synethetic polynucleotide

<400> SEQUENCE: 269
tgctaaacaa ctttctttc tgtgtaagag c                              31

<210> SEQ ID NO 270
<211> LENGTH: 21
<212> TYPE: DNA
<213> ORGANISM: Artificial Sequence
<220> FEATURE:
<223> OTHER INFORMATION: Synethetic polynucleotide

<400> SEQUENCE: 270
ttacgcatgg gagggaataa a                                        21

<210> SEQ ID NO 271
<211> LENGTH: 28
<212> TYPE: DNA
<213> ORGANISM: Artificial Sequence
<220> FEATURE:
<223> OTHER INFORMATION: Synethetic polynucleotide

<400> SEQUENCE: 271
cgttagtaaa tgaactctgt cgtctttc                                 28

<210> SEQ ID NO 272
<211> LENGTH: 43
<212> TYPE: DNA
<213> ORGANISM: Artificial Sequence
<220> FEATURE:
<223> OTHER INFORMATION: Synethetic polynucleotide

<400> SEQUENCE: 272
taaagtttag acgtcggata attgtaaacg ttaattataa gca                43

<210> SEQ ID NO 273
<211> LENGTH: 21
<212> TYPE: DNA
<213> ORGANISM: Artificial Sequence
<220> FEATURE:
<223> OTHER INFORMATION: Synethetic polynucleotide

<400> SEQUENCE: 273
gctgtctttc cttcaaagca t                                        21

<210> SEQ ID NO 274
<211> LENGTH: 22
<212> TYPE: DNA
<213> ORGANISM: Artificial Sequence
<220> FEATURE:
<223> OTHER INFORMATION: Synethetic polynucleotide

<400> SEQUENCE: 274
cagagccacc accctcacga tc										22

<210> SEQ ID NO 275
<211> LENGTH: 42
<212> TYPE: DNA
<213> ORGANISM: Artificial Sequence
<220> FEATURE:
<223> OTHER INFORMATION: Synethetic polynucleotide

<400> SEQUENCE: 275
ttaaaccaag tacgaactaa tccatcacga attcatatgt tc							42

<210> SEQ ID NO 276
<211> LENGTH: 38
<212> TYPE: DNA
<213> ORGANISM: Artificial Sequence
<220> FEATURE:
<223> OTHER INFORMATION: Synethetic polynucleotide

<400> SEQUENCE: 276
taccgcgccc aataacaaga aatggtttgt ttagtatc							38

<210> SEQ ID NO 277
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 277
aaagaacttt catcttgctg atgcaaatcc aacctccggc							40

<210> SEQ ID NO 278
<211> LENGTH: 21
<212> TYPE: DNA
<213> ORGANISM: Artificial Sequence
<220> FEATURE:
<223> OTHER INFORMATION: Synethetic polynucleotide

<400> SEQUENCE: 278
cccagaacaa taagaggcgg g										21

<210> SEQ ID NO 279
<211> LENGTH: 21
<212> TYPE: DNA
<213> ORGANISM: Artificial Sequence
<220> FEATURE:
<223> OTHER INFORMATION: Synethetic polynucleotide

<400> SEQUENCE: 279
aatcagaatc gtaggaatca t										21

<210> SEQ ID NO 280
<211> LENGTH: 31
<212> TYPE: DNA
<213> ORGANISM: Artificial Sequence
<220> FEATURE:
<223> OTHER INFORMATION: Synethetic polynucleotide

<400> SEQUENCE: 280
atgtaccgta acactaagcc caagtaataa a								31

<210> SEQ ID NO 281

```
<210> SEQ ID NO 281
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 281
caagagaagg attaggagag gctgagactc ct                                  32

<210> SEQ ID NO 282
<211> LENGTH: 43
<212> TYPE: DNA
<213> ORGANISM: Artificial Sequence
<220> FEATURE:
<223> OTHER INFORMATION: Synethetic polynucleotide

<400> SEQUENCE: 282
agaaggcaca tcgagacgtt tttatttgat taagactcct tat                      43

<210> SEQ ID NO 283
<211> LENGTH: 21
<212> TYPE: DNA
<213> ORGANISM: Artificial Sequence
<220> FEATURE:
<223> OTHER INFORMATION: Synethetic polynucleotide

<400> SEQUENCE: 283
tccggaaccc aagaacgggt a                                              21

<210> SEQ ID NO 284
<211> LENGTH: 38
<212> TYPE: DNA
<213> ORGANISM: Artificial Sequence
<220> FEATURE:
<223> OTHER INFORMATION: Synethetic polynucleotide

<400> SEQUENCE: 284
cagaaccgcc acccggccag aaaccctctt aatattta                            38

<210> SEQ ID NO 285
<211> LENGTH: 21
<212> TYPE: DNA
<213> ORGANISM: Artificial Sequence
<220> FEATURE:
<223> OTHER INFORMATION: Synethetic polynucleotide

<400> SEQUENCE: 285
cgaactaagc agaggatatt c                                              21

<210> SEQ ID NO 286
<211> LENGTH: 21
<212> TYPE: DNA
<213> ORGANISM: Artificial Sequence
<220> FEATURE:
<223> OTHER INFORMATION: Synethetic polynucleotide

<400> SEQUENCE: 286
aggttcacaa gaaacggata t                                              21

<210> SEQ ID NO 287
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 287
```
gccttaaatc aagagcaagc aatgtaaatc tgacctaaat         40

<210> SEQ ID NO 288
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 288
tcggaggaag ctattttaaa aattttaga accctcatat aaatcggt         48

<210> SEQ ID NO 289
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 289
aaagcgcagt cagtagtaac gaactaacgg aacaacatta         40

<210> SEQ ID NO 290
<211> LENGTH: 30
<212> TYPE: DNA
<213> ORGANISM: Artificial Sequence
<220> FEATURE:
<223> OTHER INFORMATION: Synethetic polynucleotide

<400> SEQUENCE: 290
ttgatataag tagaaaagtg ccgtcgagag         30

<210> SEQ ID NO 291
<211> LENGTH: 21
<212> TYPE: DNA
<213> ORGANISM: Artificial Sequence
<220> FEATURE:
<223> OTHER INFORMATION: Synethetic polynucleotide

<400> SEQUENCE: 291
ctattgggag ataaccttga a         21

<210> SEQ ID NO 292
<211> LENGTH: 30
<212> TYPE: DNA
<213> ORGANISM: Artificial Sequence
<220> FEATURE:
<223> OTHER INFORMATION: Synethetic polynucleotide

<400> SEQUENCE: 292
cagtaccagg cggatattag cggggttttg         30

<210> SEQ ID NO 293
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 293
cagagagatt ggattaaaaa cagaaataaa gagaatatac caaaaatg         48

<210> SEQ ID NO 294
<211> LENGTH: 27
<212> TYPE: DNA

<213> ORGANISM: Artificial Sequence
<220> FEATURE:
<223> OTHER INFORMATION: Synethetic polynucleotide

<400> SEQUENCE: 294
aataaagtta taatgctgtt tagctat    27

<210> SEQ ID NO 295
<211> LENGTH: 43
<212> TYPE: DNA
<213> ORGANISM: Artificial Sequence
<220> FEATURE:
<223> OTHER INFORMATION: Synethetic polynucleotide

<400> SEQUENCE: 295
attttctgaa gaaaagcaag aaacaatgaa atagcaatag cta    43

<210> SEQ ID NO 296
<211> LENGTH: 30
<212> TYPE: DNA
<213> ORGANISM: Artificial Sequence
<220> FEATURE:
<223> OTHER INFORMATION: Synethetic polynucleotide

<400> SEQUENCE: 296
aacatgaaag tattaacaac ctattattct    30

<210> SEQ ID NO 297
<211> LENGTH: 32
<212> TYPE: DNA
<213> ORGANISM: Artificial Sequence
<220> FEATURE:
<223> OTHER INFORMATION: Synethetic polynucleotide

<400> SEQUENCE: 297
ttagacggca ttttgcgatg atggcaattc at    32

<210> SEQ ID NO 298
<211> LENGTH: 40
<212> TYPE: DNA
<213> ORGANISM: Artificial Sequence
<220> FEATURE:
<223> OTHER INFORMATION: Synethetic polynucleotide

<400> SEQUENCE: 298
caaaataaac agcattagtt gtaagacgcg gttatataac    40

<210> SEQ ID NO 299
<211> LENGTH: 24
<212> TYPE: DNA
<213> ORGANISM: Artificial Sequence
<220> FEATURE:
<223> OTHER INFORMATION: Synethetic polynucleotide

<400> SEQUENCE: 299
gtgtactgtt catttgaaac atta    24

<210> SEQ ID NO 300
<211> LENGTH: 27
<212> TYPE: DNA
<213> ORGANISM: Artificial Sequence
<220> FEATURE:
<223> OTHER INFORMATION: Synethetic polynucleotide

<400> SEQUENCE: 300
aacgggccag aggaaggctt aattgct    27

-continued

<210> SEQ ID NO 301
<211> LENGTH: 21
<212> TYPE: DNA
<213> ORGANISM: Artificial Sequence
<220> FEATURE:
<223> OTHER INFORMATION: Synethetic polynucleotide

<400> SEQUENCE: 301
ttgccaagaa acgagattgc a                                      21

<210> SEQ ID NO 302
<211> LENGTH: 37
<212> TYPE: DNA
<213> ORGANISM: Artificial Sequence
<220> FEATURE:
<223> OTHER INFORMATION: Synethetic polynucleotide

<400> SEQUENCE: 302
tttaacgtag taacagaagt tacaaaatcg cgcagag                     37

<210> SEQ ID NO 303
<211> LENGTH: 37
<212> TYPE: DNA
<213> ORGANISM: Artificial Sequence
<220> FEATURE:
<223> OTHER INFORMATION: Synethetic polynucleotide

<400> SEQUENCE: 303
ttatcccatt caattattaa caatttcatt tgaatta                     37

<210> SEQ ID NO 304
<211> LENGTH: 48
<212> TYPE: DNA
<213> ORGANISM: Artificial Sequence
<220> FEATURE:
<223> OTHER INFORMATION: Synethetic polynucleotide

<400> SEQUENCE: 304
catattatat tttcccaaac agtacataaa tcaatatatg acaaaatt         48

<210> SEQ ID NO 305
<211> LENGTH: 31
<212> TYPE: DNA
<213> ORGANISM: Artificial Sequence
<220> FEATURE:
<223> OTHER INFORMATION: Synethetic polynucleotide

<400> SEQUENCE: 305
gagaatagaa aggaaaacag tttctcccag a                           31

<210> SEQ ID NO 306
<211> LENGTH: 26
<212> TYPE: DNA
<213> ORGANISM: Artificial Sequence
<220> FEATURE:
<223> OTHER INFORMATION: Synethetic polynucleotide

<400> SEQUENCE: 306
gtaataaaag ggagttgggt aacgcc                                 26

<210> SEQ ID NO 307
<211> LENGTH: 27
<212> TYPE: DNA
<213> ORGANISM: Artificial Sequence
<220> FEATURE:

<223> OTHER INFORMATION: Synethetic polynucleotide key "ab"

<400> SEQUENCE: 307
ccttctaacc tccctctcta ctatcta                                              27

<210> SEQ ID NO 308
<211> LENGTH: 50
<212> TYPE: DNA
<213> ORGANISM: Artificial Sequence
<220> FEATURE:
<223> OTHER INFORMATION: Synethetic polynucleotide lock sequence 1

<400> SEQUENCE: 308
cagcggtggt gtcactgcgc gcctccccgg ccttctaacc tccctctcta                     50

<210> SEQ ID NO 309
<211> LENGTH: 69
<212> TYPE: DNA
<213> ORGANISM: Artificial Sequence
<220> FEATURE:
<223> OTHER INFORMATION: Synethetic polynucleotide lock sequence 2

<400> SEQUENCE: 309
tagatagtag agagggaggt tagaagggaa gtttccatta aacggctttg accccagcg          60 attgtgtcg                                                                  69

<210> SEQ ID NO 310
<211> LENGTH: 74
<212> TYPE: DNA
<213> ORGANISM: Artificial Sequence
<220> FEATURE:
<223> OTHER INFORMATION: Synethetic polynucleotide key "cd"

<400> SEQUENCE: 310
accacacaca acctccacaa aacccaattt ttttttttg tagcaatact ttaaagggat           60
tttagactaa acag                                                            74

<210> SEQ ID NO 311
<211> LENGTH: 22
<212> TYPE: DNA
<213> ORGANISM: Artificial Sequence
<220> FEATURE:
<223> OTHER INFORMATION: Synethetic polynucleotide strand 1

<400> SEQUENCE: 311
caagactcga ctagtgcgag tc                                                   22

<210> SEQ ID NO 312
<211> LENGTH: 65
<212> TYPE: DNA
<213> ORGANISM: Artificial Sequence
<220> FEATURE:
<223> OTHER INFORMATION: Synethetic polynucleotide strand 2

<400> SEQUENCE: 312
ctatcttaac ctccctctct agcactagtc gagtcttgag agctcgtagc tagtgtaagc          60
gactc                                                                      65

<210> SEQ ID NO 313
<211> LENGTH: 44
<212> TYPE: DNA
<213> ORGANISM: Artificial Sequence
<220> FEATURE:
<223> OTHER INFORMATION: Synethetic polynucleotide strand 3

```
<400> SEQUENCE: 313
gctacgagct cctatgtctc gaatgctagc agcagcttac acta                      44

<210> SEQ ID NO 314
<211> LENGTH: 66
<212> TYPE: DNA
<213> ORGANISM: Artificial Sequence
<220> FEATURE:
<223> OTHER INFORMATION: Synethetic polynucleotide strand 4

<400> SEQUENCE: 314
agacatagct agactactga cgtacatcgc tctagcattc agttaaccca cgccgaatcc      60
tagact                                                                66

<210> SEQ ID NO 315
<211> LENGTH: 59
<212> TYPE: DNA
<213> ORGANISM: Artificial Sequence
<220> FEATURE:
<223> OTHER INFORMATION: Synethetic polynucleotide strand 5

<400> SEQUENCE: 315
gatcaggcga tgtacgtcag tagtctagga cgtcgtctag aacttagaga gggaggtta       59

<210> SEQ ID NO 316
<211> LENGTH: 22
<212> TYPE: DNA
<213> ORGANISM: Artificial Sequence
<220> FEATURE:
<223> OTHER INFORMATION: Synethetic polynucleotide strand 6

<400> SEQUENCE: 316
ctgatcagtt ctagacgacg tc                                              22

<210> SEQ ID NO 317
<211> LENGTH: 21
<212> TYPE: DNA
<213> ORGANISM: Artificial Sequence
<220> FEATURE:
<223> OTHER INFORMATION: Synethetic polynucleotide key

<400> SEQUENCE: 317
tagagaggga ggttaagata g                                               21
```

SPATIAL SEQUESTRATION OF DYNAMIC NUCLEIC ACID CIRCUITS

RELATED APPLICATIONS

This application is a national stage filing under 35 U.S.C. §371 of International Application No. PCT/US2012/036193 filed May 2, 2012, which was published under PCT Article 21(2) in English, and which claims the benefit of U.S. Provisional Application Ser. No. 61/481,542, filed on May 2, 2011, entitled "SPATIAL SEQUESTRATION OF DYNAMIC NUCLEIC ACID CIRCUITS", the entire contents of each of which are incorporated by reference herein.

GOVERNMENT SUPPORT

This invention was made with Government support under National Institutes of Health award 1DP2OD007292-01 and Office of Naval Research/NESEC award N00014-10-1-0827. The Government has certain rights in the invention.

BACKGROUND OF INVENTION

The self-assembly of DNA nanostructures has become an integral part of nanotechnology. Unlike other materials, such as carbon nanotubes and quantum dots, nucleic acids offer addressability at the nanometer scale, and thus have been used to the facilitate addressable patterning of a wide variety of other nanomaterials. In particular, one DNA nanotechnology approach, known as DNA origami, has risen to the forefront due to its reliability, simplicity, scale, addressability, and low cost.

SUMMARY OF INVENTION

The invention provides methods for spatial sequestering elements, including nucleic acids and various types of agents, that may be used in nucleic acid circuits. Such circuits may be used to control release of agents temporally or spatially in vivo or in other environments.

In one aspect, the invention provides a system comprising a first nucleic acid nanostructure comprising, attached to its interior surface, a first tethered nucleic acid, and a second nucleic acid nanostructure comprising, attached to its interior surface, a second tethered nucleic acid, wherein the first nucleic acid is partially hybridized to a first output signal nucleic acid that is capable of partial hybridization to the second tethered nucleic acid.

In some embodiments, the second tethered nucleic acid is partially hybridized to a second output signal nucleic acid. In some embodiments, the first and second tethered nucleic acids are not integral to the first and second nucleic acid nanostructures. For example, they may not be required in the formation of the nanostructures.

In some embodiments, the first and second nucleic acid nanostructures are independently selected from the group consisting of closed nucleic acid nanostructures and open nucleic acid nanostructures. In some embodiments, the open nucleic acid nanostructures comprise two open ends. In some embodiments, the closed nucleic acid nanostructures comprise a nucleic acid lock.

In some embodiments, the system further comprises one or more upstream and/or downstream nucleic acid nanostructures. In some embodiments, the one or more of the upstream and/or downstream nucleic acid nanostructures comprise a tethered nucleic acid. In some embodiments, the one or more of the upstream and/or downstream nucleic acid nanostructures comprise free flowing nucleic acids. In some embodiments, the free flowing nucleic acids are output signal nucleic acids.

In some embodiments, one or more of the nucleic acid nanostructures comprise an agent.

In some embodiments, the agent is or comprises a therapeutic agent or a detectable marker.

In some embodiments, one or more nucleic acid nanostructures comprise a plurality of tethered nucleic acids and/or a plurality of free flowing nucleic acids. In some embodiments, (a) the plurality of tethered nucleic acids is homogeneous, (b) the plurality of tethered nucleic acids is heterogeneous, (c) the plurality of free flowing nucleic acids is homogeneous, and/or (d) the plurality of free flowing nucleic acids is heterogeneous.

In another aspect, the invention provides a method comprising contacting a first input nucleic acid with any of the foregoing systems in an amount effective to release the second output signal nucleic acid from the second nucleic acid nanostructure.

In another aspect, the invention provides a system comprising a first nucleic acid nanostructure comprising, attached to its interior surface, a first tethered nucleic acid, and a second nucleic acid nanostructure comprising (a) a second tethered nucleic acid attached to its exterior surface and (b) an agent in its interior, wherein the first nucleic acid is partially hybridized to a first output signal nucleic acid that is capable of partial hybridization to the second tethered nucleic acid, and wherein the second nucleic acid nanostructure is a closed nanostructure.

In another aspect, the invention provides a method comprising contacting a first input nucleic acid with the system of claim B1 in an amount effective to release agent from the second nucleic acid nanostructure.

In another aspect, the invention provides a system comprising a first nucleic acid nanostructure comprising, attached to its interior surface, a first tethered nucleic acid and a second tethered nucleic acid that are partially hybridized to each other, and a second nucleic acid nanostructure comprising, attached to its interior surface, a third tethered nucleic acid that is partially hybridized to a first output signal nucleic acid, wherein the second and third tethered nucleic acids can partially hybridize to each other thereby releasing the first output signal nucleic acid. In another aspect, the invention provides a method comprising contacting a first input nucleic acid with the foregoing system in an amount effective to release agent from the second nucleic acid nanostructure.

In another aspect, the invention provides a system comprising a first nucleic acid nanostructure comprising, attached to its interior surface, a first tethered nucleic acid, and a second nucleic acid nanostructure comprising, attached to its interior surface, a second tethered nucleic acid that is partially hybridized to a third nucleic acid, wherein the first tethered nucleic acid and third nucleic acids can hybridize to each other thereby releasing the third nucleic acid from the second tethered nucleic acid. In some embodiments, the first nucleic acid nanostructure can be positioned partially or completely within the second nucleic acid nanostructure.

In another aspect, the invention provides a system comprising a first closed nucleic acid nanostructure comprising, in its interior, a plurality of first nucleic acids, a second closed nucleic acid nanostructure comprising, in its interior, a plurality of second nucleic acids, wherein the plurality of first nucleic acids, once released, functions to open the second closed nucleic acid nanostructure. In some embodiments, the system comprises a plurality of first closed nucleic acid nanostructures and a plurality of second closed nucleic acid nanostructures. In some embodiments, each of the pluralities is homogeneous. In some embodiments, the system further comprises one or more upstream and/or downstream closed nucleic acid nanostructures. In some embodiments, one or more nucleic acid nanostructures comprise an agent. In some embodiments, the agent is or comprises a therapeutic agent or a detectable marker. In some embodiments, the first and second nucleic acids are in free flow. In some embodiments, the first nucleic acids are nucleic acid keys for the second closed nucleic acid nanostructure. In another aspect, the invention provides a method comprising contacting a first input nucleic acid with any of the foregoing systems in an amount effective to release the plurality of second nucleic acids from the second closed nucleic acid nanostructures.

In another aspect, the invention provides a system comprising a first closed nucleic acid nanostructure comprising a first internally tethered nucleic acid, and a second closed nucleic acid nanostructure comprising a second internally tethered nucleic acid and a second externally tethered nucleic acid, wherein, once the first closed nucleic acid nanostructure is opened, the first internally tethered nucleic acid is able to hybridize to the second externally tethered nucleic acid, thereby opening the second closed nucleic acid nanostructure and tethering the first and second nucleic acid nanostructures to each other. In another aspect, the invention provides a method comprising contacting a first input signal nucleic acid with the foregoing system in an amount effective to tether the first and second nucleic acid nanostructures to each other. In some embodiments, the first input signal nucleic acid is tethered to a solid support that is not in free flow.

In another aspect, the invention provides a system comprising a first nucleic acid nanostructure comprising, attached to its interior surface, a first tethered nucleic acid and a second tethered nucleic acid that are partially hybridized to each other, and a second nucleic acid nanostructure comprising, attached to its interior surface, a third tethered nucleic acid and a fourth tethered nucleic acid that are partially hybridized to each other, wherein the second and third tethered nucleic acids can partially hybridize to each other thereby aggregating the first and second nanostructures to each other. In another aspect, the invention provides a method comprising contacting a first input signal nucleic acid with the foregoing system in an amount effective to tether the first and second nucleic acid nanostructures to each other.

These and other aspects and embodiments of the invention will be described in greater detail herein.

Figure 1:
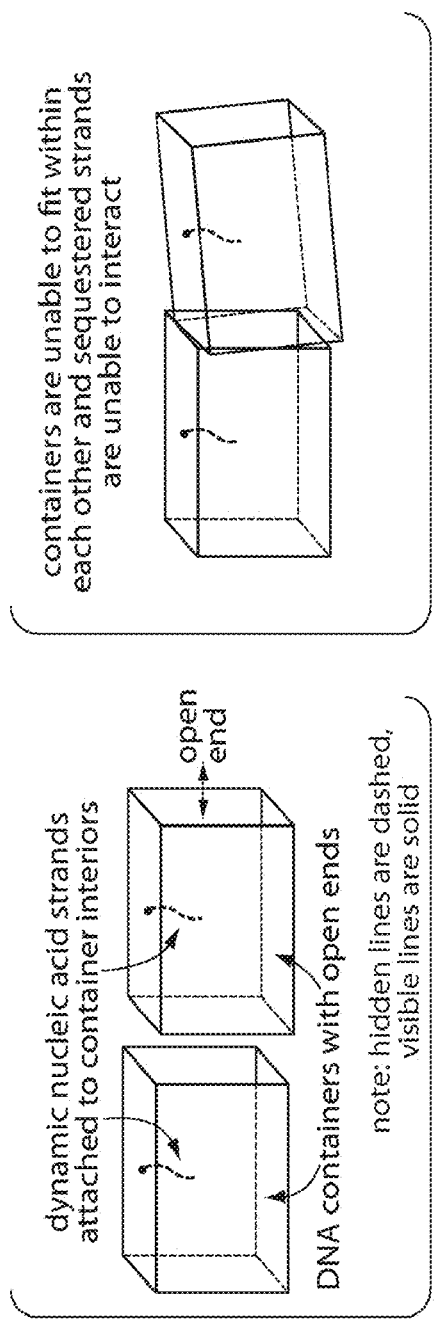
FIG. 1: (left) Open-ended, three-dimensional containers sequestering potentially-interacting nucleic acid strands within them. (right) Strands are unable to interact while bound.

The Sequence Listing provided herewith is considered part of the application and is incorporated by reference herein.

DETAILED DESCRIPTION OF INVENTION

The invention relates broadly to the novel and inventive compositions, articles of manufacture, and methods of use thereof for controlling dynamic nucleic acid (e.g., DNA) circuits via the spatial sequestration of nucleic acid signaling components. Sequestration methods consist of holding critical circuit elements within more complex, rigid nucleic acid (e.g., DNA) structures, with shapes ranging from small tiles to full-fledged nucleic acid "origami" structures such as enclosed boxes. Applications include but are not limited to (a) the concentration or separation of incorporated signals so as to drive or isolate signaling reactions, (b) the amplification of a response by the triggered release of many copies of pre-prepared components, and (c) the triggered aggregation of these structures and any associated contents.

The field of DNA nanotechnology can be broadly separated into two subfields, one concerning control over the structural assembly of nucleic acid components[1], and another focusing on the dynamic interaction of systems of oligonucleotides[2]. It is possible to isolate from interaction key components of the latter, dynamic systems by placing them within loops of "hairpin-" shaped oligonucleotides or within double-stranded portions. This typically results in an incomplete level of isolation, as the thermal motion driving all chemical reactions itself perturbs the isolation and causes signal "leakage." The combination of elements from the structural and dynamic areas of the field, as provided by the invention, allows for the isolation of key dynamic components by physically, or spatially, sequestering them within the structural components. Spatial sequestration may be carried out by isolation within hollow structures[3], by a more steric approach in which small tiles[1] cover the isolated signal, or even in open structures (e.g., boxes without one or two sides) that prevent interaction of signals tethered within them. These approaches allow for a broad variety of applications that take advantage of the complex signal separation, the signal amplification that can be achieved by sudden release of prepared components, and/or the incorporation of the structures themselves for the intended effect. Importantly, the effect of one structure (and/or its contents) on another can be linked in a cascading fashion, for example to amplify a signal by multiple serial stages of strand release.

The structural components of the invention may take any form or shape as the invention is not limited in this respect unless otherwise stated. Accordingly, the terms "container" or "structure" are used throughout to denote the structural component of the invention. The structural component is that component which physically sequesters dynamic components of the system (e.g., input signals, output signals and the like). In some instances, the structure may be capable of physically sequestering or retaining an agent such as a nucleic acid even in the absence of tethering. In other instances, the structure may require that the agent be tethered in order to be sequestered or retained. Some of the embodiments described herein refer to containers such as boxes or tubes, which can be closed, or which can have one open end or two open ends. In still other instances, the nucleic acid structures are tile-shaped (or book-shaped; for example, the nanostructure is essentially planar with a hinge such that it is able to fold over on itself) and capable of folding together to shield or hide or otherwise physically sequester dynamic nucleic acid components. These latter nanostructures can also adopt open (e.g., flat or unfolded) or closed (e.g., folded and optionally locked) configurations according to the invention. In these configurations, the nucleic acids are typically accessible to the external environment and available for interaction with for example other nucleic acids. It is to be understood that the invention may be carried out using a variety of shapes and forms provided their structure is suitable for the application contemplated.

These containers may be referred to herein as "nucleic acid nanostructures" because their dimensions are typically in the nanometer range (typically 3-100 nm). The invention further contemplates the use of structures of varying sizes. Thus, in some embodiments, the nucleic acid structures employed in a system may be of about the same size or they may be of significantly different sizes such that some structures can be positioned partially or fully within other structures, as shown for example in FIG. 4.

Containers are typically constructed using the DNA "origami" method, wherein a long "scaffold" DNA strand "rasterizes" a target structure shape, while many short "staple"

strands hybridize to the scaffold and hold it in the target shape. The invention includes this method, but also other methods of constructing structures using similar polymers. For example, the "single-stranded tile" method has been used to construct similar structures [Yin et al., Nature 2008].

Structural and dynamic components of the invention are typically nucleic acid in nature. Many of the embodiments of the invention described herein refer to structural or dynamic components as DNA in nature. It is to be understood however that this is merely for the sake of convenience and brevity and that the invention contemplates a broader range of nucleic acid as now described. Nucleic acids, in the context of the invention, include DNA and RNA, as well are various modifications thereof. Modifications include base modifications, sugar modifications, and backbone modifications. Non-limiting examples of these are provided below. Non-limiting examples of DNA variants that may be used in the invention are L-DNA (the backbone enantiomer of DNA, known in the literature), peptide nucleic acids (PNA) bisPNA clamp, a pseudocomplementary PNA, a locked nucleic acid (LNA), or co-nucleic acids of the above such as DNA-LNA co-nucleic acids. It is to be understood that the nucleic acids used in the structural and dynamic components of the invention may be homogeneous or heterogeneous in nature. As an example, they may be completely DNA in nature or they may be comprised of DNA and non-DNA (e.g., LNA) monomers or sequences. Thus, any combination of nucleic acid elements may be used. The nucleic acids of the invention may be referred to as polymers or nucleic acid polymers. The modification may render the interactions of such polymers more or less stable under certain conditions.

The nucleic acids of the invention may be obtained from natural sources, and optionally subsequently modified. They may be synthesized in vitro, and optionally may mimic a naturally occurring nucleic acid or may represent a non-naturally occurring nucleic acid (e.g., due to the present of elements that are not found in naturally occurring nucleic acids). Methods for harvesting nucleic acids from in cells, tissues or organisms are known in the art. Methods for synthesizing nucleic acids, including automated nucleic acid synthesis, are also known in the art.

The nucleic acids may have a homogenous backbone (e.g., entirely phosphodiester or entirely phosphorothioate) or a heterogeneous (or chimeric) backbone. Phosphorothioate backbone modifications render a nucleic acid less susceptible to nucleases and thus more stable (as compared to a native phosphodiester backbone nucleic acid) under certain conditions. Other linkages that may provide more stability to a nucleic acid include without limitation phosphorodithioate linkages, methylphosphonate linkages, methylphosphorothioate linkages, boranophosphonate linkages, peptide linkages, alkyl linkages, dephospho type linkages, and the like.

Nucleic acids having modified backbones, such as backbones comprising phosphorothioate linkages, and including those comprising chimeric modified backbones may be synthesized using automated techniques employing either phosphoramidate or H-phosphonate chemistries. (F. E. Eckstein, "Oligonucleotides and Analogues—A Practical Approach" IRL Press, Oxford, UK, 1991, and M. D. Matteucci and M. H. Caruthers, *Tetrahedron Lett.* 21, 719 (1980)) Aryl- and alkyl-phosphonate linkages can be made, e.g., as described in U.S. Pat. No. 4,469,863; and alkylphosphotriester linkages (in which the charged oxygen moiety is alkylated), e.g., as described in U.S. Pat. No. 5,023,243 and European Patent No. 092,574, can be prepared by automated solid phase synthesis using commercially available reagents. Methods for making other DNA backbone modifications and substitutions have been described. Uhlmann E et al. (1990) Chem Rev 90:544; Goodchild J (1990) Bioconjugate Chem 1:165; Crooke S T et al. (1996) Annu Rev Pharmacol Toxicol 36:107-129; and Hunziker J et al. (1995) Mod Synth Methods 7:331-417.

The nucleic acids of the invention may additionally or alternatively comprise modifications in their sugars. For example, a β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, arabinose, 2'-F-arabinose, 2'-O—($C_1$-$C_6$)alkyl-ribose, preferably 2'-O—($C_1$-$C_6$)alkyl-ribose is 2'-O-methylribose, 2'-O—($C_2$-$C_6$)alkenyl-ribose, 2'-[O—($C_1$-$C_6$)alkyl-O—($C_1$-$C_6$)alkyl]-ribose, 2'-$NH_2$-2'-deoxyribose, β-D-xylo-furanose, α-arabinofuranose, 2,4-dideoxy-β-D-erythro-hexo-pyranose, and carbocyclic (described, for example, in Froehler J (1992) Am Chem Soc 114:8320) and/or open-chain sugar analogs (described, for example, in Vandendriessche et al. (1993) Tetrahedron 49:7223) and/or bicyclosugar analogs (described, for example, in Tarkov M et al. (1993) Helv Chim Acta 76:481).

The nucleic acids may comprise modifications in their bases. Modified based include modified cytosines (such as 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluorouracil, 5-bromo-uracil, 5-bromovinyl-uracil, 4-thiouracil, 5-hydroxy-uracil, 5-propynyl-uracil), modified guanines such as 7-deazaguanine, 7-deaza-7-substituted guanine (such as 7-deaza-7-(C2-C6)alkynylguanine), 7-deaza-8-substituted guanine, hypoxanthine, N2-substituted guanines (e.g. N2-methyl-guanine), 5-amino-3-methyl-3H, 6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. The nucleic acids may comprise universal bases (e.g. 3-nitropyrrole, P-base, 4-methyl-indole, 5-nitro-indole, and K-base) and/or aromatic ring systems (e.g. fluorobenzene, difluorobenzene, benzimidazole or dichlorobenzimidazole, 1-methyl-1H-[1,2,4]triazole-3-carboxylic acid amide).

As used herein, the terms "bind" or "interact" as they relate to nucleic acids typically refer to hybridization (e.g., base-specific binding) between two or more nucleic acid sequences or strands. The term "annealing" refers to the process of heating and slowly cooling a mixture of nucleic acids (e.g., in a typical thermal cycling machine) such that the thermodynamic steady state (or one relatively near it) of hybridized elements is formed. Interaction between nucleic acids, according to the invention, is specific and is typically governed by the sequence of the interacting strands. These interactions include Watson-Crick binding in which complementary nucleic acid sequences hybridize to each other. These interactions may also include other binding motifs including but not limited to Hoogsteen or quadruplex binding.

The compositions and methods of the invention can be used in vitro and/or in vivo. When used in vivo, they may be administered to a subject. The subject may be a human or non-human subject. Non-human subjects include laboratory subjects such as rats, mice, primates, rabbits, etc., companion subjects such as dogs and cats, agricultural livestock such as cows, pigs, sheep, etc., prized subjects such as thoroughbred horses, fish and other aquatic species, etc.

When administered to a subject, the compositions of the invention may be administered by any route. Administration may result in systemic delivery or in localized delivery of the compositions. Some embodiments of the invention contemplate administering all components using the same route, whether that route is yields systemic or local delivery. Other embodiments contemplate localized delivery of one or more components of the invention and systemic delivery of one or more components of the invention. Systemic routes include oral routes and parenteral routes such as intravenous, intraperitoneal, intramuscular, subcutaneous, and the like.

The invention contemplates substantially simultaneous administration of all components. Substantially simultaneous administration of components means that the components are either administered together or they are administered separately but close in time (e.g., in the time it would take a medical practitioner to administer two sequential medicaments to a subject). The invention further contemplates staggered administration of components. As an example, the invention contemplates that one or more components may be administered at t=0 and one or more components may be administered hours, days, weeks, months or years thereafter. The later-administered components may be input signals, as described in greater detail herein, or they may be inhibitory or "stop" signals that may be used to stop a cascade or reaction that is occurring in the subject. It is to be understood that the invention similarly contemplates substantially simultaneous or staggered addition of components when they are used in an in vitro setting.

The invention contemplates that the structural components of the invention typically, at a minimum, enclose and protect dynamic nucleic acid signaling components. These dynamic nucleic acid signaling components include but are not limited to tethered nucleic acids (i.e., nucleic acids that are attached to the nucleic acid container), output signal nucleic acids (e.g., nucleic acids that are hybridized to the tethered nucleic acids or free flowing nucleic acids that will be released once a closed container is "unlocked"), input signal nucleic acids (e.g., nucleic acids that flow into the nucleic acid container and displace output signal nucleic acids from the tethered nucleic acid, inhibitory or stop nucleic acid signals (e.g., free flowing nucleic acids that may be released to control the level of signal amplification or to inhibit an adverse reaction in a subject), and the like. It is to be understood that a nucleic acid container may comprise a single tethered nucleic acid, or a plurality of tethered nucleic acids, and such plurality may be homogeneous or heterogeneous. The tethered nucleic acids that function as dynamic components of the invention are to be distinguished from the nucleic acids that form the container itself. To this end, the tethered nucleic acids are not integral to the container (i.e., the container may still form even in the absence of such tethered nucleic acids). The tethered nucleic acids may be attached to pre-formed nucleic acid containers. In some instances, however, these tethered nucleic acids may be integrated into the nucleic acid container during its synthesis (even though they are not required for its formation).

As will be described in greater detail below, in some instances, certain nucleic acids may be tethered to the nucleic acid container and may still act as output signal nucleic acids provided they are able to interact with nucleic acids tethered to a separate container. Tethered nucleic acids may be attached to an interior and/or an exterior surface of the nucleic acid container. If attached to the exterior surface, such tethered nucleic acids may function as locks to keep the nucleic acid container closed, as described herein. As an example, certain nucleic acid containers may comprise two partially complementary nucleic acid strands, typically attached to an exterior surface of the container in close proximity to each other, which when hybridized to each other function to close the container. As with other of the dynamic nucleic acids of the invention, the strands are designed to have only partial complementarity, with one strand also comprising a toehold region or domain that remains single stranded and thus accessible for binding to an input signal nucleic acid strand.

As described herein, many of the dynamic nucleic acid components of the invention comprise a toehold. As used herein, a toehold is a nucleic acid sequence or domain that is used, inter alia, to bind input signal or release output signals. The systems of the invention are designed so that toeholds are single stranded and accessible for binding to incoming input signals. Accordingly, the toehold sequence has no or limited self-complementarity in it (to prevent hairpin formation and the like that would interfere with binding to input signals). The toehold sequence is not otherwise limited. The toehold sequence may be of any length, provided it is able to bind to an input signal and act as an anchor sequence for displacement of an output signal. Toeholds are typically 4-12 nucleotides in length, although they may be shorter or longer under certain conditions.

In addition to the dynamic nucleic acid components described herein, the nucleic acid containers may also comprise other components or agents. These agents may be virtually any molecule or compound. Examples include readout markers such as fluorophores or fluorophore labeled molecules or compounds, chromophores or chromophore labeled molecules or compounds, and the like; functional molecules and compounds such as therapeutic agents, specifically including the use of nucleic acids acting to perturb mRNA or protein expression, as in RNA interference ("RNAi"), antisense RNA, or other such techniques; and the like.

The invention contemplates delivery, including sustained delivery or temporally controlled delivery, of agents in vitro or in vivo. In vivo or in vitro, delivery may be to regions, tissues or cells. Agents used in vivo include any atom, molecule or compound that can provide benefit to a subject (including without limitation prophylactic or therapeutic benefit) or that can be used for diagnosis and/or detection (for example, imaging) in vivo. Agents also include any atom, molecule or compound that has use in in vitro applications.

Any agent may be delivered using the systems of the invention (including pharmaceutical compositions comprising such systems and/or their components) provided that it can be incorporated into the nucleic acid structures of such systems either during or after the synthesis of the structures. For example, the agent must be able to withstand the synthesis and optionally storage process for these structures. The agents, if incorporated into the structures during synthesis, should be stable during storage procedures and times.

The agent may be without limitation a protein, a polypeptide, a peptide, a nucleic acid, a small molecule (e.g., chemical, whether organic or inorganic) drug, a virus-like particle, a steroid, a proteoglycan, a lipid, a carbohydrate, and analogs, derivatives, mixtures, fusions, combinations or conjugates thereof. The agent may be a prodrug that is metabolized and thus converted in vivo to its active (and/or stable) form.

The agent may be naturally occurring or non-naturally occurring. Naturally occurring agents include those capable of being synthesized by the subjects to whom the agents are administered. Non-naturally occurring are those that do not exist in nature normally, whether produced by plant, animal, microbe or other living organism.

One class of agents is peptide-based agents such as (single or multi-chain) proteins and peptides. Examples include antibodies, single chain antibodies, antibody fragments, enzymes, co-factors, receptors, ligands, transcription factors and other regulatory factors, some antigens, cytokines, chemokines, and the like. These peptide-based agents may or may not be naturally occurring.

Another class of agents that can be delivered includes those agents that are not peptide-based. Examples include chemical compounds that are non-naturally occurring, or chemical compounds that are not naturally synthesized by mammalian (and in particular human) cells.

A variety of agents that are currently used for therapeutic or diagnostic purposes can be delivered according to the invention and these include without limitation imaging agents, immunomodulatory agents such as immunostimulatory agents and immunoinhibitory agents, antigens, adjuvants, cytokines, chemokines, anti-cancer agents, anti-infective agents, nucleic acids, antibodies or fragments thereof, fusion proteins such as cytokine-antibody fusion proteins, Fc-fusion proteins, and the like.

Imaging Agents.

As used herein, an imaging agent is an agent that emits signal directly or indirectly thereby allowing its detection in vivo. Imaging agents such as contrast agents and radioactive agents that can be detected using medical imaging techniques such as nuclear medicine scans and magnetic resonance imaging (MRI). Imaging agents for magnetic resonance imaging (MRI) include Gd(DOTA), iron oxide or gold nanoparticles; imaging agents for nuclear medicine include $^{201}$Tl, gamma-emitting radionuclide 99 mTc; imaging agents for positron-emission tomography (PET) include positron-emitting isotopes, (18)F-fluorodeoxyglucose ((18) FDG), (18)F-fluoride, copper-64, gadoamide, and radioisotopes of Pb(II) such as 203 Pb, and 11In; imaging agents for in vivo fluorescence imaging such as fluorescent dyes or dye-conjugated nanoparticles. In other embodiments, the agent to be delivered is conjugated, or fused to, or mixed or combined with an imaging agent.

Immunostimulatory Agents.

As used herein, an immunostimulatory agent is an agent that stimulates an immune response (including enhancing a pre-existing immune response) in a subject to whom it is administered, whether alone or in combination with another agent. Examples include antigens, adjuvants (e.g., TLR ligands such as imiquimod and resiquimod, imidazoquinolines, nucleic acids comprising an unmethylated CpG dinucleotide, monophosphoryl lipid A (MPLA) or other lipopolysaccharide derivatives, single-stranded or double-stranded RNA, flagellin, muramyl dipeptide), cytokines including interleukins (e.g., IL-2, IL-7, IL-15 (or superagonist/mutant forms of these cytokines), IL-12, IFN-gamma, IFN-alpha, GM-CSF, FLT3-ligand, etc.), immunostimulatory antibodies (e.g., anti-CTLA-4, anti-CD28, anti-CD3, or single chain/antibody fragments of these molecules), and the like.

Antigens.

The antigen may be without limitation a cancer antigen, a self or autoimmune antigen, a microbial antigen, an allergen, or an environmental antigen. The antigen may be peptide, lipid, or carbohydrate in nature, but it is not so limited.

Cancer Antigens.

A cancer antigen is an antigen that is expressed preferentially by cancer cells (i.e., it is expressed at higher levels in cancer cells than on non-cancer cells) and in some instances it is expressed solely by cancer cells. The cancer antigen may be expressed within a cancer cell or on the surface of the cancer cell. The cancer antigen may be MART-1/Melan-A, gp100, adenosine deaminase-binding protein (ADAbp), FAP, cyclophilin b, colorectal associated antigen (CRC)—C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5). The cancer antigen may be selected from the group consisting of GAGE-1, GAGE-2, GAGE-3, GAGE-4, GAGE-5, GAGE-6, GAGE-7, GAGE-8, GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100$^{Pmel117}$, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, and c-erbB-2.

Microbial Antigens.

Microbial antigens are antigens derived from microbial species such as without limitation bacterial, viral, fungal, parasitic and mycobacterial species. As such, microbial antigens include bacterial antigens, viral antigens, fungal antigens, parasitic antigens, and mycobacterial antigens. The microbial antigen may be part of a microbial species or it may be the entire microbe.

Allergens.

An allergen is an agent that can induce an allergic or asthmatic response in a subject. Allergens include without limitation pollens, insect venoms, animal dander dust, fungal spores and drugs (e.g. penicillin).

Adjuvants.

The adjuvant may be without limitation alum (e.g., aluminum hydroxide, aluminum phosphate); saponins purified from the bark of the *Q. saponaria* tree such as QS21 (a glycolipid that elutes in the 21st peak with HPLC fractionation; Antigenics, Inc., Worcester, Mass.); poly[di(carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic).

Adjuvants may be TLR ligands. Adjuvants that act through TLR3 include without limitation double-stranded RNA. Adjuvants that act through TLR4 include without limitation derivatives of lipopolysaccharides such as monophosphoryl lipid A (MPLA; Ribi ImmunoChem Research, Inc., Hamilton, Mont.) and muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland). Adjuvants that act through TLR5 include without limitation flagellin. Adjuvants that act through TLR7 and/or TLR8 include single-stranded RNA, oligoribonucleotides (ORN), synthetic low molecular weight compounds such as imidazoquinolinamines (e.g., imiquimod (R-837), resiquimod (R-848)). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

Immunoinhibitory Agents.

As used herein, an immunoinhibitory agent is an agent that inhibits an immune response in a subject to whom it is administered, whether alone or in combination with another agent. Examples include steroids, retinoic acid, dexamethasone, cyclophosphamide, anti-CD3 antibody or antibody fragment, and other immunosuppressants.

Anti-Cancer Agents.

As used herein, an anti-cancer agent is an agent that at least partially inhibits the development or progression of a cancer, including inhibiting in whole or in part symptoms associated with the cancer even if only for the short term. Several anti-cancer agents can be categorized as DNA damaging agents and these include topoisomerase inhibitors (e.g., etoposide, ramptothecin, topotecan, teniposide, mitoxantrone), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), DNA strand break inducing agents (e.g., bleomycin, doxorubicin, daunorubicin, idarubicin, mitomycin C), anti-microtubule agents (e.g., vincristine, vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), anthracyclines, vinca alkaloids. or epipodophyllotoxins.

Examples of anti-cancer agents include without limitation Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Bortezomib (VELCADE); Brequinar Sodium; Bropirimine; Busulfan; Cactinomycin; Calusterone; Caracemide; Carbetimer; Carboplatin (a platinum-containing regimen); Carmustine; Carubicin Hydrochloride; Carzelesin; Cedefingol; Chlorambucil; Cirolemycin; Cisplatin (a platinum-containing regimen); Cladribine; Crisnatol Mesylate; Cyclophosphamide; Cytarabine; Dacarbazine; Dactinomycin; Daunorubicin; Decitabine; Dexormaplatin; Dezaguanine; Diaziquone; Docetaxel (TAXOTERE); Doxorubicin; Droloxifene; Dromostanolone; Duazomycin; Edatrexate; Eflornithine; Elsamitrucin; Enloplatin; Enpromate; Epipropidine; Epirubicin; Erbulozole; Erlotinib (TARCEVA), Esorubicin; Estramustine; Etanidazole; Etoposide; Etoprine; Fadrozole; Fazarabine; Fenretinide; Floxuridine; Fludarabine; 5-Fluorouracil; Fluorocitabine; Fosquidone; Fostriecin; Gefitinib (IRESSA), Gemcitabine; Hydroxyurea; Idarubicin; Ifosfamide; Ilmofosine; Imatinib mesylate (GLEEVAC); Interferon alpha-2a; Interferon alpha-2b; Interferon alpha-n1; Interferon alpha-n3; Interferon beta-I a; Interferon gamma-I b; Iproplatin; Irinotecan; Lanreotide; Lenalidomide (REVLIMID, REVIMID); Letrozole; Leuprolide; Liarozole; Lometrexol; Lomustine; Losoxantrone; Masoprocol; Maytansine; Mechlorethamine; Megestrol; Melengestrol; Melphalan; Menogaril; Mercaptopurine; Methotrexate; Metoprine; Meturedepa; Mitindomide; Mitocarcin; Mitocromin; Mitogillin; Mitomalcin; Mitomycin; Mitosper; Mitotane; Mitoxantrone; Mycophenolic Acid; Nocodazole; Nogalamycin; Ormaplatin; Oxisuran; Paclitaxel; Pemetrexed (ALIMTA), Pegaspargase; Peliomycin; Pentamustine; Pentomone; Peplomycin; Perfosfamide; Pipobroman; Piposulfan; Piritrexim Isethionate; Piroxantrone; Plicamycin; Plomestane; Porfimer; Porfiromycin; Prednimustine; Procarbazine; Puromycin; Pyrazofurin; Riboprine; Rogletimide; Safingol; Semustine; Simtrazene; Sitogluside; Sparfosate; Sparsomycin; Spirogermanium; Spiromustine; Spiroplatin; Streptonigrin; Streptozocin; Sulofenur; Talisomycin; Tamsulosin; Taxol; Taxotere; Tecogalan; Tegafur; Teloxantrone; Temoporfin; Temozolomide (TEMODAR); Teniposide; Teroxirone; Testolactone; Thalidomide (THALOMID) and derivatives thereof; Thiamiprine; Thioguanine; Thiotepa; Tiazofurin; Tirapazamine; Topotecan; Toremifene; Trestolone; Triciribine; Trimetrexate; Triptorelin; Tubulozole; Uracil Mustard; Uredepa; Vapreotide; Verteporfin; Vinblastine; Vincristine; Vindesine; Vinepidine; Vinglycinate; Vinleurosine; Vinorelbine; Vinrosidine; Vinzolidine; Vorozole; Zeniplatin; Zinostatin; Zorubicin.

The anti-cancer agent may be an enzyme inhibitor including without limitation tyrosine kinase inhibitor, a CDK inhibitor, a MAP kinase inhibitor, or an EGFR inhibitor. The tyrosine kinase inhibitor may be without limitation Genistein (4',5,7-trihydroxyisoflavone), Tyrphostin 25 (3,4,5-trihydroxyphenyl), methylene]-propanedinitrile, Herbimycin A, Daidzein (4',7-dihydroxyisoflavone), AG-126, trans-1-(3'-carboxy-4'-hydroxyphenyl)-2-(2",5"-dihydroxyphenyl)ethane, or HDBA (2-Hydroxy-5-(2,5-Dihydroxybenzylamino)-2-hydroxybenzoic acid. The CDK inhibitor may be without limitation p21, p27, p57, p15, p16, p18, or p19. The MAP kinase inhibitor may be without limitation KY12420 ($C_{23}H_{24}O_8$), CNI-1493, PD98059, or 4-(4-Fluorophenyl)-2-(4-methylsulfinyl phenyl)-5-(4-pyridyl) 1H-imidazole. The EGFR inhibitor may be without limitation erlotinib (TARCEVA), gefitinib (IRESSA), WHI-P97 (quinazoline derivative), LFM-A12 (leflunomide metabolite analog), ABX-EGF, lapatinib, canertinib, ZD-6474 (ZACTIMA), AEE788, and AG1458.

The anti-cancer agent may be a VEGF inhibitor including without limitation bevacizumab (AVASTIN), ranibizumab (LUCENTIS), pegaptanib (MACUGEN), sorafenib, sunitinib (SUTENT), vatalanib, ZD-6474 (ZACTIMA), anecortave (RETAANE), squalamine lactate, and semaphorin.

The anti-cancer agent may be an antibody or an antibody fragment including without limitation an antibody or an antibody fragment including but not limited to bevacizumab (AVASTIN), trastuzumab (HERCEPTIN), alemtuzumab (CAMPATH, indicated for B cell chronic lymphocytic leukemia,), gemtuzumab (MYLOTARG, hP67.6, anti-CD33, indicated for leukemia such as acute myeloid leukemia), rituximab (RITUXAN), tositumomab (BEXXAR, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX, indicated for ovarian cancer), edrecolomab (PANOREX), daclizumab (ZENAPAX), palivizumab (SYNAGIS, indicated for respiratory conditions such as RSV infection), ibritumomab tiuxetan (ZEVALIN, indicated for Non-Hodgkin's lymphoma), cetuximab (ERBITUX), MDX-447, MDX-22, MDX-220 (anti-TAG-72), IOR-C5, IOR-T6 (anti-CD1), IOR EGF/R3, celogovab (ONCOSCINT OV103), epratuzumab (LYMPHOCIDE), pemtumomab (THERAGYN), and Gliomab-H (indicated for brain cancer, melanoma).

Hematopoietic Differentiating Agents.

The agent may be one that stimulates the differentiation of hematopoietic progenitor cells towards one or more lineages. Examples include without limitation IL-3, G-CSF, GM-CSF, M-CSF, thrombopoeitin, erythropoietin, Wnt5A, Wnt11A, and the like.

Hematopoietic Self-Renewing Agents.

The agent may be one that stimulates the self-renewal of hematopoietic progenitor cells. Examples include without limitation kit ligand, GSK3-beta inhibitors, Wnt5A together with SLF, Notch1 activators, Lnk inhibitors, prostaglandin E2 (PGE2) and agents that stimulate the PGE2 pathway including PGE2, PGI2, Linoleic Acid, 13(s)-HODE, LY171883, Mead Acid, Eicosatrienoic Acid, Epoxyeicosatrienoic Acid, ONO-259, Cay1039, a PGE2 receptor agonist, of 16,16-dimethyl PGE2, 19(R)-hydroxy PGE2, 16,16-dimethyl PGE2 p-(p-acetamidobenzamido) phenyl ester, 11-deoxy-16,16-dimethyl PGE2,9-deoxy-9-methylene-16,16-dimethyl PGE2,9-deoxy-9-methylene PGE2, Butaprost, Sulprostone, PGE2 serinol amide, PGE2 methyl ester, 16-phenyl tetranor PGE2,15(S)-15-methyl PGE2,15 (R)-15-methyl PGE2, BIO, 8-bromo-cAMP, Forskolin, Bapta-AM, Fendiline, Nicardipine, Nifedipine, Pimozide, Strophanthidin, Lanatoside, L-Arg, Sodium Nitroprusside, Sodium Vanadate, Bradykinin, Mebeverine, Flurandrenolide, Atenolol, Pindolol, Gaboxadol, Kynurenic Acid, Hydralazine, Thiabendazole, Bicuclline, Vesamicol, Peruvoside, Imipramine, Chlorpropamide, 1,5-Pentamethylenetetrazole, 4-Aminopyridine, Diazoxide, Benfotiamine, 12-Methoxydodecenoic acid, N-Formyl-Met-Leu-Phe, Gallamine, IAA 94, Chlorotrianisene, and derivatives thereof, and the like.

Anti-Infective Agents.

The agent may be an anti-infective agent including without limitation an anti-bacterial agent, an anti-viral agent, an anti-parasitic agent, an anti-fungal agent, and an anti-mycobacterial agent.

Anti-bacterial agents may be without limitation β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, sulfonamides and trimethoprim, or quinolines.

Other anti-bacterials may be without limitation Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; or Zorbamycin.

Anti-mycobacterial agents may be without limitation Myambutol (Ethambutol Hydrochloride), Dapsone (4,4'-diaminodiphenylsulfone), Paser Granules (aminosalicylic acid granules), Priftin (rifapentine), Pyrazinamide, Isoniazid, Rifadin (Rifampin), Rifadin IV, Rifamate (Rifampin and Isoniazid), Rifater (Rifampin, Isoniazid, and Pyrazinamide), Streptomycin Sulfate or Trecator-SC (Ethionamide).

Anti-viral agents may be without limitation amantidine and rimantadine, ribivarin, acyclovir, vidarabine, trifluorothymidine, ganciclovir, zidovudine, retonovir, and interferons.

Anti-viral agents may be without limitation further include Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime or integrase inhibitors.

Anti-fungal agents may be without limitation imidazoles and triazoles, polyene macrolide antibiotics, griseofulvin, amphotericin B, and flucytosine. Antiparasites include heavy metals, antimalarial quinolines, folate antagonists, nitroimidazoles, benzimidazoles, avermectins, praxiquantel, ornithine decarboxylase inhibitors, phenols (e.g., bithionol, niclosamide); synthetic alkaloid (e.g., dehydroemetine); piperazines (e.g., diethylcarbamazine); acetanilide (e.g., diloxanide furonate); halogenated quinolines (e.g., iodoquinol (diiodohydroxyquin)); nitrofurans (e.g., nifurtimox); diamidines (e.g., pentamidine); tetrahydropyrimidine (e.g., pyrantel pamoate); or sulfated naphthylamine (e.g., suramin).

Other anti-infective agents may be without limitation Difloxacin Hydrochloride; Lauryl Isoquinolinium Bromide; Moxalactam Disodium; Ornidazole; Pentisomicin; Sarafloxacin Hydrochloride; Protease inhibitors of HIV and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); Ciprofloxacin (Cipro); Aminacrine Hydrochloride; Benzethonium Chloride:Bithionolate Sodium; Bromchlorenone; Carbamide Peroxide; Cetalkonium Chloride; Cetylpyridinium Chloride:Chlorhexidine Hydrochloride; Clioquinol; Domiphen Bromide; Fenticlor; Fludazonium Chloride; Fuchsin, Basic; Furazolidone; Gentian Violet; Halquinols; Hexachlorophene:Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofurazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal; or Troclosene Potassium.

Nucleic Acid Agents.

Nucleic acids that can be delivered to a subject according to the invention include naturally or non-naturally occurring DNA (including cDNA, genomic DNA, nuclear DNA, mitochondrial DNA), RNA (including mRNA, rRNA, tRNA), oligonucleotides, a triple-helix forming molecule, immunostimulatory nucleic acids such as those described in U.S. Pat. No. 6,194,388 (the teachings of which relating to immunostimulatory CpG nucleic acids are incorporated herein by reference), small interfering RNA (siRNA) or microRNAs (miRNA) used to modulate gene expression, antisense oligonucleotides used to modulate gene expression, aptamers, ribozymes, a gene or gene fragment, a regulatory sequence, including analogs, derivatives, and combinations thereof. These nucleic acids may be administered neat or complexed to another entity, for example in order to facilitate their binding to and/or uptake by target tissues and/or cells.

Anti-Inflammatory Agents.

Anti-inflammatory agents are agents that reduce or eliminate inflammation. They include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium. One preferred anti-inflammatory agent is aspirin.

Other Agents.

The agent may be without limitation adrenergic agent; adrenocortical steroid; adrenocortical suppressant; alcohol deterrent; aldosterone antagonist; ammonia detoxicant; amino acid; amylotropic lateral sclerosis agent; anabolic; analeptic; analgesic; androgen; anesthetic; anorectic; anorexic; anterior pituitary activator; anterior pituitary suppressant; anthelmintic; anti-acne agent; anti-adrenergic; anti-allergic; anti-amebic; anti-androgen; anti-anemic; anti-anginal; anti-anxiety; anti-arthritic; anti-asthmatic including β-adrenergic agonists, methylxanthines, mast cell stabilizing agents, anticholinergics, adrenocortical steroids such as glucocorticoids; anti-atherosclerotic; anticholelithic; anticholelithogenic; anticholinergic; anticoagulant; anticoccidal; anticonvulsant; antidepressant; antidiabetic; antidiarrheal; antidiuretic; antidote; antidyskinetic; anti-emetic; anti-epileptic; anti-estrogen; antifibrinolytic; antiglaucoma; anti-hemorrhagic; antihemorrheologic; antihistamine; antihyperlipidemic; antihyperlipoproteinemic; antihypertensive; antihypotensive; anti-infective; anti-inflammatory; antikeratinizing agent; antimigraine; antimitotic; antimycotic; antinauseant; antineutropenic; antiobsessional agent; antioxidant; antiparkinsonian; antiperistaltic; antipneumocystic; antiprostatic hypertrophy agent; antiprotozoal; antipruritic; antipsoriatic; antipsychotic; antirheumatic; antischistosomal; antiseborrheic; antisecretory; antispasmodic; antithrombotic; antitussive; anti-ulcerative; anti-urolithic; appetite suppressant; blood glucose regulator; bone resorption inhibitor; bronchodilator; carbonic anhydrase inhibitor; cardiac depressant; cardioprotectant; cardiotonic; cardiovascular agent; cerebral ischemia agent; choleretic; cholinergic; cholinergic agonist; cholinesterase deactivator; coccidiostat; cognition adjuvant; cognition enhancer; conjunctivitis agent; contrast agent; depressant; diagnostic aid; diuretic; dopaminergic agent; ectoparasiticide; emetic; enzyme inhibitor; estrogen; estrogen receptor agonist; fibrinolytic; fluorescent agent; free oxygen radical scavenger; gastric acid suppressant; gastrointestinal motility effector; geriatric agent; glucocorticoid; gonad-stimulating principle; hair growth stimulant; hemostatic; herbal active agent; histamine H2 receptor antagonists; hormone; hypocholesterolemic; hypoglycemic; hypolipidemic; hypotensive; HMGCoA reductase inhibitor; impotence therapy adjunct; inflammatory bowel disease agent; keratolytic; LHRH agonist; liver disorder agent; luteolysin; memory adjuvant; mental performance enhancer; mineral; mood regulator; mucolytic; mucosal protective agent; multiple sclerosis agent; mydriatic; nasal decongestant; neuroleptic; neuromuscular blocking agent; neuroprotective; NMDA antagonist; non-hormonal sterol derivative; nutrient; oxytocic; Paget's disease agent; plasminogen activator; platelet activating factor antagonist; platelet aggregation inhibitor; post-stroke and post-head trauma agents; progestin; prostaglandin; prostate growth inhibitor; prothyrotropin; psychotropic; radioactive agent; relaxant; rhinitis agent; scabicide; sclerosing agent; sedative; sedative-hypnotic; selective adenosine Al antagonist; sequestering agents; serotonin antagonist; serotonin inhibitor; serotonin receptor antagonist; steroid; stimulant; suppressant; thyroid hormone; thyroid inhibitor; thyromimetic; tranquilizer; unstable angina agent; uricosuric; vasoconstrictor; vasodilator; vulnerary; wound healing agent; or xanthine oxidase inhibitor.

The nucleic acid structures may alternatively or additionally contain or comprise a detectable marker or a reporter. The detectable marker can be detected directly for example by its ability to emit and/or absorb electromagnetic radiation of a particular wavelength. A marker can be detected indirectly for example by its ability to bind, recruit and, in some cases, cleave another moiety which itself may emit or absorb light of a particular wavelength (e.g., an epitope tag such as the FLAG epitope, an enzyme tag such as horseradish peroxidase, etc.). Generally the detectable marker can be selected from the group consisting of directly detectable labels such as a fluorescent molecule (e.g., fluorescein, rhodamine, tetramethylrhodamine, R-phycoerythrin, Cy-3, Cy-5, Cy-7, Texas Red, Phar-Red, allophycocyanin (APC), fluorescein amine, eosin, dansyl, umbelliferone, 5-carboxyfluorescein (FAM), 2'7'-dimethoxy-4'5'-dichloro-6-carboxyfluorescein (JOE), 6 carboxyrhodamine (R6G), N,N,N',N'-tetramethyl-6-carboxyrhodamine (TAMRA), 6-carboxy-X-rhodamine (ROX), 4-(4'-dimethylaminophenylazo)benzoic acid (DABCYL), 5-(2'-aminoethyl)aminonaphthalene-1-sulfonic acid (EDANS), 4-acetamido-4'-isothiocyanatostilbene-2,2'disulfonic acid, acridine, acridine isothiocyanate, r-amino-N-(3-vinylsulfonyl)phenylnaphthalimide-3,5, disulfonate (Lucifer Yellow VS), N-(4-anilino-1-naphthyl)maleimide, anthranilamide, Brilliant Yellow, coumarin, 7-amino-4-methylcoumarin, 7-amino-4-trifluoromethylcouluarin (Coumarin 151), cyanosine, 4',6-diaminidino-2-phenylindole (DAPI), 5',5"-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 4-dimethylaminophenylazophenyl-4'-isothiocyanate (DABITC), eosin isothiocyanate, erythrosin B, erythrosin isothiocyanate, ethidium, 5-(4,6-dichlorotriazin-2-yl)aminofluorescein (DTAF), QFITC(XRITC), fluorescamine, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron® Brilliant Red 3B-A), lissamine rhodamine B sulfonyl chloride, rhodamine B, rhodamine 123, rhodamine X, sulforhodamine B, sulforhodamine 101, sulfonyl chloride derivative of sulforhodamine 101, tetramethyl rhodamine, riboflavin, rosolic acid, and terbium chelate derivatives), a chemiluminescent molecule, a bioluminescent molecule, a chromogenic molecule, a radioisotope (e.g., $P^{32}$ or $H^3$, $^{14}C$, $^{125}I$ and $^{131}I$), an electron spin resonance molecule (such as for example nitroxyl radicals), an optical or electron density molecule, an electrical charge transducing or transferring molecule, an electromagnetic molecule such as a magnetic or paramagnetic bead or particle, a semiconductor nanocrystal or nanoparticle (such as quantum dots described for example in U.S. Pat. No. 6,207,392 and commercially available from Quantum Dot Corporation and Evident Technologies), a colloidal metal, a colloid gold nanocrystal, a nuclear magnetic resonance molecule, and the like.

The detectable marker can also be selected from the group consisting of indirectly detectable labels such as an enzyme (e.g., alkaline phosphatase, horseradish peroxidase, β-galactosidase, glucoamylase, lysozyme, luciferases such as firefly luciferase and bacterial luciferase (U.S. Pat. No. 4,737,456); saccharide oxidases such as glucose oxidase, galactose oxidase, and glucose-6-phosphate dehydrogenase; heterocyclic oxidases such as uricase and xanthine oxidase coupled to an enzyme that uses hydrogen peroxide to oxidize a dye precursor such as HRP, lactoperoxidase, or microperoxidase), an enzyme substrate, an affinity molecule, a ligand, a receptor, a biotin molecule, an avidin molecule, a streptavidin molecule, an antigen (e.g., epitope tags such as the FLAG or HA epitope), a hapten (e.g., biotin, pyridoxal, digoxigenin fluorescein and dinitrophenol), an antibody, an antibody fragment, a microbead, and the like. Antibody fragments include Fab, $F(ab)_2$, Fd and antibody fragments which include a CDR3 region.

As will become clear based on the disclosure provided herein, the invention provides systems comprised of two or more layers of nucleic acid sequestration. Each "layer" as the term is used herein refers to one and typically a plurality of identical nucleic acid containers having identical components. In some instances, the system is designed so that the number of containers in each successive layer is greater than the layer before. In this way, amplification of signal is attained.

Compositions and Components

Boxes/containers or other structures can be designed with software packages such as caDNAno[4]. Sequences are largely dictated by natural single-stranded sequences such as that of the M13 virus, which typically form the "scaffold" (or backbone) of the structure. Software packages such as NUPACK[5] can also be used to design dynamic sequence components. Demonstrations and applications are enumerated in the following non-limiting examples. Those of ordinary skill in the art are familiar with these methods as evidenced by the disclosures in U.S. Pat. No. 7,745,594, U.S. Pat. No. 7,842,793, US 2010/00696621, and Goodman et al. Nature Nanotechnology, doi 10.1038/nnano.2008.3, the entire contents of which including the methods for generating nucleic acid based structures are incorporated by reference herein.

Some aspects and embodiments of the invention contemplate an open-ended container for the spatial sequestration of tethered dynamic nucleic acid sequences. A nucleic acid-based container can be made from DNA origami[6,7] or other methods, with one or more opposite ends open, such that fluid and free DNA molecules can flow through its interior. The container can be made sufficiently rigid to maintain its shape under thermal and other external forces typical in solution. Such containers can sequester one or more nucleic acid (e.g., DNA) strands from a dynamic circuit, by tethering them to the inside surface of the container. In some instances, strands are held deep within the containers and/or they are not able to extend outside of the structure such that strands in separate containers cannot interact with each other (FIG. 1). The containers holding potentially-interacting strands may be of similar size and shape, although they are not so limited provided that the strands from separate containers do not interact with each other (FIG. 1).

Figure 2:
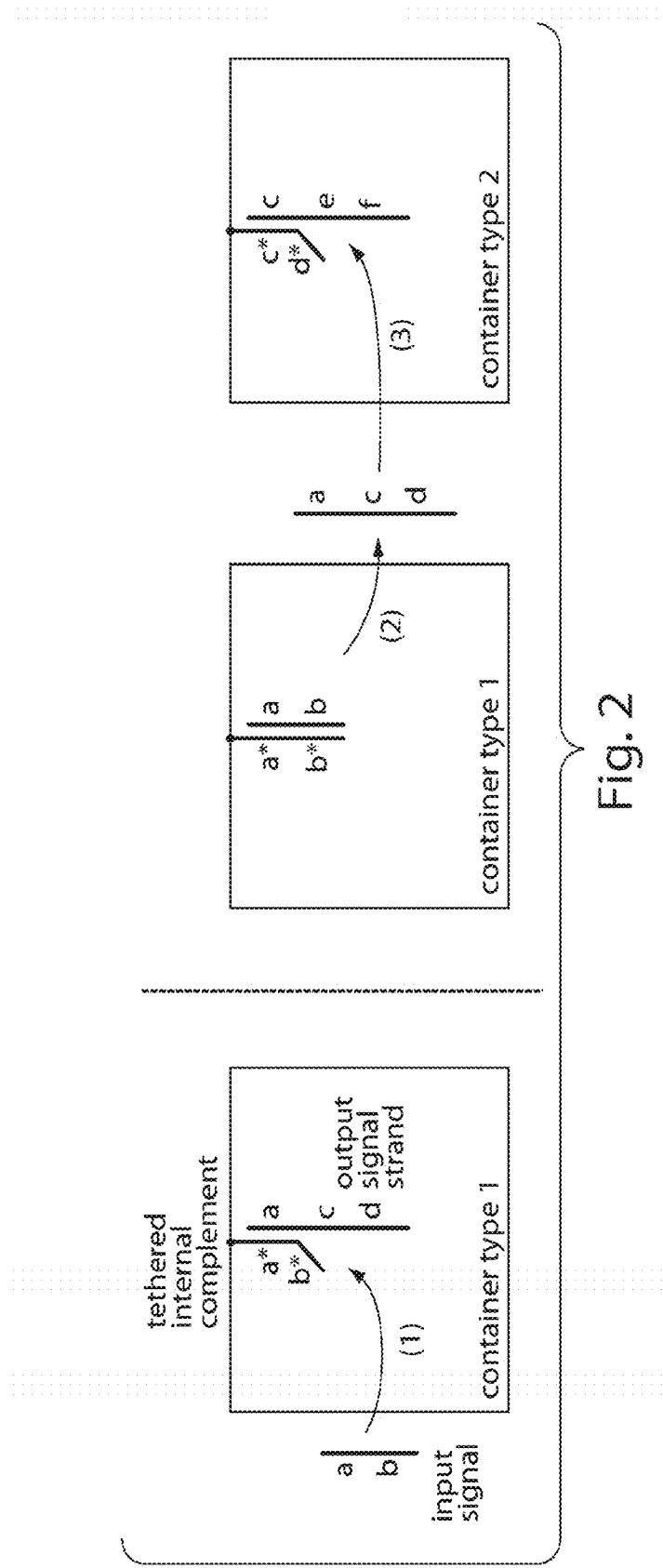
FIG. 2: Close-up of hybridization of output signal strand to a complement tethered within the container (e.g., via ~6-20 nucleotide unique sequence domain "a," hybridized to complementary sequence "a*"). The tether may have a ~4-10 nucleotide toehold component "b*," such that (1) an external input signal "ab" can diffuse in, bind the toehold via complementarity of b to b*, and displace and (2) release the signal strand "acd." The released signal strand may then, for example, serve as (3) an input signal to another container type.

In some embodiments, those strands that act as components of dynamic circuits are conditionally held within sequestering containers by hybridization to a strand that is permanently-tethered within the container (FIG. 2). Soluble input strands (e.g., containing a sequence labeled "ab," as in the Figure) can release the sequestered dynamic strands (e.g., containing sequence "acd") by simply diffusing into an open end of the structure, binding a single-stranded, complementary sequence ("toehold") on the retaining (non-dynamic, permanently tethered) strand (e.g., labeled "b*" on strand "b*a*"), and, via the strand displacement process[2,8], displace and release the sequestered dynamic strand (e.g., "acd"). The released dynamic strand in turn acts as an "output signal strand" since it is able to exit the first structure and enter another structure. This previously-sequestered output signal strand is then free to interact with signals from other structures, including for example by acting as an input signal to release signals from downstream containers (e.g., by binding "d*c*" to release "cef").

Figure 3:
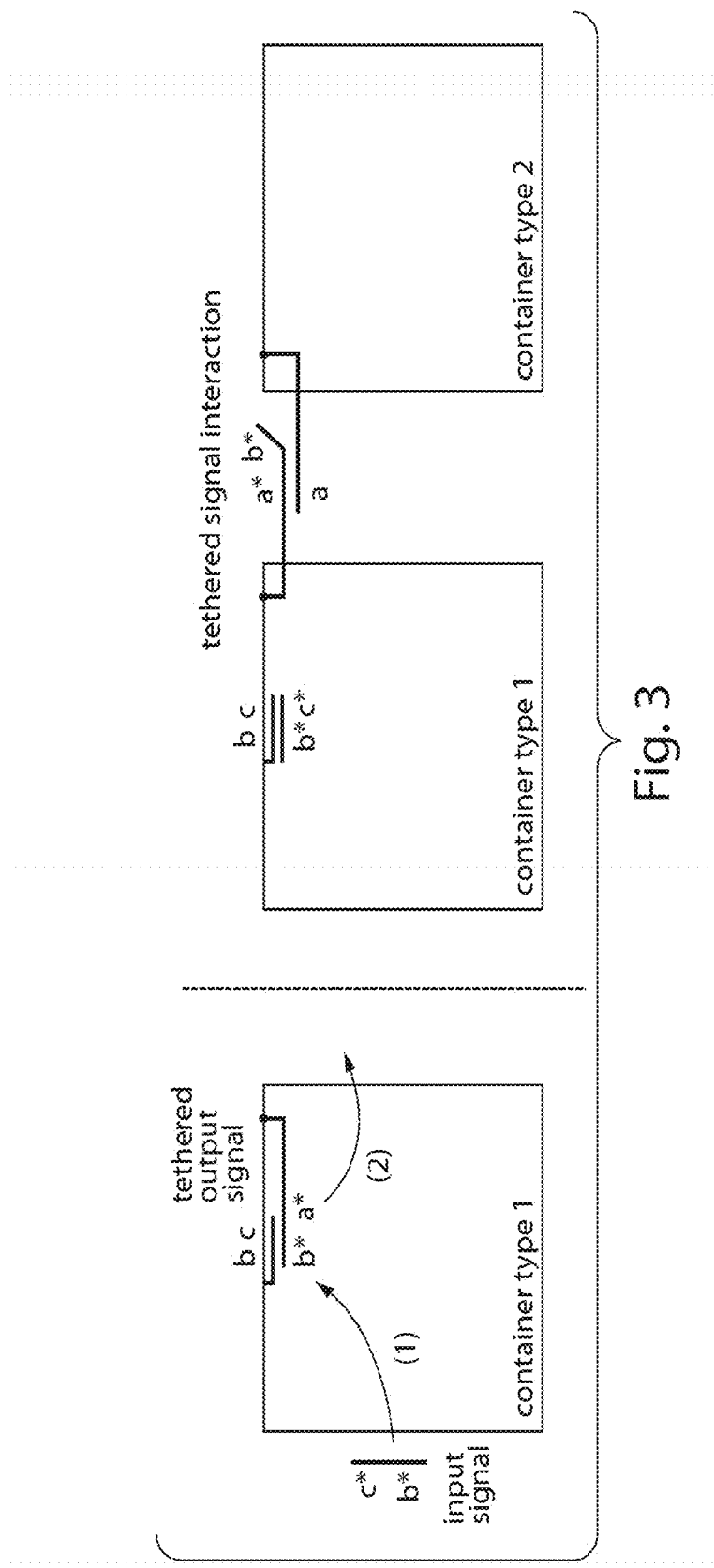
FIG. 3: Sequestered signal strands in an open container may be made available without complete release when (1) an input signal causes (2) the display of an output signal near the edge of the container opening, where it may interact with strands tethered to other containers. In this case, input signal "c*b*" binds toehold "c" of the internal tether "bc" and causes the release of one end of signal "a*b*" which in turn is able to interact with "a" from a separate container. This latter interaction, in one embodiment, may make use of a further toehold at exposed sequence (domain) b*. That toehold may be used to displace "a" from "a*b*" and this in turn may be used to later release containers from each other.

In other embodiments, instead of release of sequestered strands, one end of the strands may be temporarily allowed to extend outside an open end of the container, where they may interact permanently or transiently with other strands including strands that are themselves still tethered to another structure (FIG. 3). The presence of strands outside a container (which may be referred to herein as a "display") may be reversible, and the dynamic strands may be again sequestered. As shown in FIG. 3, the input signal strand "c*b*" binds to one retaining strand (with sequence named "bc") in the container by hybridizing its sequence "c*" with the yet un-hybridized complementary toehold sequence "c." The tethered strand "a*b*," the output signal, is displaced from the "bc" strand and then available to interact with another strand that may be inside (not shown) or outside (FIG. 3) the container. The interaction between the displaced output signal strand and another strand (which for example may be itself tethered to another structure) may result in the cascading attachment of similar structures by containing within the output strand sequences which act as toehold-binding input signals to other similar elements.

Figure 4:
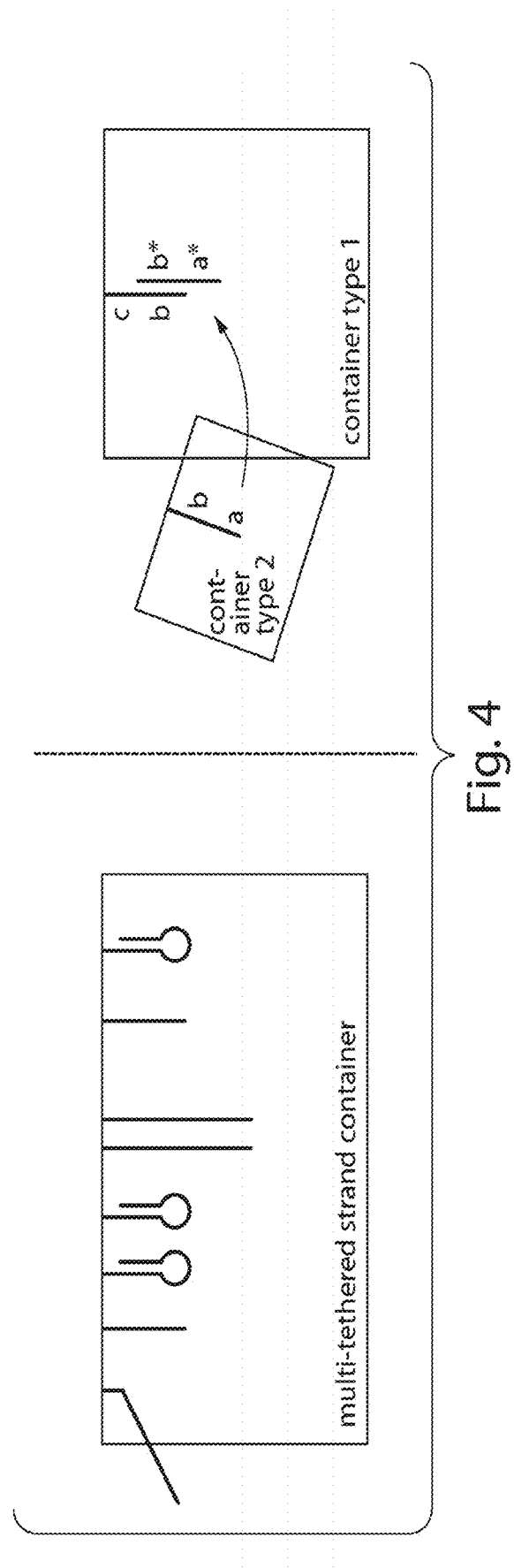
FIG. 4: (left) Multiple strands may be tethered within a container, in reach of some of the others and therefore able to interact in limited combinations. In addition, some strands may interact with soluble signals or nearby tethered signals. (right) Sequestering signals within containers of different size allows combinations of otherwise soluble strands to interact. In this case, due to the small size of container 2, signal "ab" can bind and remove signal "b*a*" from container 1.

Alternatively, multiple dynamic strands may be sequestered within one container, such that many can interact with each other but have no interaction with strands in other containers (FIG. 4, left). Communication with outside strand signals may come in the form of soluble strands, which can diffuse into the multiple-strand containers, or via elements partially sequestered within containers than can reach and interact with those on the margins of other containers (as in FIG. 3).

Another embodiment involves the use of containers of different sizes, such that some (e.g., small) containers are not allowed to interact with each other, but strands sequestered within them can interact with strands sequestered within larger containers (FIG. 4, right). This system allows limited types of interactions without strand release to a soluble state.

Figure 5:
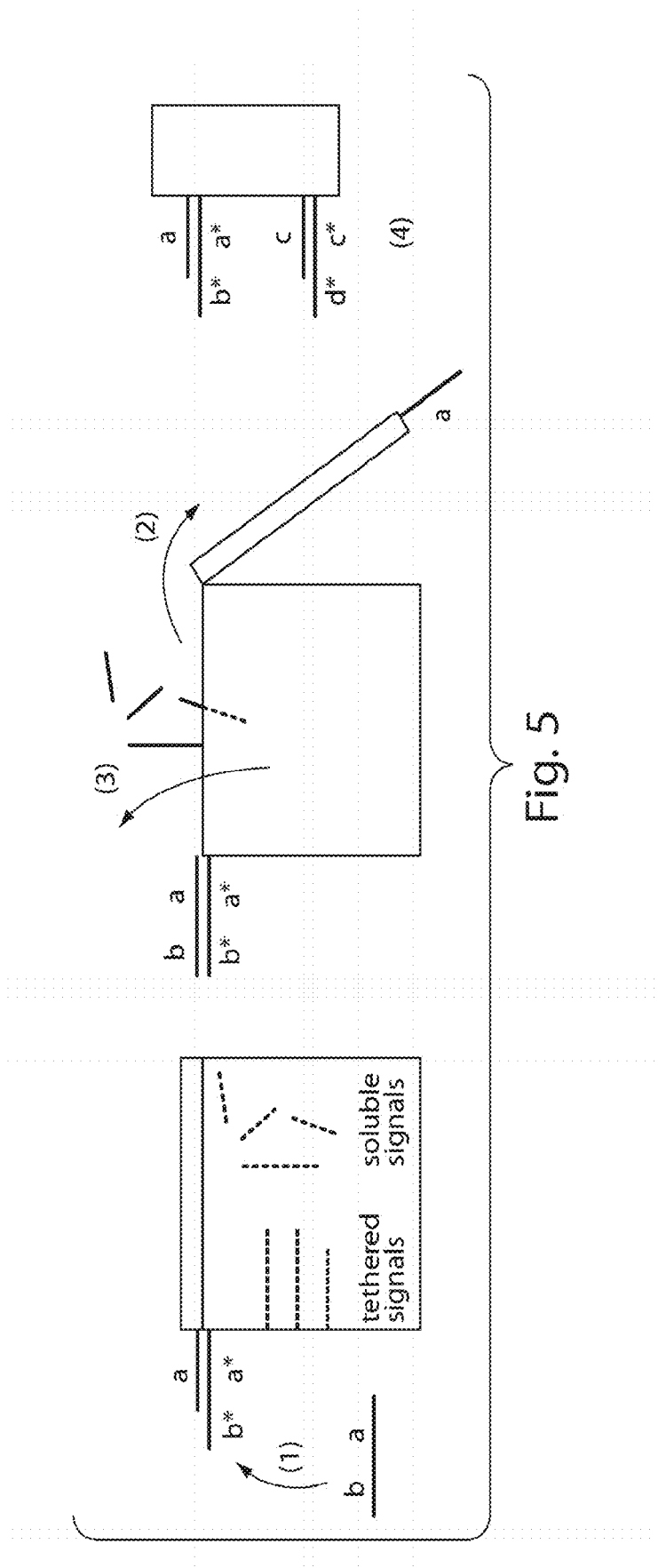
FIG. 5: Completely sealed containers may hold tethered and/or soluble signal strands. They contain a hinged lid or other opening device, controlled by hybridization "locks." (1) A key, here of sequence "ab," binds toehold "b*" of the lock and displaces domain "a" of the complementary lock strand, thus (2) opening the box and (3) allowing release and/or interaction of strands with the environment. (4) Locks may be present in combinations, each itself capable of holding the lid shut. Here, keys "ab" and "cd" are both required to open the lid. Other lock geometries are possible.

The invention also contemplates a completely enclosed container for the spatial sequestration of nucleic aid sequences. In contrast to the open container embodiments described above, containers can be made completely closed, sealing in or out any soluble or locally-tethered nucleic acid strands (FIG. 5). The container typically incorporates a mechanism for opening a pathway into the free solution in its interior, such as for example by way of a hinged lid. The lid or other opening may itself be controlled by one or more nucleic acid "locks" consisting of a hybridization pair ("a" and "b*a*") with individual strands originating one each from the box and lid, such that hybridization holds the lid closed against the box (FIG. 5). A separate DNA "key" strand ("ab") can displace one lock strand from the other by strand displacement or other technique, thus allowing the container to open. The container may comprise tethered nucleic acids which may be bound to output signals the release of which may require another input signal nucleic acid, and/or it may contain free flowing output nucleic acid signals that are simply released once the container is opened.

The key or keys controlling the opening of the lid can be configured in any combination of logical gates (FIG. 5). Two locks operating in parallel (lock "a"/"b*a*" and lock "c"/"d*c*" in the Figure), each itself capable of holding closed the lid and requiring different keys to open, constitute an "AND" gate, for example, with both key signals required for opening. Individual locks which contain two separate "toeholds" for two different keys, either one of which can carry out a strand displacement to open that lock, represent a logical "OR" gate. Locks requiring the binding of multiple copies of the same key further represent a more refined concentration-dependent lock. More complex combinations of these structures can in general be employed for precise control over release of the box contents.

Figure 6:
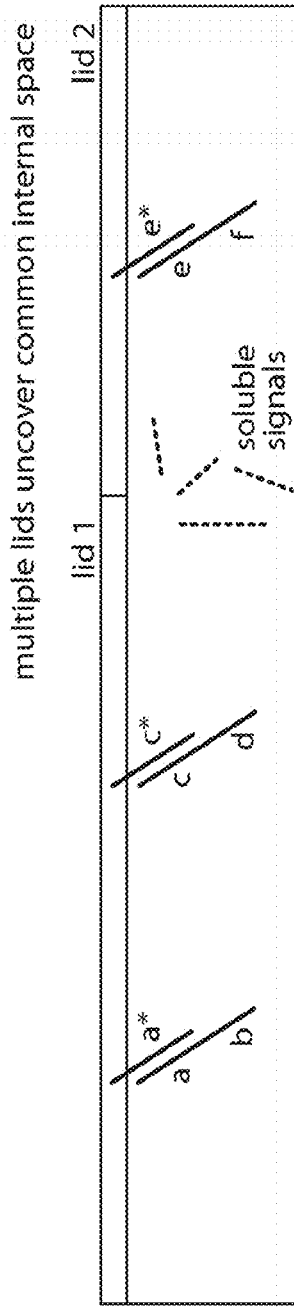
FIG. 6: A single, sealed container may incorporate multiple lids or other potential openings, each with its own combination of nucleic acid lock mechanisms. As shown, both the existence of "b*a*" and "d*c*" are required to open lid 1, setting free the soluble signals. Alternatively, the presence of signal "f*e*" opens lid 2, also setting free the same soluble signal components.

Another method of applying combinatorial logic to container lids comprises the use of multiple lids or other openings, each controlled by a different lock or set of locks in parallel (FIG. 6). In such configurations, all lids lead to one single large compartment within the container. Multiple locks on a given lid represent "AND" gates, while each separate lid represents an "OR" gate.

The invention contemplates that output signals are loaded into a container before it is closed (e.g., via a lock mechanism). This can be done by incorporating the signals within the container during construction (during annealing), with output signals attached to the interior surface through a photo-cleavable linker. These output signals typically do not contribute to the stability or structure of the container. Once the container is loaded and closed, ultra-violet light can be used to cleave the link, setting output signals free within the container. Alternatively, a lock may be designed that has two strand components "a" and "b," where external strand "a*b*c*" can be added to lock the container after manufacturing (and strand "abc" could later serve as a key). This allows for a completed container with an open lid to be loaded by providing a very high concentration of soluble signals, with the soluble signals binding to very short (weak) binding sites within the container. When the container is closed and locked, the majority of sites would contain signals. Later, when opened in an environment of low signal concentration, the signals would preferentially leave the container (i.e., by entropic effects).

Three general illustrative examples are described, each of which can exist in a variety of configurations. Two are closed containers with locked lids, one having tethered internal signals and the other having soluble internal signals, and one is a simple "tile" geometry that requires tethering of the signal.

The invention further contemplates a completely enclosed container for spatial sequestration of free, soluble nucleic aid sequences. A sealed nucleic acid-based container with a controllable lid comprises a number of freely-soluble nucleic acid signal strands in its interior (FIG. 5, "soluble signals"). Strands may be multiple copies of the same strand species, different strand species, or any combination. These strands may be part of a dynamic circuit in which components interact with each other or components not found within the container but potentially available outside of it. They are thus spatially-sequestered and limited in their interaction. Upon opening of the lid, the soluble strands are able to diffuse passively from the container and interact with any other accessible strands in solution, or with strands tethered to other structures.

The invention further contemplates a completely enclosed container for spatial sequestration of internally-tethered nucleic aid sequences. Here, instead of soluble strands contained within the closed container, the nucleic acid strands are tethered to the inside of the container (FIG. 5, "tethered signals"). Once the container is opened, strands continue to be tethered but are able to interact with strands in solution (e.g., input signal nucleic acids that migrate into the structure). The newly-exposed strands are also able to interact with strands tethered to other containers or structures if they are within physical proximity. The strands may be tethered to the interior surface of the lid of the container. This may increase their accessibility to the external environment once the container is opened.

Figure 7:
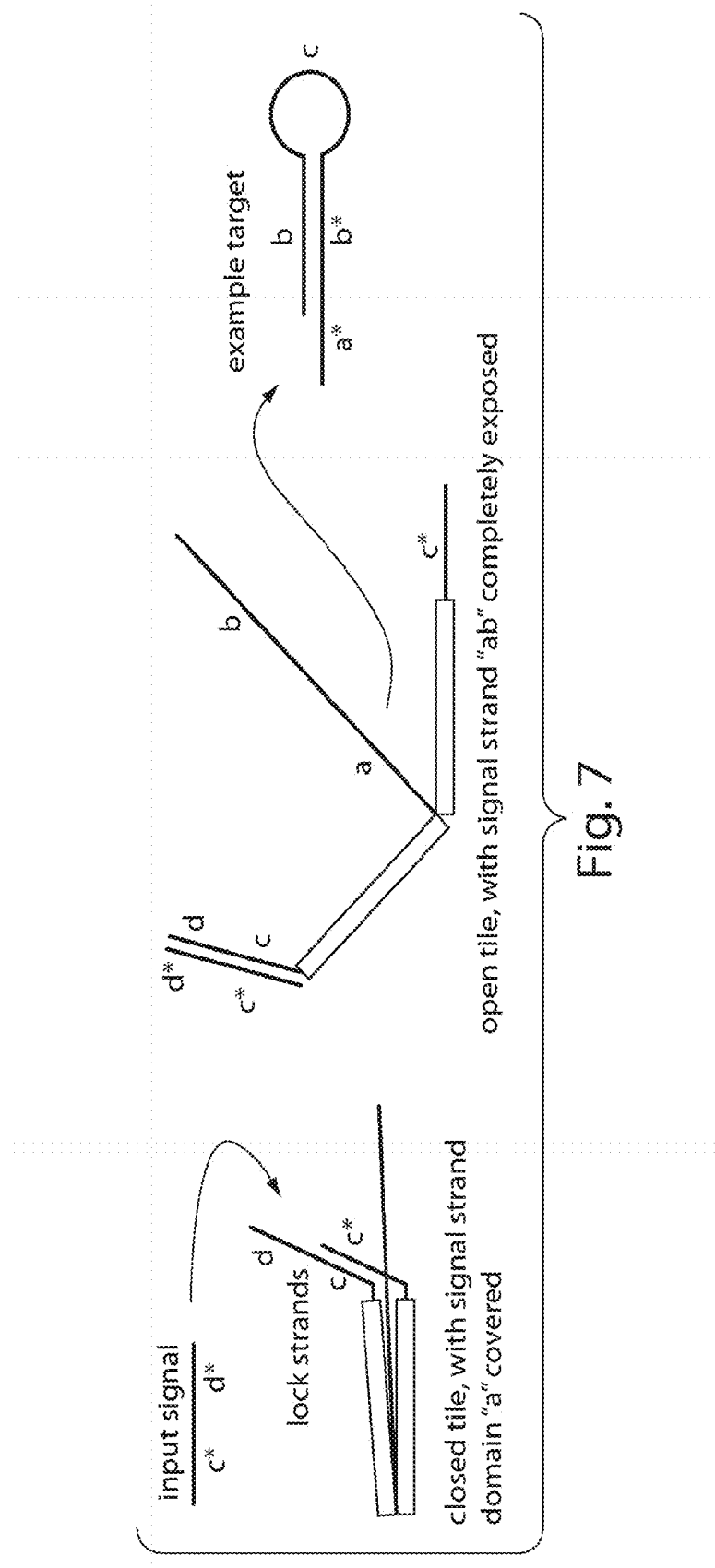
FIG. 7: A small DNA-based tile structure, with a hinge and lock operating identically to the larger structures of FIG. 5, can prevent hybridization of the sequestered signal by steric hindrance. In this example, input signal "c*d*" binds the lock at "d" and displaces "c*" from "dc," opening the tile. When open, domain "a" is exposed and can interact with external strand signals such as hairpin "a*b*cb." Interaction of "ab" with "a*b*cb" in turn opens up the hairpin of the latter strand and renders the "cb" sequences or domains single stranded and accessible for binding to further sequences.

The invention further contemplates a small tile-like structure for the spatial sequestration of internally-tethered strands. Instead of a traditional, hollow container, nucleic acid signal strands may be prevented from interacting with other nucleic acid strands by spatial sequestration or steric hindrance effected by folding a relatively rigid nucleic acid tile (or relatively planar structure) over the strand (FIG. 7, resembling the configuration of a bookmark and book). In this arrangement, some or all of the nucleic acid may be inaccessible when the planar structure is closed. In some embodiments, at least the portion of the dynamic nucleic acid strand that initializes signal transduction (e.g., the toehold) can be covered and protected from interaction or reaction by the rigid tile. The tile can be constructed of any number of existing DNA tile motifs[1], designed to fold over and cover the signaling strand. A lock, equivalent to those described in FIG. 5, can be used to hold the folded portions of the tile shut against the signal strand, thereby exerting control.

Figure 8:
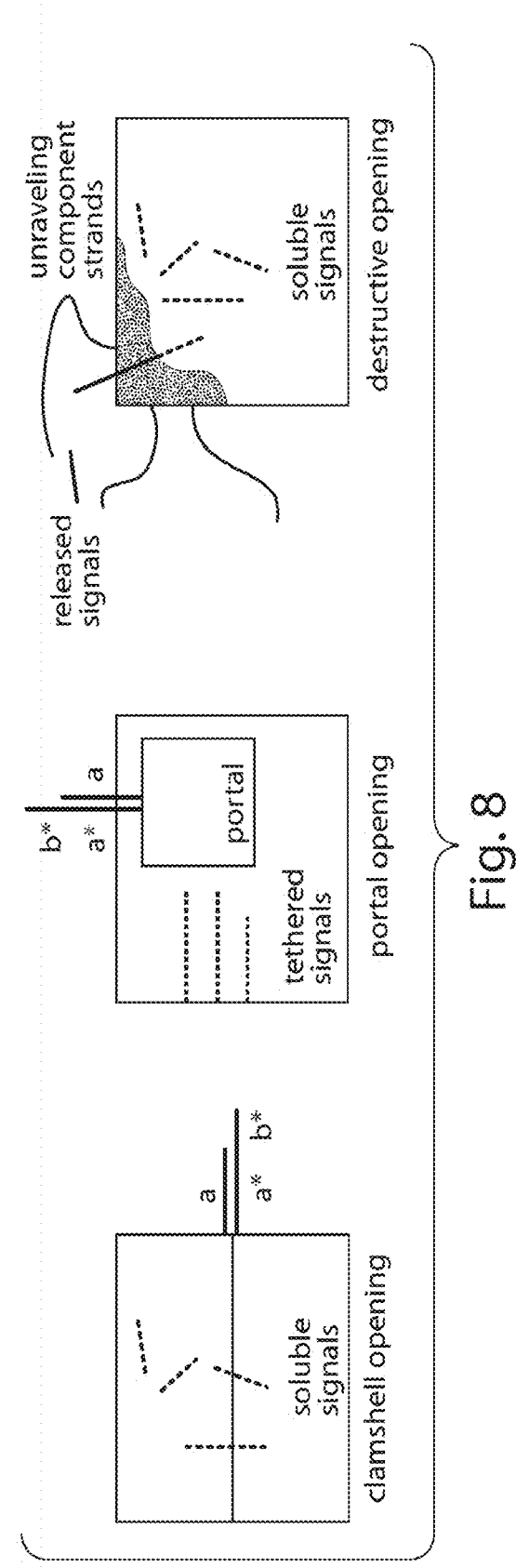
FIG. 8: Various embodiments include alternative mechanisms for opening the sealed container. Lid designs may be altered, or the container wall or a portion of it could be destroyed.

In various embodiments, containers can be designed to open with a mechanism other than a nucleic acid lid (FIG. 8). Possibilities include distortions of the lid concept and the destruction of the container or a portion of it by unraveling or disassembly. These openings may be random or non-random. For example, since the nucleic acid sequence used to generate the nucleic acid structure is known, the location of nucleic acid sequence at any given location on the structure can also be deduced. Accordingly, certain regions of the structure may be engineered to be susceptible to degradation, disassembly or unraveling. For example, certain regions may be engineered to have restriction endonuclease target sequences that may be acted upon to release contents of the structure upon interaction with the specific endonuclease.

Uses and Applications

Figure 9:
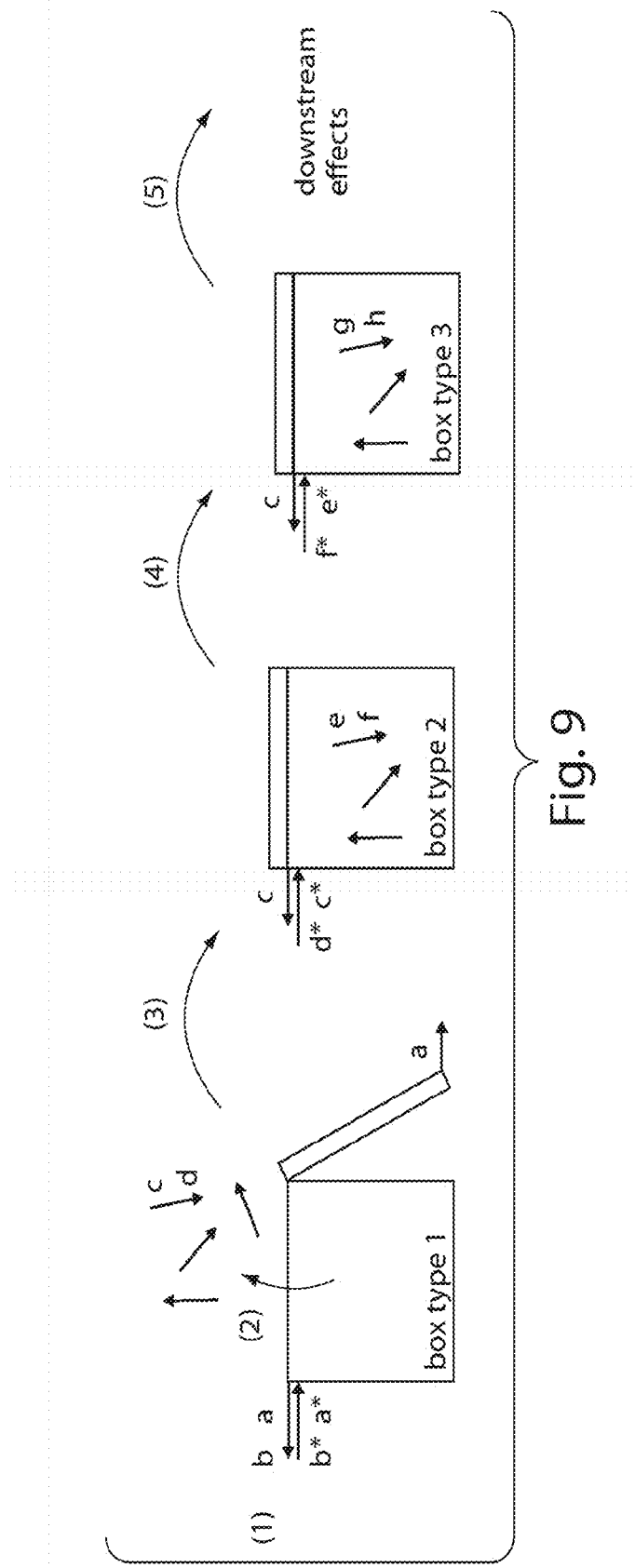
FIG. 9: Signals may be amplified to high levels via a cascading organization of individual amplifiers. (1) When box type 1 is opened, (2) it releases many copies of keys to box type 2, generating an amplification effect in itself. (3) Those keys in turn open box type 2, (4) which in turn when opened releases many keys for many copies of box type 3, (5) which in turn can have direct downstream effects or further amplification stages. It is to be understood that in addition or instead of keys, each structure may comprise nucleic acid input signals.

The invention contemplates that the systems and other compositions of the invention may be used in a variety of ways, including in vivo and ex-vivo uses, and biological and non-biological uses. As an example, they may be used for signal amplification. Utilizing the same structures as in FIG. 5, the release of a large number of pre-prepared signals (such as but not limited to nucleic acid signals) have the effect of an amplified response, particularly if such pre-prepared signals are incorporated into various layers of an amplification system. In contrast to systems in which each downstream signal must be generated independently and sometimes de novo by individual interaction with upstream signals, the described systems achieve at least two advantages. First, because released signals can be any length or complexity, and do not share any homology to the "key" signals that open the container, they represent a system with much less signal leakage potential. Second, because release signals were prepared ahead of time, response is very rapid, and independent of the kinetics of traditional signal-transduction systems. Such a system may be arranged in a cascading manner (FIG. 9), such that container type/stage 1 opens stage 2, releasing signals and/or keys to stage 3, and so on. Each "stage" is also referred to as "layer" herein. This results in many stages (or layers) of amplification. They could also be arranged with a feedback mechanism, such that some or all of stage 2 keys open stage 1 containers (cross-catalytic).

Figure 10:
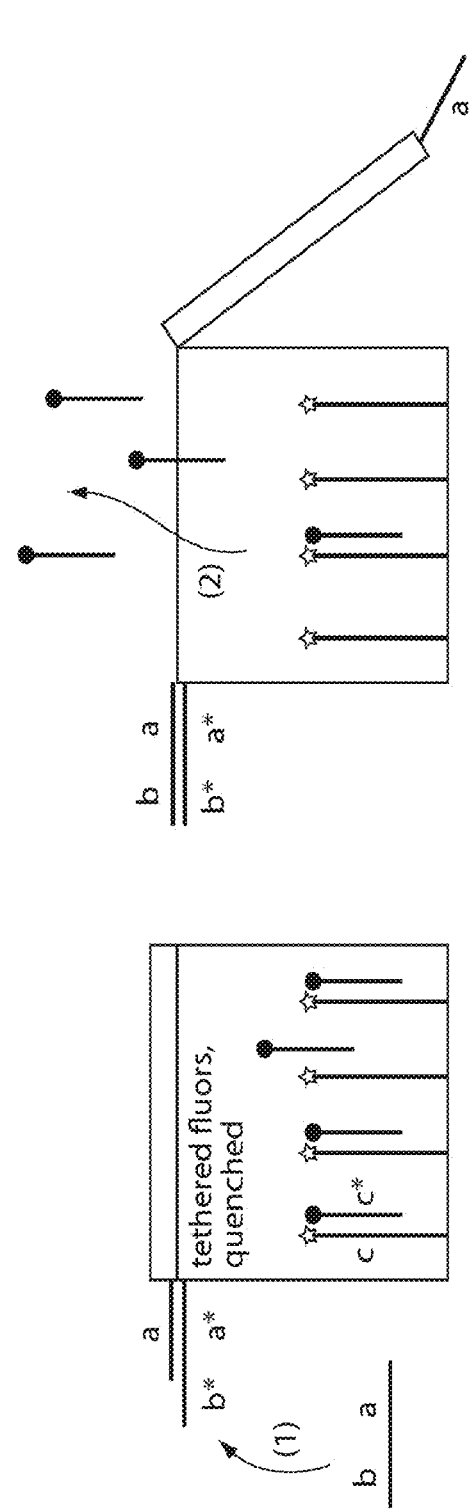
FIG. 10: Reactions can be controlled by controlling reactant concentration. Here, for example, nucleic acid strands comprising sequence "c" and fluors on their ends (red star) are tethered within a container. The container is also loaded with short complementary strands ("c*") with fluor quenchers at their ends. (1) While sealed, a dynamic equilibrium between bound and free quencher strands exists. Because the concentration of quencher strands is so high, virtually all fluor strands are hybridized to quencher strands, and fluorescence is almost completely quenched. When a signal triggers container opening, (2) quencher strands diffuse away when dissociated, and fluorescence is detected and/or increased. Accordingly, detection or increase in fluorescence is an indicator of the presence of the input signal "ba".

Enclosed assemblies also permit the control of reactions by means of controlling reactant concentration (FIG. 10). If a structure contains tethered fluorophores within it, and is loaded with free copies of a hybridizing strand holding a Resonance Energy Transfer (RET) fluorescent quencher, fluors will be quenched upon hybridization. The fluor-quencher strand pairs exist in a dynamic state, continuously hybridizing and dissociating (pair "c" with "c*" in figure). Given the high local quencher strand concentration in the enclosed box, the net on-rate of quenchers to fluors will be far higher than the off-rate, the latter not being concentration dependent. Upon opening of the lid, dissociated quenchers diffuse away, lowering the local concentration and net on-rate, with the effect of increased fluorescence. In general, any nucleic acid hybridization reaction has this concentration dependence of on-rate, but fixed off-rate, and thus the balance of can be controlled by sequestration and release. The systems of the invention may incorporate at any stage or layer one or more structures comprising detectable markers (or reporters) such as but not limited to fluorophores, FRET acceptor and donor pairs, fluorophore and quencher pairs, chromophores, and the like. In this way, the progression and amplification capacity of a system can be monitored.

Such amplification schemes have the potential to amplify a small environmental signal into a large output signal. Current dynamic DNA circuits can amplify signals approximately 100- to 1000-fold[9], and are limited by signal leakage. The spatial sequestration schemes and systems described herein can have much higher usable amplification capacity at least because of lower leakage rates. This makes them attractive candidates for bio-sensing applications, where biological signals or toxins might be detected at very low concentrations.

An embodiment such as that in FIG. 10 can also be used for biological imaging. Sequestration schemes may have applications in NMR/MRI or other non-optical systems, where contrast agents may be conditionally activated or displayed.

Finally, sequestration of agents such as drugs will have applications in conditional drug delivery to the body. Besides the traditional small-molecule drugs[3], the drugs could be nucleic acid strands designed to sense non-nucleic acid molecules, interact with each other, and control traditional drug molecules. There are a number of nucleic-acid therapeutics in current development that control or assert their effect via hybridization[10], and as such could benefit from the spatial sequestration described here.

It will be understood that the systems of the invention allow release of agents in vitro or in vivo in a controlled manner. Such control may be temporal control (e.g., when it is desired to release a number of agents in a co-ordinated including staggered manner). Such control allows for conditional release of agents only when input signals are available. Such control also allows for tempering or squelching of cascades by introducing an inhibitory or stop signal (either incorporated into the system such as in a nucleic acid structure or as an externally applied reagent).

The invention further contemplates use of the systems and compositions in computation. The sequestration of signals within larger structures allows for complex interactions within the structure while at the same time isolating this signal set from others, either free or sequestered in other structures. In enclosed containers (FIG. 7), this mimics an intracellular network or computer program subroutine, wherein internal signals are isolated in concentration and species from outside signals. Such a box could remain permanently closed, with only certain signals transduced through the walls to or from the soluble milieu or other containers.

Open versions are also possible (FIG. 4), in which most tethered species can interact only with adjacent species in the same container. Species tethered near the open ends of a container can reach other containers to transfer information.

Figure 11:
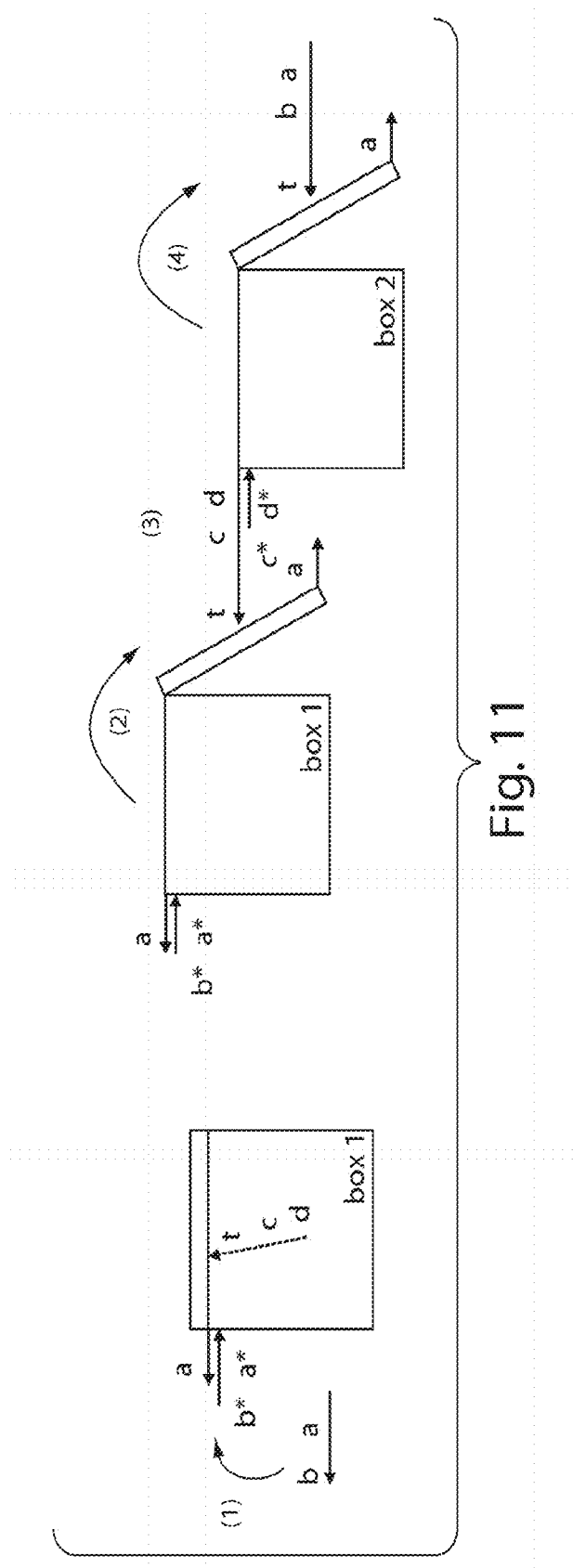
FIG. 11: Containers with lids can be made to aggregate upon triggering. Containers require the same lock-and-key mechanism to open, but each in turn contains a key for the alternating box type. (1) Upon binding an external key "ab" to the first lock, (2) it is opened to reveal a tethered key "dc" to the second box. The key binds robustly to the lock of the second container, both tethering them together and triggering lid opening. (4) The cycle continues with the exposure of original key "ab," leading to an alternating sequence of tethered box/key types.

The invention further contemplates use of the compositions and systems in triggered aggregation. In systems utilizing the ability of larger structures to sequester and protect smaller signals from reaction, the structures themselves can become part of the intended effect. For example, two types of boxes from FIG. 5 may be constructed, each of which holds internally the tethered key to the next box (FIG. 11). The structures are normally soluble in solution but do not interact. Upon triggering with a soluble or fixed key signal, the first box is opened, subsequently displaying the key to the second box, which in turn opens another copy of the first box, and so on. Depending on the geometrical design of the containers, their interaction might be termed "aggregation" (in the case of FIG. 11, a linear aggregation resembling "beads on a string") or, in a more refined implementation, assembly. Aggregated boxes may hold, in addition to alternating keys, other components related to drug delivery or other applications. More simple structures such as the folding tiles in FIG. 7 may be used in a similar manner.

The use of two container types in FIG. 11 allows for easier manufacturing and purification. Because the annealing process involves the exhibition of key strands to be sequestered, keys and their target locks must be manufactured separately. In the case shown, box 1 holds the key to box 2, and vice versa.

Figure 12:
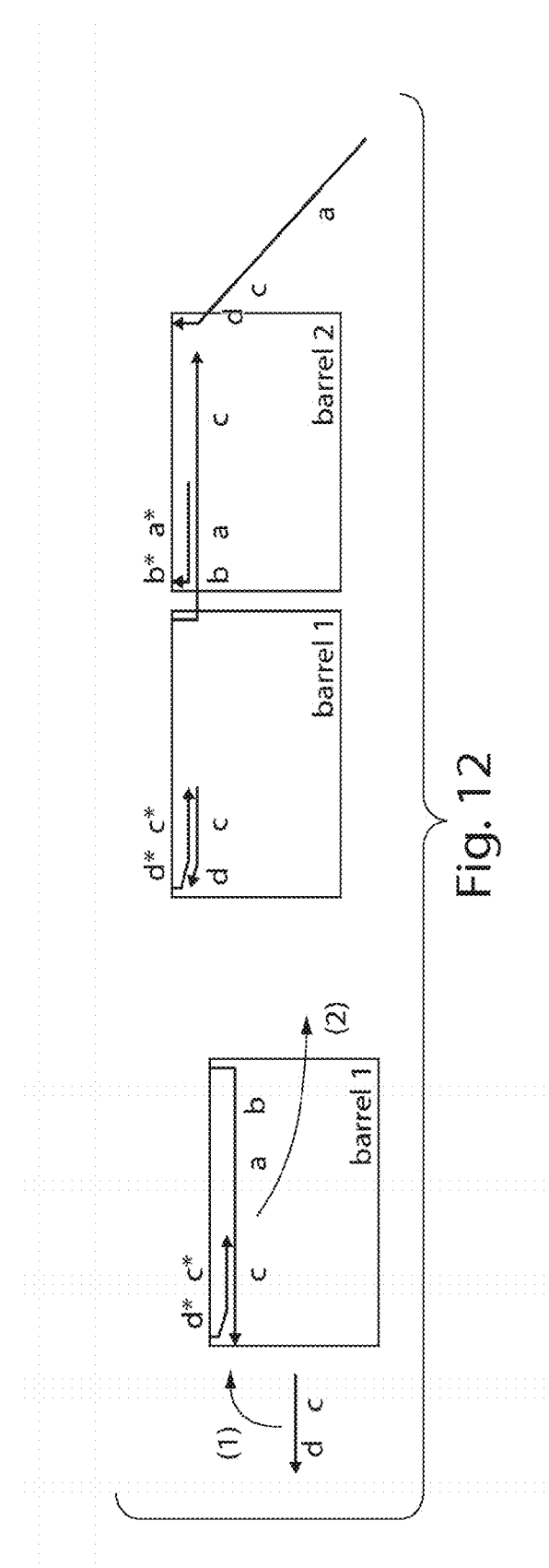
FIG. 12: Open containers can also be triggered to aggregate. (1) An external signal "cd" diffuses inside the first barrel, binding toehold "d*" and (2) detaching a temporary tether within. The signal strand "bac" remains permanently attached to the container at its other end, but is now able to reach outside and act as an input, via toehold "b*," to the second container type.

Open containers can also be used for triggered aggregation or assembly (FIG. 12). Key signals are again tethered inside the container, but also hybridized to fixed, internal strands (the "lock," with domains "c" and "d") to prevent them from reaching outside the container. Upon interaction with an initial trigger key, internal locks are opened and tethered keys allowed to reach beyond the open end. Elongated keys in turn attach to and unlock the next container, propagating the reaction.

Such aggregation systems can also be used in drug delivery, biosensing, or imaging applications, as all of these applications may be enabled by signal-concentrating mechanisms. The aggregation of small molecule or nucleic acid drugs can raise insignificant circulating drug concentrations to therapeutic levels, for example. The specified localization, timing, and sequence of aggregation can also enable more control over the delivery of therapeutics. Imaging may also be enabled by the concentration of a visible or other imaging probe constituting a detectable signal. Finally, the detection of ultra-low levels of biological signals in the environment will require accurate amplification to previously-unattained levels in order to make the signal detectable by machine or even naked eye.

In addition to the linear aggregation described, non-linear (branching) geometries can be attained by conditionally displaying multiple tethering "keys" from each container. Thus, dendritic and other organizations can be constructed.

EXAMPLES

Example 1. Container with Open Ends, Containing Signaling Circuitry

Figure 13:
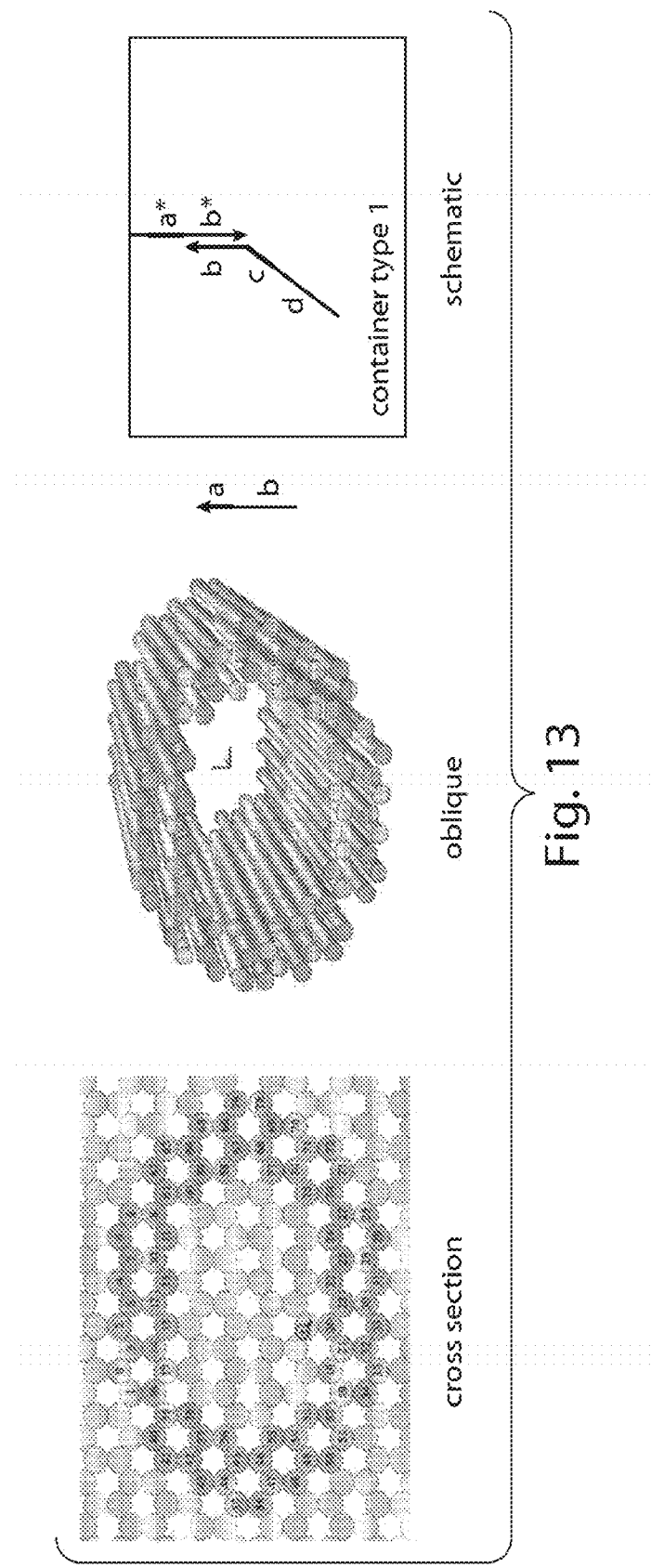
FIG. 13: Screenshots of the caDNAno software files for an example open-ended barrel, and a schematic corresponding to sequences in Table 1. Pointed ends of arrows refer to 3' ends of DNA.

FIG. 13 contains images of an example barrel-shaped container with open ends. The barrel was designed and constructed with typical three-dimensional DNA origami methods[6] and the caDNAno software[4]. Bound to approximately the center of the inside surface of the barrel is a short tether sequence ("a*b*" in FIG. 2) for the attachment of a signal strand. All sequences are listed in Table 1.

TABLE 1

Sequences of all strands required to form barrel with internal tether "a*b*," and signal sequence "dcb." This design requires an annealing program of approximately 72 hours, for example beginning with 3 minutes at 90 C., cooling at rates of 1 degree per 5-10 minutes to 60 C., then cooling at 1 degree per hour to room temperature. Annealing occurs at, for example, 12.5 mM MgCl2 concentrations in TE buffer.

| SEQ ID NO: | name | sequence |
|---|---|---|
| short ("staple") sequences (in DNA, given 5' to 3'): | | |
| SEQ ID NO: 1. | oligo1 | GCCCACGATTGTATGATGGTCA |
| SEQ ID NO: 2. | oligo2 | ACGGGGGATGGCTCTTTTGAGCCAGTT |
| SEQ ID NO: 3. | oligo3 | GTCACCAGTTTTCAAGGTCAGGAACCAC |
| SEQ ID NO: 4. | oligo4 | TGACGGACCGACTTCCAGTAGTATTCAT |
| SEQ ID NO: 5. | oligo5 | ATCACCTACCGAAAGCCCTAAAACATCGC |
| SEQ ID NO: 6. | oligo6 | CCTTTATCCGGAGATGGCATCTCATTTGG |
| SEQ ID NO: 7. | oligo7 | TAACCACATTTACAGACGCTCAATCGTCTG |
| SEQ ID NO: 8. | oligo8 | AAGGCTTGAACTGGCTCATTAGACGTTGTTGGGA |
| SEQ ID NO: 9. | oligo9 | TCATTTCAATTCACTACAAAGGTAATCACCAGGC |
| SEQ ID NO: 10. | oligo10 | AATAAATCAAAATTTCATCAAATTACATGGAAAC |
| SEQ ID NO: 11. | oligo11 | GTTTTGTGCCCCCTATGGCTTTTTACCGCAGAATG |
| SEQ ID NO: 12. | oligo12 | TGAAAATAGAAAGGTCAACAGCTTCATCTACCCAA |
| SEQ ID NO: 13. | oligo13 | TTAGTAAGTGCCCGGTGTACTGGTAATACGGAAAC |
| SEQ ID NO: 14. | oligo14 | TGGTGCTGGTCGTGCAGCCTAGGGTAATTCGGTTG |
| SEQ ID NO: 15. | oligo15 | AATACATACATAATACCCAAAGAAAAGATTAAGCC |
| SEQ ID NO: 16. | oligo16 | AGTACATTCATTCCGTAGATTTAGTTTGAGGAGCG |
| SEQ ID NO: 17. | oligo17 | GGGCTTAATTGAAAGTTCAGTCAAAAAAAAGTTAA |
| SEQ ID NO: 18. | oligo18 | CGGTATGAGCCGGGCGTCGGTACCGCAAAAAAGGA |

TABLE 1-continued

Sequences of all strands required to form barrel with internal tether "a*b*," and signal sequence "dcb." This design requires an annealing program of approximately 72 hours, for example beginning with 3 minutes at 90 C., cooling at rates of 1 degree per 5-10 minutes to 60 C., then cooling at 1 degree per hour to room temperature. Annealing occurs at, for example, 12.5 mM MgCl2 concentrations in TE buffer.

| SEQ ID NO: | name | sequence |
| --- | --- | --- |
| SEQ ID NO: 19. | oligo19 | CCAGAGCCTAATTTTAAGAGGACTTTTTCAAATAT |
| SEQ ID NO: 20. | oligo20 | GTGCTGTCCCAGTCTTTCAGTGAGGATCCAGCACG |
| SEQ ID NO: 21. | oligo21 | GTAAGAATTAGTCTTTAATGAAGGGAAGCAGACGA |
| SEQ ID NO: 22. | oligo22 | CAGAGATATAATAAACCTGCAGACGTATAACGTGC |
| SEQ ID NO: 23. | oligo23 | GTCAATACTCGTATCATGGAGCAAACAACATTCAG |
| SEQ ID NO: 24. | oligo24 | CAAATCATAAATTAGGGTAGCTCAATCAGCACCGC |
| SEQ ID NO: 25. | oligo25 | ACCGTTCCCAAGTTACAAAATAGTAACAAAATTAGA |
| SEQ ID NO: 26. | oligo26 | ATTATAGCAAAAATTTACCGCTTACCAGAACCAAGT |
| SEQ ID NO: 27. | oligo27 | CCGTAATGTCATACGCCTATTTTATTCTTCAAGAGAA |
| SEQ ID NO: 28. | oligo28 | ACAGGAAGTTGATATAGCATGTATTTTTTATATTTAAT |
| SEQ ID NO: 29. | oligo29 | GCTCAACATAGTTGATTTTTTAATTTAACAATTTCATTT |
| SEQ ID NO: 30. | oligo30 | AGCGTAACGATCTAAAGACAGCCATTAGGAGTTTAGTAC |
| SEQ ID NO: 31. | oligo31 | CTACAGAGGCTTTGAGACGAGGGTGAGAATCTCCAAAAA |
| SEQ ID NO: 32. | oligo32 | AAAATTGATTCAATAGTAGCATAACCTGTTTAGCGAGAGAT |
| SEQ ID NO: 33. | oligo33 | TGAAACTTATACTTGCCTGAGAGTCGAACCATTACATGTCT |
| SEQ ID NO: 34. | oligo34 | TTCGCGTGTAAACCTCAGGATTCTGGTGCCGGAAGTAAAAC |
| SEQ ID NO: 35. | oligo35 | AACAGCACCTTTACGAACCAGACCGGATTAATTCACAAAGT |
| SEQ ID NO: 36. | oligo36 | ATTTTAGATTGCTCTAGAGCTACATAGCTGTGAGTGAATAAC |
| SEQ ID NO: 37. | oligo37 | AGAAGAACTCAAACAACATCACTTACGGCTGGAGGTTCGCAC |
| SEQ ID NO: 38. | oligo38 | CAGGTCAGGATTAATGCTGTTTCCCTCTGTAAATCGTCGCTA |
| SEQ ID NO: 39. | oligo39 | CCTTTTTCGTCTTTTAACATAAATAGTTGCTATTTCCAACGC |
| SEQ ID NO: 40. | oligo40 | AGGCGCTTGTCCAGCTTTGATAGGTGAAGGAACCCCAAACTA |
| SEQ ID NO: 41. | oligo41 | AAAAGCCCATATGCGTTATACTTTTCGATCCAAGAATAATCG |
| SEQ ID NO: 42. | oligo42 | GCCTGTGCGGGTTAAGGGACAAGTTAAACGATGCTTCGTCTC |
| SEQ ID NO: 43. | oligo43 | TCCTGAGAAGTGTTTTTATGGAGGGATTGGCGCGTGCGCGCG |
| SEQ ID NO: 44. | oligo44 | AAAGAAGTTTTGCCCGGAATAATATAAAAGAAACGTTAGCAA |
| SEQ ID NO: 45. | oligo45 | ATTTTTGTTAAAGTACCGTGCGCTGCGCAACTGTTAAACCAC |
| SEQ ID NO: 46. | oligo46 | AAAGGTTAGAGGCAAAATTCTTTATAATTACTAGATTATTTT |
| SEQ ID NO: 47. | oligo47 | AAGAGTAATGAACGGACTTTTTCATGAGGCAGCGAAAAGGAA |
| SEQ ID NO: 48. | oligo48 | ATGAAACTACAGGATATAAACTTCCACTACGAAGGCACCATG |
| SEQ ID NO: 49. | oligo49 | TAAATATATTCAACTGAGATTTAGGAATACGGAACAAATCTA |
| SEQ ID NO: 50. | oligo50 | GCTGTCTTGTTCAGGTCCAGAACCGGAACAAAATCGTTTGCC |
| SEQ ID NO: 51. | oligo51 | ACCACATGACAAAATTTGTCATTTTGCACCAGAATCGCCATA |
| SEQ ID NO: 52. | oligo52 | CAGAGCCACGAGCCGCCACCCTCAGAACAGAGCCAAAACAAA |
| SEQ ID NO: 53. | oligo53 | CACCAGATACATAAAAATGGTTTACCAGGGGTCATAGCCCCC |

TABLE 1-continued

Sequences of all strands required to form barrel with internal tether "a*b*," and signal sequence "dcb." This design requires an annealing program of approximately 72 hours, for example beginning with 3 minutes at 90 C., cooling at rates of 1 degree per 5-10 minutes to 60 C., then cooling at 1 degree per hour to room temperature. Annealing occurs at, for example, 12.5 mM MgCl2 concentrations in TE buffer.

| SEQ ID NO: | name | sequence |
| --- | --- | --- |
| SEQ ID NO: 54. | oligo54 | CCTCATTAAAGCTTCCAGTTTATACCAACACTCATCTTTGAC |
| SEQ ID NO: 55. | oligo55 | CTCATCGAGAACAATTATCATGCCAGTAATAAAGTACCGACA |
| SEQ ID NO: 56. | oligo56 | GAAAGCGGCCTTGATCAGACTCATCTTTTCATAATCCGCCTC |
| SEQ ID NO: 57. | oligo57 | CTCATTTAACCGCCCCACCCTCAGAACCTCAGGAGTTAGCGG |
| SEQ ID NO: 58. | oligo58 | GGGCTTGAGATGGTGTACAACAGAGGCAAAAGAATGAAAGTA |
| SEQ ID NO: 59. | oligo59 | TAGCAGCCTTTACAAGACGGGCTTCTGACAAAGCGGATTGCA |
| SEQ ID NO: 60. | oligo60 | CATATTAGTTTAACGTCAAAAACCCTGAGAGCTTCGATTAAG |
| SEQ ID NO: 61. | oligo61 | TTGATGACATCGATAGCAGCATTTAGCGTATTCACCCACCCT |
| SEQ ID NO: 62. | oligo62 | AGTTAATCGTCTTTCCAGACGCAACGCCCTCAGTAGTGTATC |
| SEQ ID NO: 63. | oligo63 | ATCAGAAGTACCTTTTACATCTTGAATATAGCTGACCATCAA |
| SEQ ID NO: 64. | oligo64 | AGACTCCGAAACATACACTAAAAGCGCGAAACAAACTCTGAA |
| SEQ ID NO: 65. | oligo65 | GACTAAAGTGTACAAACGAGGGACCTGCTCCATGTAGTGAAT |
| SEQ ID NO: 66. | oligo66 | ACGACAGAATGGGACCTGCAACCAGCAGCCCACTATAAATCG |
| SEQ ID NO: 67. | oligo67 | GATAAGTACCAGTAATGTACCGTAACACTCAGCTTTGACAAC |
| SEQ ID NO: 68. | oligo68 | GGAAGTTAAATCAAAAGAAAACAAAATTATATAATGAATTAT |
| SEQ ID NO: 69. | oligo69 | AGCGAGTGGCGGATTGACCGTTATCGGCGTTAATACCCAAAA |
| SEQ ID NO: 70. | oligo70 | TTGCTAAACAACTTAACAACTAAGACAGGCGGGATCGTCACC |
| SEQ ID NO: 71. | oligo71 | CATTTTAAATGAAAATCTATTGTAAAGGCGCATCGGGGGAT |
| SEQ ID NO: 72. | oligo72 | GATTCGCCTGATTGCTGGGAGAATACCCCGGATTGTATAAGC |
| SEQ ID NO: 73. | oligo73 | GAACCGAACACCTAAAACGAAGGAGATTTGTATCAGTAAATT |
| SEQ ID NO: 74. | oligo74 | CTGAGTAATCATAGATACATTTCGCAAAGGTCATTCAATTAT |
| SEQ ID NO: 75. | oligo75 | AACAAAGGGAAGGAGCTGGCGAAAGTATGAAAGGTAGAGCC |
| SEQ ID NO: 76. | oligo76 | CCTGATTTAGAACCTACCATAGAAATTGTTTGCCCAATAGAT |
| SEQ ID NO: 77. | oligo77 | TAACCCACAAGAATTGAGTATACTGAACATGAAAAACAAATA |
| SEQ ID NO: 78. | oligo78 | TTTAAATTCTGGCCCAGCTTTCATCAACATTAAGTAAAAATAA |
| SEQ ID NO: 79. | oligo79 | TGAGAATAGACGCTCCCTCATATATTTTAAATGTAGATAGCTT |
| SEQ ID NO: 80. | oligo80 | TACAGCGTGCCAAGCACGACGAAGCATCAAATCAACATCAGCT |
| SEQ ID NO: 81. | oligo81 | CAAGTGTAGCGGTCACGCTATAAAGCGAAAAGCACCGTGAACC |
| SEQ ID NO: 82. | oligo82 | CTTGCTTTAGAATCCTTGAAATAATTGCATATGCAACTAAAGT |
| SEQ ID NO: 83. | oligo83 | AAACACCGGAATCACTACCGACCCAATCGGGCTTAGTGTTTATC |
| SEQ ID NO: 84. | oligo84 | AGAAAGGTTCAACGATACTTTTGCGGGAAAACATTCATAAAGCTAA |
| SEQ ID NO: 85. | oligo85 | AATTGAGAGTTGGCACCTTGCTGAACCTAGGGTTTCAAGGCGATTA |
| SEQ ID NO: 86. | oligo86 | CTGCCGTAGATGACGCGGTCAGTATTCAGCAGCTTAACCAATAGGAA |
| SEQ ID NO: 87. | oligo87 | ACCGAGCGGCCAGCCATGTTTACCAGTGGTGAAGGGCGAACACTGCGC |
| SEQ ID NO: 88. | oligo88 | CGATGGAAGATAATTTGTGAGAGCGCGAACTGATCGAACCACAATGTG |

TABLE 1-continued

Sequences of all strands required to form barrel with internal tether "a*b*," and signal sequence "dcb." This design requires an annealing program of approximately 72 hours, for example beginning with 3 minutes at 90 C., cooling at rates of 1 degree per 5-10 minutes to 60 C., then cooling at 1 degree per hour to room temperature. Annealing occurs at, for example, 12.5 mM MgCl2 concentrations in TE buffer.

| SEQ ID NO: | name | sequence |
|---|---|---|
| SEQ ID NO: 89. | oligo89 | ACCGCACATCGTATTTTAGCTTAAATCAAGATAATTTGAAACCTGACT |
| SEQ ID NO: 90. | oligo90 | GCAGCAGGTGCCATCCCACGGCGGTTGTTCGTTAGAATCAGGTCGCTG |
| SEQ ID NO: 91. | oligo91 | CTTTACGATGAACGGCTATCATGGTCAATTAACAAGCAAAAATAGGTC |
| SEQ ID NO: 92. | oligo92 | TCTACTCAGAGATGACCCGTTGGGTAATCTTATGCACCCAGCTACAAT |
| SEQ ID NO: 93. | oligo93 | CGTGCCTCATACCAGACGCATTTGCCGCCAGCAGTTGGGCTTCTCACG |
| SEQ ID NO: 94. | oligo94 | CATCAGCGGAATCAGTGAGGCTTAACCGCCCTCAGTCAGGGATTCCACA |
| SEQ ID NO: 95. | oligo95 | CTAAACGACGAGCCCAGCGGCAGTGTCGTGGCGAAAAGGGATCTCAGGG |
| SEQ ID NO: 96. | oligo96 | AGATTATTTTGCGCAAGGCAAAGAATTTCCAATAAATGTGTGAAGATGA |
| SEQ ID NO: 97. | oligo97 | GAGAGGCCAATCAAGAACAAGAAAAAGGTGGCAACAGTTTATGGCGAC |
| SEQ ID NO: 98. | oligo98 | AAAATCTTAAGCAATAAAGCCTAATAGAAGGGTGTATGATATTACCTGA |
| SEQ ID NO: 99. | oligo99 | AGCGGGATCAATCCGCCGGGCCAACCAGCTTGCCTCGGTTTATGAATAA |
| SEQ ID NO: 100. | oligo100 | TATCGGCCGTTTTTGATTGCCCGACCAGGAACCCTTCTCCGTCCCGGAA |
| SEQ ID NO: 101. | oligo101 | TTTCATAGAATTAAGAAGGCTTATCCGAGCAAGCGAAT GACCAACAGTATTTCACACGTCAACTCATACAACTCTGATC (note: oligo101 contains tether "a*b*") |
| SEQ ID NO: 102. | oligo102 | TTTGCGGCATCATACGAACGAATATAACGTTTTAATGAATATAGAGAGT |
| SEQ ID NO: 103. | oligo103 | ACTATGGTTGCTTTAGGAGGCCGCGGTCCTTGCTGGTAATATAATACTT |
| SEQ ID NO: 104. | oligo104 | AATATACCGCGCAGAGGCGTGAATAATGTTTAACGTCGACAAGATAATA |
| SEQ ID NO: 105. | oligo105 | AGGAAGCCAAATGCTAAGAGCCGAAGCCCTTTTTAAAGAACTATAGCGT |
| SEQ ID NO: 106. | oligo106 | ATCAATATCTGGTCGAAGGTTTTACGCCGCGATCGGTGCGGGTTATCAT |
| SEQ ID NO: 107. | oligo107 | TTTCCTTGCAGATGCCACTCTGTCACGGGGAAAGCCGGATAGCGGCCAA |
| SEQ ID NO: 108. | oligo108 | AAATCCCGTAGATTTTCAGGGAAGGGTGTTTGGAAAAACATCTACAATGC |
| SEQ ID NO: 109. | oligo109 | AAAAAAACTGCTCAGAAACAGCCGGAAAGCCGCCATAACGCCCAAATAT |
| SEQ ID NO: 110. | oligo110 | TTGCGAGTGGGATTCAGTCAGTGCCTTGACCAACTCCATTAAACGGGTA |
| SEQ ID NO: 111. | oligo111 | GCGGCCAATCGTTATCGACATGCCTTTAGTGATGACCGGCCAAGGTTTC |
| SEQ ID NO: 112. | oligo112 | GCTACAGTTAGACAGGAAAAAAATATTACCGCCAGACGCAAACACCGAG |
| SEQ ID NO: 113. | oligo113 | TGTACAACGGCATCTCGTCATAAACATTGGGTAAGAGCACACGTCAGCG |
| SEQ ID NO: 114. | oligo114 | TCCAGCGTGCCGGTAGTCACAGTTCCGGCATACCTACATTTTTTGGCAG |
| SEQ ID NO: 115. | oligo115 | GCAAAAAGGTAAATTTAGAAGAGAAGAGTCAATAGTGAATACAAGGATA |
| SEQ ID NO: 116. | oligo116 | AACCATCCTGTTGATATAAGTATAGCCCCCGACAAGCTTTCGTAGTAAT |
| SEQ ID NO: 117. | oligo117 | TAAAGGCTCGGTCGAGGCTCCGAATGCCTGTAGAATCCTCATACAGGCG |
| SEQ ID NO: 118. | oligo118 | ACCGTACGCCTTGATACCGATAGTTGCGGGAATAGCCAGGCGAAATACG |
| SEQ ID NO: 119. | oligo119 | AGATCGCAACAAACAACAACCTTAAAAACAAATCAGGTCGAGGTGCCGT |
| SEQ ID NO: 120. | oligo120 | GAACCCTGAAAGGATAGACTTTCTGACCTGAAAGCATTCACCGCCCCCT |
| SEQ ID NO: 121. | oligo121 | ACAGAGGTGAGGACTCGAATGCCCCCGATTTAGAGCTTGTGCCCCGGGT |
| SEQ ID NO: 122. | oligo122 | TAATGAAGAGGCTGGGTTTTGTGTAGCATAGCAAGCCCAATATTTCTTA |

TABLE 1-continued

Sequences of all strands required to form barrel with internal tether "a*b*," and signal sequence "dcb." This design requires an annealing program of approximately 72 hours, for example beginning with 3 minutes at 90 C., cooling at rates of 1 degree per 5-10 minutes to 60 C., then cooling at 1 degree per hour to room temperature. Annealing occurs at, for example, 12.5 mM MgCl2 concentrations in TE buffer.

| SEQ ID NO: | name | sequence |
|---|---|---|
| SEQ ID NO: 123. | oligo123 | TCGCTAATCTAAAGAGCACTAACAACTGAACGTTATTAATTAAAACAGA |
| SEQ ID NO: 124. | oligo124 | TTGAAAGCATAAGGATAAATTGTGTCGACGAGAAAAACCGGACACCATT |
| SEQ ID NO: 125. | oligo125 | TAACGAGAACCTCCCAAGACAAAGAACGTTAATGGCAGGGAAAAGAACG |
| SEQ ID NO: 126. | oligo126 | AGTAACAATGAATTTTCTGTATTTCGTCGCCGTCGAGAGGCAGAAGTTT |
| SEQ ID NO: 127. | oligo127 | AAAACGAAAATCAGTAAGCAGATAGCCGCAATAATTTTAACAAAATAGC |
| SEQ ID NO: 128. | oligo128 | ATCAACGAGCCAGCAAAATCAGAGCCATGGAAGAAAACATTATTACAGG |
| SEQ ID NO: 129. | oligo129 | ACGGGAGCACCAGAAATTACCTTATGCGCGTTAATACCGTCAAATTATT |
| SEQ ID NO: 130. | oligo130 | ACGCCAACAACGCTCATAAATTCAGAAGCCTAAATCGAGAAATCGACTA |
| SEQ ID NO: 131. | oligo131 | TAATTTTTTCACGTGCCTTTACATAACCGATATATCGCTTTTCATCGGA |
| SEQ ID NO: 132. | oligo132 | CGAGGCGGGAATCACAGGTCTTACCAGTATAAAGCCATGTAAAAACCGA |
| SEQ ID NO: 133. | oligo133 | ATTTTAAGCCCTGAAATCCGCCGCAGACGGTCAATAGGACAGATCTTGA |
| SEQ ID NO: 134. | oligo134 | ATTTCAACTTTAATTTGAGGCTCGGCATTTTCGTGGCAAGGCAGTTTTA |
| SEQ ID NO: 135. | oligo135 | CAATAATTTAAACTACTGCGGAATCGTAGACTGGGGCATGAACGTAGAA |
| SEQ ID NO: 136. | oligo136 | TGTAAATGCTGATGCAAATCGTGTGATGAAGCCGAACCTCCCGACTTGC |
| SEQ ID NO: 137. | oligo137 | TTAAAGGTTTAGGCACCAGACGACGATACTATCATTATCAACAATAGAT |
| SEQ ID NO: 138. | oligo138 | AACGGAAATAATATCCCATCCAAGTCCTTAGAAAATTCATCAAAAACCA |
| SEQ ID NO: 139. | oligo139 | TTAAGCATCTTACAAGAAACAGAGAGACAGAGGGATTTTTTTTTATCC |
| SEQ ID NO: 140. | oligo140 | CCTCAGAGTTAAAGTAATTCTCTAATGCAGAACGCCCAATCAACGGGTA |
| SEQ ID NO: 141. | oligo141 | CGAGCATGTAGAAAGCCTGTTAACCCTCGGCATAGCGTTTGCGTAGCGC |
| SEQ ID NO: 142. | oligo142 | AAGGAGCATGGCTATACGTGGCACAGACATGGATTCACACCCATGCGCC |
| SEQ ID NO: 143. | oligo143 | CATTAAACGCCAAATCAACTAATGCAGAGCCGCCGCCAGCAACGAACTA |
| SEQ ID NO: 144. | oligo144 | TTATTAGTAAGAGCCGCCAAAAGGAATTGCCACCAACGATTGCAGTTTA |
| SEQ ID NO: 145. | oligo145 | ACCATTAAATTATCAAATTGACAGGAGGCATTGTGACGAGTATCGCCTG |
| SEQ ID NO: 146. | oligo146 | AACAGCATTGTAGCCCAGAACCGCTCATGAAAAACGATTAATCATTGC |
| SEQ ID NO: 147. | oligo147 | TAATTTAGGAAACGAACAAAGGCCCAATGTATTCTGCGCATTGAGAGAA |
| SEQ ID NO: 148. | oligo148 | TCACAGTAGGTGGACAATCGGCGAAACGGAAAAAGGGGGGTTTGGTGCT |
| SEQ ID NO: 149. | oligo149 | AAAATTCGGGGACGAAAGCGCCATTCGCGAGAATCAAACAATTCAGATG |
| SEQ ID NO: 150. | signal "dcb" | CACACTCCTACTCCAACATCCACCCTTcascGATCAGAGTTGTATGAGTTG | long ("scaffold") sequence:

| SEQ ID NO: 151. | | GAATTCGAGCTCGGTACCCGGGGATCCTCAACTGTGAGGAGGCTCAC<br>GGACGCGAAGAACAGGCACGCGTGCTGGCAGAAACCCCGGTATGAC<br>CGTGAAAACGGCCCGCCGCATTCTGGCCGCAGCACCACAGAGTGCACA<br>GGCGCGCAGTGACACTGCGCTGGATCGTCTGATGCAGGGGGCACCGG<br>CACCGCTGGCTGCAGGTAACCCGGCATCTGATGCCGTTAACGATTTGC<br>TGAACACACCAGTGTAAGGGATGTTTATGACGAGCAAAGAAACCTTT<br>ACCCATTACCAGCCGCAGGGCAACAGTGACCCGGCTCATACCGCAACC<br>GCGCCCGGCGGATTGAGTGCGAAAGCGCCTGCAATGACCCCGCTGAT<br>GCTGGACACCTCCAGCCGTAAGCTGGTTGCGTGGGATGGCACCACCGA<br>CGGTGCTGCCGTTGGCATTCTTGCGGTTGCTGCTGACCAGACCAGCAC<br>CACGCTGACGTTCTACAAGTCCGGCACGTTCCGTTATGAGGATGTGCT |

TABLE 1-continued

Sequences of all strands required to form barrel with internal tether "a*b*," and signal sequence "dcb." This design requires an annealing program of approximately 72 hours, for example beginning with 3 minutes at 90 C., cooling at rates of 1 degree per 5-10 minutes to 60 C., then cooling at 1 degree per hour to room temperature. Annealing occurs at, for example, 12.5 mM MgCl2 concentrations in TE buffer.

| SEQ ID NO: | name | sequence |
|---|---|---|
| | | CTGGCCGGAGGCTGCCAGCGACGAGACGAAAAAACGGACCGCGTTTG |
| | | CCGGAACGGCAATCAGCATCGTTTAACTTTACCCTTCATCACTAAAG |
| | | GCCGCCTGTGCGGCTTTTTTTACGGGATTTTTTTATGTCGATGTACAC |
| | | AACCGCCCAACTGCTGGCGGCAAATGAGCAGAAATTTAAGTTTGATC |
| | | CGCTGTTTCTGCGTCTCTTTTTCCGTGAGAGCTATCCCTTCACCACGG |
| | | AGAAAGTCTATCTCTCACAAATTCCGGGACTGGTAAACATGGCGCTG |
| | | TACGTTTCGCCGATTGTTTCCGGTGAGGTTATCCGTTCCCGTGGCGGC |
| | | TCCACCTCTGAAAGCTTGGCACTGGCCGTCGTTTTACAACGTCGTGAC |
| | | TGGGAAAACCCTGGCGTTACCCAACTTAATCGCCTTGCAGCACATCCC |
| | | CCTTTCGCCAGCTGGCGTAATAGCGAAGAGGCCCGCACCGATCGCCCT |
| | | TCCCAACAGTTGCGCAGCCTGAATGGCGAATGGCGCTTTGCCTGGTTT |
| | | CCGGCACCAGAAGCGGTGCCGGAAAGCTGGCTGGAGTGCGATCTTCC |
| | | TGAGGCCGATACTGTCGTCGTCCCCTCAAACTGGCAGATGCACGGTTA |
| | | CGATGCGCCCATCTACACCAACGTGACCTATCCCATTACGGTCAATCC |
| | | GCCGTTTGTTCCCACGGAGAATCCGACGGGTTGTTACTCGCTCACATT |
| | | TAATGTTGATGAAAGCTGGCTACAGGAAGGCCAGACGCGAATTATTT |
| | | TTGATGGCGTTCCTATTGGTTAAAAAATGAGCTGATTTAACAAAAAT |
| | | TTAATGCGAATTTTAACAAAATATTAACGTTTACAATTTAAATATTT |
| | | GCTTATACAATCTTCCTGTTTTTGGGGCTTTTCTGATTATCAACCGGG |
| | | GTACATATGATTGACATGCTAGTTTTACGATTACCGTTCATCGATTC |
| | | TCTTGTTTGCTCCAGACTCTCAGGCAATGACCTGATAGCCTTTGTAGA |
| | | TCTCTCAAAAATAGCTACCCTCTCCGGCATTAATTTATCAGCTAGAAC |
| | | GGTTGAATATCATATTGATGGTGATTTGACTGTCTCCGGCCTTTCTC |
| | | ACCCTTTTGAATCTTTACCTACACATTACTCAGGCATTGCATTTAAA |
| | | ATATATGAGGGTTCTAAAAATTTTTATCCTTGCGTTGAAATAAAGGC |
| | | TTCTCCCGCAAAAGTATTACAGGGTCATAATGTTTTTGGTACAACCG |
| | | ATTTAGCTTTATGCTCTGAGGCTTTATTGCTTAATTTTGCTAATTCT |
| | | TTGCCTTGCCTGTATGATTTATTGGATGTTAATGCTACTACTATTAG |
| | | TAGAATTGATGCCACCTTTTCAGCTCGCGCCCCAAATGAAAATATAG |
| | | CTAAACAGGTTATTGACCATTTGCGAAATGTATCTAATGGTCAAACT |
| | | AAATCTACTCGTTCGCAGAATTGGGAATCAACTGTTATATGGAATGA |
| | | AACTTCCAGACACCGTACTTTAGTTGCATATTTAAAACATGTTGAGC |
| | | TACAGCATTATATTCAGCAATTAAGCTCTAAGCCATCCGCAAAAATG |
| | | ACCTCTTATCAAAAGGAGCAATTAAAGGTACTCTCTAATCCTGACCT |
| | | GTTGGAGTTTGCTTCCGGTCTGGTTCGCTTTGAAGCTCGAATTAAAA |
| | | CGCGATATTTGAAGTCTTTCGGGCTTCCTCTTAATCTTTTTGATGCA |
| | | ATCCGCTTTGCTTCTGACTATAATAGTCAGGGTAAAGACCTGATTTT |
| | | TGATTTATGGTCATTCTCGTTTTCTGAACTGTTTAAAGCATTTGAGG |
| | | GGGATTCAATGAATATTTATGACGATTCCGCAGTATTGGACGCTATC |
| | | CAGTCTAAACATTTTACTATTACCCCCTCTGGCAAAACTTCTTTTGCA |
| | | AAAGCCTCTCGCTATTTTGGTTTTTATCGTCGTCTGGTAAACGAGGG |
| | | TTATGATAGTGTTGCTCTTACTATGCCTCGTAATTCCTTTTGGCGTT |
| | | ATGTATCTGCATTAGTTGAATGTGGTATTCCTAAATCTCAACTGATG |
| | | AATCTTTCTACCTGTAATAATGTTGTTCCGTTAGTTCGTTTTATTAA |
| | | CGTAGATTTTTCTTCCCAACGTCCTGACTGGTATAATGAGCCAGTTCT |
| | | TAAAATCGCATAAGGTAATTCACAATGATTAAAGTTGAAATTAAACC |
| | | ATCTCAAGCCCAATTTACTACTCGTTCTGGTGTTTCTCGTCAGGGCAA |
| | | GCCTTATTCACTGAATGAGCAGCTTTGTTACGTTGATTTGGGTAATG |
| | | AATATCCGGTTCTTGTCAAGATTACTCTTGATGAAGGTCAGCCAGCC |
| | | TATGCGCCTGGTCTGTACACCGTTCATCTGTCCTCTTTCAAAGTTGGT |
| | | CAGTTCGGTTCCCTTATGATTGACCGTCTGCGCCTCGTTCCGGCTAAG |
| | | TAACATGGAGCAGGTCGCGGATTTCGACACAATTTATCAGGCGATGA |
| | | TACAAATCTCCGTTGTACTTTGTTTCGCGCTTGGTATAATCGCTGGG |
| | | GGTCAAAGATGAGTGTTTTAGTGTATTCTTTTGCCTCTTTCGTTTTA |
| | | GGTTGGTGCCTTCGTAGTGGCATTACGTATTTTACCCGTTTAATGGA |
| | | AACTTCCTCATGAAAAGTCTTTAGTCCTCAAAGCCTCTGTAGCCGT |
| | | TGCTACCCTCGTTCCGATGCTGTCTTTCGCTGCTGAGGGTGACGATCC |
| | | CGCAAAAGCGGCCTTTAACTCCCTGCAAGCCTCAGCGACCGAATATAT |
| | | CGGTTATGCGTGGGCGATGGTTGTTGTCATTGTCGGCGCAACTATCG |
| | | GTATCAAGCTGTTTAAGAAATTCACCTCGAAAGCAAGCTGATAAACC |
| | | GATACAATTAAAGGCTCCTTTTGGAGCCTTTTTTTTGGAGATTTTCA |
| | | ACGTGAAAAAATTATTATTCGCAATTCCTTTAGTTGTTCCTTTCTAT |
| | | TCTCACTCCGCTGAAACTGTTGAAAGTTGTTTAGCAAAATCCCATAC |
| | | AGAAAATTCATTTACTAACGTCTGGAAAGACGACAAAACTTTAGATC |
| | | GTTACGCTAACTATGAGGGCTGTCTGTGGAATGCTACAGGCGTTGTA |
| | | GTTTGTACTGGTGACGAAACTCAGTGTTACGGTACATGGGTTCCTAT |
| | | TGGGCTTGCTATCCCTGAAAATGAGGGTGGTGGCTCTGAGGGTGGCG |
| | | GTTCTGAGGGTGGCGGTTCTGAGGGTGGCGGTACTAAACCTCCTGAG |
| | | TACGGTGATACACCTATTCCGGGCTATACTTATATCAACCCTCTCGAC |
| | | GGCACTTATCCGCCTGGTACTGAGCAAAACCCCGCTAATCCTAATCCT |

TABLE 1-continued

Sequences of all strands required to form barrel with internal tether "a*b*," and signal sequence "dcb." This design requires an annealing program of approximately 72 hours, for example beginning with 3 minutes at 90 C., cooling at rates of 1 degree per 5-10 minutes to 60 C., then cooling at 1 degree per hour to room temperature. Annealing occurs at, for example, 12.5 mM MgCl2 concentrations in TE buffer.

| SEQ ID NO: | name | sequence |
|---|---|---|
| | | TCTCTTGAGGAGTCTCAGCCTCTTAATACTTTCATGTTTCAGAATAA |
| | | TAGGTTCCGAAATAGGCAGGGGGCATTAACTGTTTATACGGGCACTG |
| | | TTACTCAAGGCACTGACCCCGTTAAAACTTATTACCAGTACACTCCTG |
| | | TATCATCAAAAGCCATGTATGACGCTTACTGGAACGGTAAATTCAGA |
| | | GACTGCGCTTTCCATTCTGGCTTTAATGAGGATTTATTTGTTTGTGA |
| | | ATATCAAGGCCAATCGTCTGACCTGCCTCAACCTCCTGTCAATGCTGG |
| | | CGGCGGCTCTGGTGGTGGTTCTGGTGGCGGCTCTGAGGGTGGTGGCT |
| | | CTGAGGGTGGCGGTTCTGAGGGTGGCGGCTCTGAGGGAGGCGGTTCC |
| | | GGTGGTGGCTCTGGTTCCGGTGATTTTGATTATGAAAAGATGGCAAA |
| | | CGCTAATAAGGGGGCTATGACCGAAAATGCCGATGAAAACGCGCTAC |
| | | AGTCTGACGCTAAAGGCAAACTTGATTCTGTCGCTACTGATTACGGT |
| | | GCTGCTATCGATGGTTTCATTGGTGACGTTTCCGGCCTTGCTAATGG |
| | | TAATGGTGCTACTGGTGATTTTGCTGGCTCTAATTCCCAAATGGCTC |
| | | AAGTCGGTGACGGTGATAATTCACCTTTAATGAATAATTTCCGTCAA |
| | | TATTTACCTTCCCTCCCTCAATCGGTTGAATGTCGCCCTTTTGTCTTT |
| | | GGCGCTGGTAAACCATATGAATTTTCTATTGATTGTGACAAAATAAA |
| | | CTTATTCCGTGGTGTCTTTGCGTTTCTTTTATATGTTGCCACCTTTAT |
| | | GTATGTATTTTCTACGTTTGCTAACATACTGCGTAATAAGGAGTCTT |
| | | AATCATGCCAGTTCTTTTGGGTATTCCGTTATTATTGCGTTTCCTCGG |
| | | TTTCCTTCTGGTAACTTTGTTCGGCTATCTGCTTACTTTTCTTAAAAA |
| | | GGGCTTCGGTAAGATAGCTATTGCTATTTCATTGTTTCTTGCTCTTA |
| | | TTATTGGGCTTAACTCAATTCTTGTGGGTTATCTCTCTGATATTAGC |
| | | GCTCAATTACCCTCTGACTTTGTTCAGGGTGTTCAGTTAATTCTCCCG |
| | | TCTAATGCGCTTCCCTGTTTTTATGTTATTCTCTCTGTAAAGGCTGCT |
| | | ATTTTCATTTTTGACGTTAAACAAAAAATCGTTTCTTATTTGGATTG |
| | | GGATAAATAATATGGCTGTTTATTTTGTAACTGGCAAATTAGGCTCT |
| | | GGAAAGACGCTCGTTAGCGTTGGTAAGATTCAGGATAAAATTGTAGC |
| | | TGGGTGCAAAATAGCAACTAATCTTGATTTAAGGCTTCAAAACCTCC |
| | | CGCAAGTCGGGAGGTTCGCTAAAACGCCTCGCGTTCTTAGAATACCG |
| | | GATAAGCCTTCTATATCTGATTTGCTTGCTATTGGGCGCGGTAATGA |
| | | TTCCTACGATGAAAATAAAAACGGCTTGCTTGTTCTCGATGAGTGCG |
| | | GTACTTGGTTTAATACCCGTTCTTGGAATGATAAGGAAAGACAGCCG |
| | | ATTATTGATTGGTTTCTACATGCTCGTAAATTAGGATGGGATATTAT |
| | | TTTTCTTGTTCAGGACTTATCTATTGTTGATAAACAGGCGCGTTCTG |
| | | CATTAGCTGAACATGTTGTTTATTGTCGTCGTCTGGACAGAATTACT |
| | | TTACCTTTTGTCGGTACTTTATATTCTCTTATTACTGGCTCGAAAAT |
| | | GCCTCTGCCTAAATTACATGTTGGCGTTGTTAAATATGGCGATTCTC |
| | | AATTAAGCCCTACTGTTGAGCGTTGGCTTTATACTGGTAAGAATTTG |
| | | TATAACGCATATGATACTAAACAGGCTTTTTCTAGTAATTATGATTC |
| | | CGGTGTTTATTCTTATTTAACGCCTTATTTATCACACGGTCGGTATT |
| | | TCAAACCATTAAATTTAGGTCAGAAGATGAAATTAACTAAAATATAT |
| | | TTGAAAAAGTTTTCTCGCGTTCTTTGTCTTGCGATTGGATTTGCATC |
| | | AGCATTTACATATAGTTATATAACCCAACCTAAGCCGGAGGTTAAAA |
| | | AGGTAGTCTCTCAGACCTATGATTTTGATAAATTCACTATTGACTCT |
| | | TCTCAGCGTCTTAATCTAAGCTATCGCTATGTTTTCAAGGATTCTAA |
| | | GGGAAAATTAATTAATAGCGACGATTTACAGAAGCAAGGTTATTCAC |
| | | TCACATATATTGATTTATGTACTGTTTCCATTAAAAAAGGTAATTCA |
| | | AATGAAATTGTTAAATGTAATTAATTTTGTTTTCTTGATGTTTGTTT |
| | | CATCATCTTCTTTTGCTCAGGTAATTGAAATGAATAATTCGCCTCTG |
| | | CGCGATTTTGTAACTTGGTATTCAAAGCAATCAGGCGAATCCGTTAT |
| | | TGTTTCTCCCGATGTAAAAGGTACTGTTACTGTATATTCATCTGACG |
| | | TTAAACCTGAAAATCTACGCAATTTCTTTATTTCTGTTTTACGTGCA |
| | | AATAATTTTGATATGGTAGGTTCTAACCCTTCCATTATTCAGAAGTA |
| | | TAATCCAAACAATCAGGATTATATTGATGAATTGCCATCATCTGATA |
| | | ATCAGGAATATGATGATAATTCCGCTCCTTCTGGTGGTTTCTTTGTT |
| | | CCGCAAAATGATAATGTTACTCAAACTTTTAAAATTAATAACGTTCG |
| | | GGCAAAGGATTTAATACGAGTTGTCGAATTGTTTGTAAAGTCTAATA |
| | | CTTCTAAATCCTCAAATGTATTATCTATTGACGGCTCTAATCTATTA |
| | | GTTGTTAGTGCTCCTAAAGATATTTTAGATAACCTTCCTCAATTCCT |
| | | TTCAACTGTTGATTTGCCAACTGACCAGATATTGATTGAGGGTTTGA |
| | | TATTTGAGGTTCAGCAAGGTGATGCTTTAGATTTTTCATTTGCTGCT |
| | | GGCTCTCAGCGTGGCACTGTTGCAGGCGGTGTTAATACTGACCGCCTC |
| | | ACCTCTGTTTTATCTTCTGCTGGTGGTTCGTTCGGTATTTTTAATGGC |
| | | GATGTTTTAGGGCTATCAGTTCGCGCATTAAAGACTAATAGCCATTC |
| | | AAAAATATTGTCTGTGCCACGTATTCTTACGCTTTCAGGTCAGAAGG |
| | | GTTCTATCTCTGTTGGCCAGAATGTCCCTTTTATTACTGGTCGTGTGA |
| | | CTGGTGAATCTGCCAATGTAAATAATCCATTTCAGACGATTGAGCGT |
| | | CAAAATGTAGGTATTTCCATGAGCGTTTTTCCTGTTGCAATGGCTGG |
| | | CGGTAATATTGTTCTGGATATTACCAGCAAGGCCGATAGTTTGAGTT |
| | | CTTCTACTCAGGCAAGTGATGTTATTACTAATCAAAGAAGTATTGCT |

TABLE 1-continued

Sequences of all strands required to form barrel with internal tether "a*b*," and signal sequence "dcb." This design requires an annealing program of approximately 72 hours, for example beginning with 3 minutes at 90 C., cooling at rates of 1 degree per 5-10 minutes to 60 C., then cooling at 1 degree per hour to room temperature. Annealing occurs at, for example, 12.5 mM MgCl2 concentrations in TE buffer.

| SEQ ID NO: | name | sequence |
|---|---|---|
| | | ACAACGGTTAATTTGCGTGATGGACAGACTCTTTTACTCGGTGGCCT CACTGATTATAAAAACACTTCTCAGGATTCTGGCGTACCGTTCCTGTC TAAAATCCCTTTAATCGGCCTCCTGTTTAGCTCCCGCTCTGATTCTAA CGAGGAAAGCACGTTATACGTGCTCGTCAAAGCAACCATAGTACGCG CCCTGTAGCGGCGCATTAAGCGCGGCGGGTGTGGTGGTTACGCGCAG CGTGACCGCTACACTTGCCAGCGCCCTAGCGCCCGCTCCTTTCGCTTT CTTCCCTTCCTTTCTCGCCACGTTCGCCGGCTTTCCCCGTCAAGCTCT AAATCGGGGGCTCCCTTTAGGGTTCCGATTTAGTGCTTTACGGCACCT CGACCCCAAAAAACTTGATTTGGGTGATGGTTCACGTAGTGGGCCAT CGCCCTGATAGACGGTTTTTCGCCCTTTGACGTTGGAGTCCACGTTCT TTAATAGTGGACTCTTGTTCCAAACTGGAACAACACTCAACCCTATC TCGGGCTATTCTTTTGATTTATAAGGGATTTTGCCGATTTCGGAACC ACCATCAAACAGGATTTTCGCCTGCTGGGCAAACCAGCGTGGACCG CTTGCTGCAACTCTCTCAGGGCCAGGCGGTGAAGGGCAATCAGCTGT TGCCCGTCTCACTGGTGAAAAGAAAAACCACCCTGGCGCCCAATACGC AAACCGCCTCTCCCCGCGCGTTGGCCGATTCATTAATGCAGCTGGCAC GACAGGTTTCCCGACTGGAAAGCGGGCAGTGAGCGCAACGCAATTAA TGTGAGTTAGCTCACTCATTAGGCACCCCAGGCTTTACACTTTATGCT TCCGGCTCGTATGTTGTGTGGAATTGTGAGCGGATAACAATTTCACA CAGGAAACAGCTATGACCATGATTAC |

Example 2. A Sealed Container with Lid and Lock, Containing Key to Alternate Container FIG. 14 contains images of an example sealed container with lid. This structure was also designed with the caDNAno software, and all double-stranded sequences in this design are arranged in a parallel fashion (though this is not necessary to the function). The lid is locked, with a key strand to another lock tethered to the interior surface of the lid, such that it is shown conditionally.

TABLE 2

Figure 14:
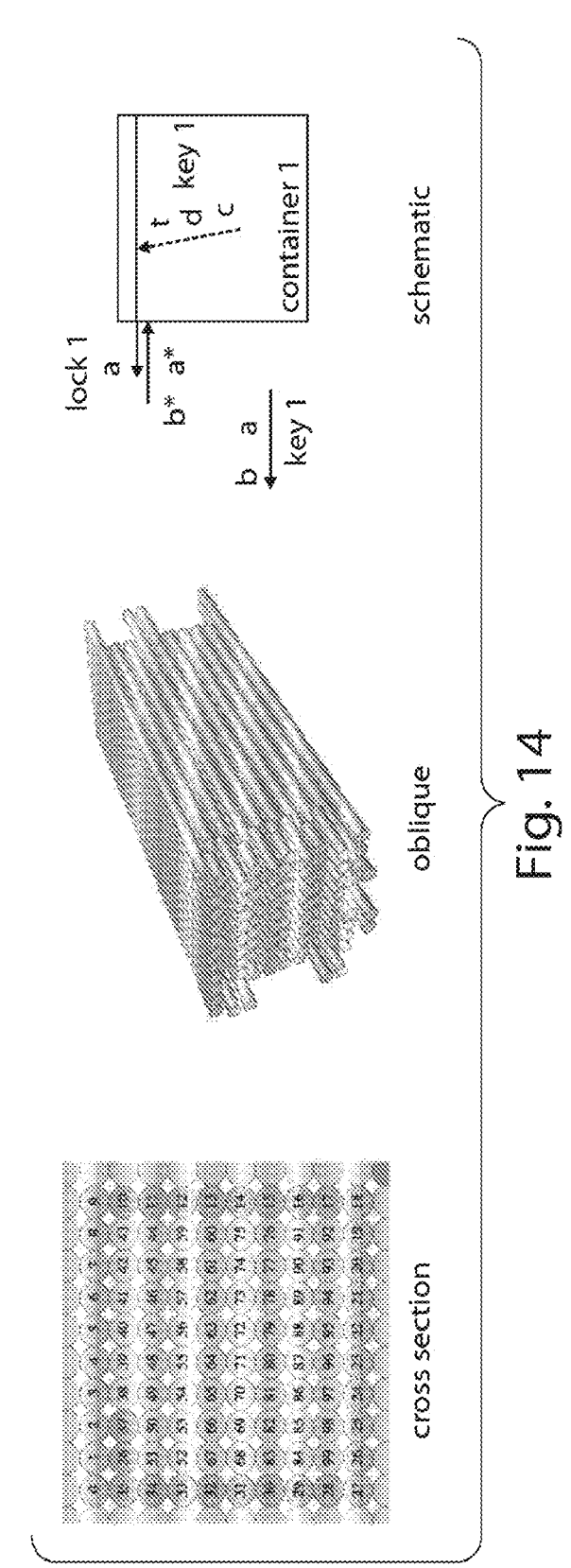
FIG. 14: Screenshots of the caDNAno software files for an example sealed container with lid. The corresponding sequences are listed in Table 2.

Sequences for all strands required to form the sealed container with lid shown in FIG. 14. Also listed are the sequences for the lock mechanism and keys. The long (scaffold) sequence is the same as that listed in Table 1. *Note that the naming convention is for this Example, and these oligonucleotides are not the same as those in Example 1 referred to by the same name.

| SEQ ID NO: | name* | sequence |
|---|---|---|
| SEQ ID NO: 152. | oligo1 | GCGCGTAAAGCCCCCGATTTAGAGCTTGACGGGGAAAGCCGCTGGCAA |
| SEQ ID NO: 153. | oligo2 | CCAGCGCACCGGTGCCCCCTGCATTTCGCACTCAATCCGCGGTCATTG |
| SEQ ID NO: 154. | oligo3 | TGTGGTGCATCAGATGCCGGGTTAATGAGCCG |
| SEQ ID NO: 155. | oligo4 | GTGAGCCTCCTCACAGTTGAGGATGTGCACTC |
| SEQ ID NO: 156. | oligo5 | GTGTAGCGGCTTAATGCGCCGCTAAGAATCAGAGCGGGAGCAGGAACG |
| SEQ ID NO: 157. | oligo6 | TCCTCGTTCAGGGCGCGTACTATGGAGCGGGCGCTAGGGCGGCGAACG |
| SEQ ID NO: 158. | oligo7 | GAGGCCGACCACCACACCCGCCGCGTCACGCT |
| SEQ ID NO: 159. | oligo8 | GGTCACTGAGCTTACGGCTGGAGGAACGTGCCGGACTTGTTGATTGCC |
| SEQ ID NO: 160. | oligo9 | TTAACGGCTGCGGCCAGAATGCGGTCGCGTCC |
| SEQ ID NO: 161. | oligo10 | CATAACGGTGTCCAGCATCAGCGGCGGGCGCGGTTGCGGTCCTGCAGC |
| SEQ ID NO: 162. | oligo11 | AGCGTGGTGCCATCCCACGCAACCTTGCCCTGCGGCTGGTGCAAATCG |
| SEQ ID NO: 163. | oligo12 | GTACGCCACCATCACGCAAATTAAACATCACTTGCCTGAGCAGCCATT |
| SEQ ID NO: 164. | oligo13 | CAGGCGCTCAGCCTCCGGCCAGAGTTCGTCTC |
| SEQ ID NO: 165. | oligo14 | CTCAAACTGAGTAAAAGAGTCTGTGAATCCTGAGAAGTGTACGTGCTT |

TABLE 2-continued

Sequences for all strands required to form the sealed
container with lid shown in FIG. 14. Also listed are the
sequences for the lock mechanism and keys. The long (scaffold) sequence is the same as that listed in Table 1.
*Note that the naming convention is for this Example, and
these oligonucleotides are not the same as those in
Example 1 referred to by the same name.

| SEQ ID NO: | name* | sequence |
|---|---|---|
| SEQ ID NO: 166. | oligo15 | GTCGCTGGAACAGCGGATCAAACTTGGTGAAGGGATAGCT |
| SEQ ID NO: 167. | oligo16 | GTTCCGGCTGCCGCCAGCAGTTGGTCCCGGAATTTGTGAGTAAAACGA |
| SEQ ID NO: 168. | oligo17 | GCAACAGGAAAAAAGAGACGCAGATCTTTGATTAGTAATACCG |
| SEQ ID NO: 169. | oligo18 | CTCACGGAAAACGCTCATGGAAATACCTACATCACGACCA |
| SEQ ID NO: 170. | oligo19 | TTTCTCCGTAAATTTCTGCTCATTAAACGCGGTCCGTTTTCACATCCT |
| SEQ ID NO: 171. | oligo20 | TTTACCAGGCGGTTGTGTACATCGTAAAGTTAAACGATGCAGAACGTC |
| SEQ ID NO: 172. | oligo21 | ACCAGTCATTTGACGCTCAATCGTAGAACAATATTACCGCTAGAAGAA |
| SEQ ID NO: 173. | oligo22 | TCTGTAAATCGTCGCTTGAATTTATCAAATC |
| SEQ ID NO: 174. | oligo23 | AGGGTTTTCCCAGTCACGACGTTGAGATAGAC |
| SEQ ID NO: 175. | oligo24 | CGGCCAGTGCCAAGCTTTCAGAGGGCGCCATG |
| SEQ ID NO: 176. | oligo25 | GATAGAACCCTTCTGATTTAATGCAAATTATT |
| SEQ ID NO: 177. | oligo26 | GATGTGCTGCAAGGCGATTAATCGCACTCCAGCCAGCATCGGCCT |
| SEQ ID NO: 178. | oligo27 | CGCTATTACGCCAGCTTGGTGCCGGAAACCAGTGCATCTG |
| SEQ ID NO: 179. | oligo28 | CTGTTGGGAAGGGCGACATTCAGG |
| SEQ ID NO: 180. | oligo29 | GCGAACTGAACGAACCACCAGCAGACACCGCCATACATAA |
| SEQ ID NO: 181. | oligo30 | ACAGAGGTTGAATGGCTATTAGTCCCTGAAAGAAAGTAAT |
| SEQ ID NO: 182. | oligo31 | AAATACCGATAGCCCTAAAACATCCATTCTGGCCAACAGA |
| SEQ ID NO: 183. | oligo32 | CAGGAAGAATCAAAATAATTCGCAACCAATAGGAACGCCACTAGCAT |
| SEQ ID NO: 184. | oligo33 | CCAGTTTGGCCAGCTTTCATCAACCATTAAAT |
| SEQ ID NO: 185. | oligo34 | CGTAACCGGCAAAGCGCCATTCGCTCGGTGCGGGCCTCTT |
| SEQ ID NO: 186. | oligo35 | GAGGCGGTCAGTATTAAAGATAAAGTAGAAACTCTGTCCAGACGA |
| SEQ ID NO: 187. | oligo36 | TGCAACAGTCTAAAGCATCACCTTATCTGGTCCAAAGTTA |
| SEQ ID NO: 188. | oligo37 | TTTTGTTATAATCAGAAAAGCCCCCCTGAGAG |
| SEQ ID NO: 189. | oligo38 | GTACCGAGCTCGAATTCCCTAAAGGGCAGACGAT |
| SEQ ID NO: 190. | oligo39 | AGTTGGCATCTAAAATATCTTTAGTAGAAGTA |
| SEQ ID NO: 191. | oligo40 | GTTGAAAGAGCAGCAAATGAAAAATGCCACGCTGAGAGCCGCCATTAA |
| SEQ ID NO: 192. | oligo41 | GTCAATCAGAACGGTAATCGTAAAGCCGGAGACAGTCAAACAAAAGGG |
| SEQ ID NO: 193. | oligo42 | GAAGATTGATTTTGTTAAAATTCGATTAAATGTGAGCGAGGGCGCAT |
| SEQ ID NO: 194. | oligo43 | ACAACTAACAAACCCTCAATCAATGCTGAACCTAAGAACGCAATCAAT |
| SEQ ID NO: 195. | oligo44 | GAATCGATTATGTACCCCGGTTGAAATCAGCTCATTTTTGTCTGGCC |
| SEQ ID NO: 196. | oligo45 | TCTGGAGCATTCAACCGTTCTAGCTGCAATGCCTGAGTAAT |
| SEQ ID NO: 197. | oligo46 | TTGAGAGATCTACAAAGAGAGGGT |
| SEQ ID NO: 198. | oligo47 | AATACATTTGAGGATTGAGCACTAGAATCTTACGAGGCGTTTTAG |
| SEQ ID NO: 199. | oligo48 | TTAGACTTTTGCCCGAACGTTATTAATTTTAAAAGTT |
| SEQ ID NO: 200. | oligo49 | ATTCGACAGAATTGAGGAAGGTTAAATCAACA |

TABLE 2-continued

Sequences for all strands required to form the sealed
container with lid shown in FIG. 14. Also listed are the
sequences for the lock mechanism and keys. The long (scaffold) sequence is the same as that listed in Table 1.
*Note that the naming convention is for this Example, and
these oligonucleotides are not the same as those in
Example 1 referred to by the same name.

| SEQ ID NO: | name* | sequence |
|---|---|---|
| SEQ ID NO: 201. | oligo50 | TAATGCCGGGCTATCAGGTCATTGAAAAACAG |
| SEQ ID NO: 202. | oligo51 | TGAGAAAGACTCGTATCAGAAGGAGCGGGCAAGGCAAAGA |
| SEQ ID NO: 203. | oligo52 | AGGCCGGATTAACAACGCCAACATTTGAGAAT |
| SEQ ID NO: 204. | oligo53 | TGAGTAACATTATCCAACGCTAAAACAGGTAAATCCT |
| SEQ ID NO: 205. | oligo54 | ATTAGCAATAAAGATTTCACCATCAATATGATAAACAAGA |
| SEQ ID NO: 206. | oligo55 | TGTACCAAGGGCGCGAGCTGAAAACAAATGGTCAATAACCTGTAGCTC |
| SEQ ID NO: 207. | oligo56 | GATTATCAGGAACAAAGAAACCACTAAATCCTTACAAACA |
| SEQ ID NO: 208. | oligo57 | ATACAGAATTATCATCAAGGGTTAGAAGATTC |
| SEQ ID NO: 209. | oligo58 | AGTAGCATGTAGATTTAGTTTGACAGTACGGTGTCTGGAACTTTAATT |
| SEQ ID NO: 210. | oligo59 | CAATTCTACTCAGAGCATAAAGCTATTTTAAATGATAAAT |
| SEQ ID NO: 211. | oligo60 | TAATCCTGATTGTATAACATAAAAATAGCCTGCTACA |
| SEQ ID NO: 212. | oligo61 | CCAATTCTGCGAACGATAACATCCAATAAATC |
| SEQ ID NO: 213. | oligo62 | CAGTTCCTACCATATCAGAAACAATAACAGGT |
| SEQ ID NO: 214. | oligo63 | AACATGTTTTGCGGATGGCTTAGACCCGAAAGACTTCAAACATAAATC |
| SEQ ID NO: 215. | oligo64 | ACATCGGGAAAATTATTTGCACGTTACTTCTGAATAATGGATATTCCT |
| SEQ ID NO: 216. | oligo65 | CAGGATTAGAGAGTACGTTTCATTCCATATAA |
| SEQ ID NO: 217. | oligo66 | GCTCCTTTGAGCTTCAAAGCGAACATGCTTTAAACAGTTCGACTGGAT |
| SEQ ID NO: 218. | oligo67 | GGTCATTTTTAAATATGCAACTAACATTAGATACATTTCGGGTGGCAT |
| SEQ ID NO: 219. | oligo68 | TCCAACGGATTCGCCTTGATGAAACAATATTC |
| SEQ ID NO: 220. | oligo69 | GCGAATTATTCATATCCAAATAGTTA |
| SEQ ID NO: 221. | oligo70 | ATTGAATCCCCCTCAACAGACCGGAAGCAAAC |
| SEQ ID NO: 222. | oligo71 | AAAAATCATTTTGCCAGAGGGGGTATAAAAACAGTTGAGA |
| SEQ ID NO: 223. | oligo72 | AATTACATCCTGAGCAAAAGAAGAGATTGCTTTGAATACCTACCTTTT |
| SEQ ID NO: 224. | oligo73 | ATAAAACATCAAGAAATGAGTGAATAACCACG |
| SEQ ID NO: 225. | oligo74 | AGCGTCCAACACTATCTGCAGATACATAACGCTCATTATA |
| SEQ ID NO: 226. | oligo75 | AATGTTTAAGAAAACGAGAATGACTATCGCGTTTTAATTCTGATAAGA |
| SEQ ID NO: 227. | oligo76 | TTCCTGTAAGGGGACGACGACAGTTTTCCGGCACCGCTTCGGCGAAAG |
| SEQ ID NO: 228. | oligo77 | AGGCATAGTAAGAGCAATACTGCGGAATCGTC |
| SEQ ID NO: 229. | oligo78 | TCAACTAAATAACCCTCGTTTACCAGACGACGAATAGTAA |
| SEQ ID NO: 230. | oligo79 | TTTAGGAAATCTACGTTAATAAAAATTGGGCT |
| SEQ ID NO: 231. | oligo80 | GATTCATCCAAAATAGCGAGAGGCTTT |
| SEQ ID NO: 232. | oligo81 | TTACAGGTAGAAAGTGCCTTGAAAAGAAGGGTCTTTA |
| SEQ ID NO: 233. | oligo82 | ATAGGTAAGAACTGGCCAAAAGGAATTTTGCT |
| SEQ ID NO: 234. | oligo83 | CCAGTCAGATCATTGTGAATTACCTCAAGAGTAATCTTGACGGTGTAC |
| SEQ ID NO: 235. | oligo84 | GAGACTACCTTTTTAATCGCAAGACAAAGAAC |

TABLE 2-continued

Sequences for all strands required to form the sealed container with lid shown in FIG. 14. Also listed are the sequences for the lock mechanism and keys. The long (scaffold) sequence is the same as that listed in Table 1.
*Note that the naming convention is for this Example, and these oligonucleotides are not the same as those in Example 1 referred to by the same name.

| SEQ ID NO: | name* | sequence |
|---|---|---|
| SEQ ID NO: 236. | oligo85 | TGAGATGGATTACCCAAATCAACGGAACTGACCAACTTTGGACCTGCT |
| SEQ ID NO: 237. | oligo86 | GCGAGGCTGACCTTCATTATGCGATTTTCTGA |
| SEQ ID NO: 238. | oligo87 | GGATATTCTTTAATTTCAACTTTAGACGTTGGGAAGAAAATACCACAT |
| SEQ ID NO: 239. | oligo88 | TTTTTCAAATATATTTATAAATAAGGCGTTAA |
| SEQ ID NO: 240. | oligo89 | AGACCAGGATCATCGCCTGATAAATTATACCA |
| SEQ ID NO: 241. | oligo90 | AGGGAACCTAACAAAGCTGCTCATCCAGAACGTCTTAGCCCGG |
| SEQ ID NO: 242. | oligo91 | ATAAGCGGAGATTTGTCGCATAGGCTGAAAAC |
| SEQ ID NO: 243. | oligo92 | AAATCCGCAAAGAGGACAGATGAACAAGAACC |
| SEQ ID NO: 244. | oligo93 | CCATGTTAACACTAAAACACTCATGTAAAATACGAAAGAC |
| SEQ ID NO: 245. | oligo94 | CTTAGCCGGAACGAGGCAATCATAGAGCCTGTAGC |
| SEQ ID NO: 246. | oligo95 | ACACCGGAATCATAATGGGCTTAAGTAATTTA |
| SEQ ID NO: 247. | oligo96 | AGCGCGAAGACTTTTTGCTACAGAGGCTTTGAAACGTCACCAATGAAA |
| SEQ ID NO: 248. | oligo97 | CGCCATATGGACTAAAACAAAGTACAAAATAA |
| SEQ ID NO: 249. | oligo98 | CAAACTACAACGCCGGAGTTTCGAGGATTAAAGCCAGAATGG |
| SEQ ID NO: 250. | oligo99 | GGCAGAGGCCAGTAGCACCATTACCATTAGCA |
| SEQ ID NO: 251. | oligo100 | AGCATCGGCGTAATCAGTAGCGACAGAATCAA |
| SEQ ID NO: 252. | oligo101 | CTCAGCAGCGTAATGCCACTACGAAGGCACCAAAAGAGGCCGGTTCACG |
| SEQ ID NO: 253. | oligo102 | TTGCGGGACCGATATAAATTTGCCATCTTTTCATA |
| SEQ ID NO: 254. | oligo103 | CAAAATCACATTTTCGAGTTTATTAAAGCCTGAAATACCG |
| SEQ ID NO: 255. | oligo104 | ATTTTCAGGGATAGCTCAGAGCCTTTTCACA |
| SEQ ID NO: 256. | oligo105 | CCATCGATAGCAGCACAACGAGGGTAGCAACGCATGAG |
| SEQ ID NO: 257. | oligo106 | GTTTGCCTTCGTCACCAAAATCACAAAAGAAT |
| SEQ ID NO: 258. | oligo107 | CGCCCACGCATAACGACAATGAAATTATTCCCCCGGCTCC |
| SEQ ID NO: 259. | oligo108 | TACCGATAGTTGCGCTTTCTTAAAGGCATAGTCGGTAGC |
| SEQ ID NO: 260. | oligo109 | ATTATCACTTGAGCCACAGCGCCAAAGACAAA |
| SEQ ID NO: 261. | oligo110 | TGCTTTCGAGGTGAAGCATCGGTTTATCAG |
| SEQ ID NO: 262. | oligo111 | ATTGTATTTCTGCGCAATCACGTTGGTGTAGATTAACAACCACCGCCAC |
| SEQ ID NO: 263. | oligo112 | CGACAAGGTAAATAGGAAGGTGACAATGA |
| SEQ ID NO: 264. | oligo113 | CAACATGGTTTACTTTGTACCATAAAGGGAAT |
| SEQ ID NO: 265. | oligo114 | AGCTAATGCAGAAAGCAGAAT |
| SEQ ID NO: 266. | oligo115 | AAGTCCTGAGCCAGTAGTATAAAGCCAACGCTCAACAGTATACTAGAA |
| SEQ ID NO: 267. | oligo116 | AATAATAATTTTAACCAACTAAAGGAATTG |
| SEQ ID NO: 268. | oligo117 | AGCGCTAATTAGGTTGTGAGAAGAGTCAATAGATTAATTA |
| SEQ ID NO: 269. | oligo118 | TGCTAAACAACTTTCTTTTCTGTGTAAGAGC |
| SEQ ID NO: 270. | oligo119 | TTACGCATGGGAGGGAATAAA |

TABLE 2-continued

Sequences for all strands required to form the sealed container with lid shown in FIG. 14. Also listed are the sequences for the lock mechanism and keys. The long (scaffold) sequence is the same as that listed in Table 1.
*Note that the naming convention is for this Example, and these oligonucleotides are not the same as those in Example 1 referred to by the same name.

| SEQ ID NO: | name* | sequence |
|---|---|---|
| SEQ ID NO: 271. | oligo120 | CGTTAGTAAATGAACTCTGTCGTCTTTC |
| SEQ ID NO: 272. | oligo121 | TAAAGTTTAGACGTCGGATAATTGTAAACGTTAATTATAAGCA |
| SEQ ID NO: 273. | oligo122 | GCTGTCTTTCCTTCAAAGCAT |
| SEQ ID NO: 274. | oligo123 | CAGAGCCACCACCCTCACGATC |
| SEQ ID NO: 275. | oligo124 | TTAAACCAAGTACGAACTAATCCATCACGAATTCATATGTTC |
| SEQ ID NO: 276. | oligo125 | TACCGCGCCCAATAACAAGAAATGGTTTGTTTAGTATC |
| SEQ ID NO: 277. | oligo126 | AAAGAACTTTCATCTTGCTGATGCAAATCCAACCTCCGGC |
| SEQ ID NO: 278. | oligo127 | CCCAGAACAATAAGAGGCGGG |
| SEQ ID NO: 279. | oligo128 | AATCAGAATCGTAGGAATCAT |
| SEQ ID NO: 280. | oligo129 | ATGTACCGTAACACTAAGCCCAAGTAATAAA |
| SEQ ID NO: 281. | oligo130 | CAAGAGAAGGATTAGGAGAGGCTGAGACTCCT |
| SEQ ID NO: 282. | oligo131 | AGAAGGCACATCGAGACGTTTTTATTTGATTAAGACTCCTTAT |
| SEQ ID NO: 283. | oligo132 | TCCGGAACCCAAGAACGGGTA |
| SEQ ID NO: 284. | oligo133 | CAGAACCGCCACCCGGCCAGAAACCCTCTTAATATTTA |
| SEQ ID NO: 285. | oligo134 | CGAACTAAGCAGAGGATATTC |
| SEQ ID NO: 286. | oligo135 | AGGTTCACAAGAAACGGATAT |
| SEQ ID NO: 287. | oligo136 | GCCTTAAATCAAGAGCAAGCAATGTAAATCTGACCTAAAT |
| SEQ ID NO: 288. | oligo137 | TCGGAGGAAGCTATTTTAAAAATTTTTAGAACCCTCATATAAATCGGT |
| SEQ ID NO: 289. | oligo138 | AAAGCGCAGTCAGTAGTAACGAACTAACGGAACAACATTA |
| SEQ ID NO: 290. | oligo139 | TTGATATAAGTAGAAAAGTGCCGTCGAGAG |
| SEQ ID NO: 291. | oligo140 | CTATTGGGAGATAACCTTGAA |
| SEQ ID NO: 292. | oligo141 | CAGTACCAGGCGGATATTAGCGGGGTTTTG |
| SEQ ID NO: 293. | oligo142 | CAGAGAGATTGGATTAAAAACAGAAATAAAGAGAATATACCAAAAATG |
| SEQ ID NO: 294. | oligo143 | AATAAAGTTATAATGCTGTTTAGCTAT |
| SEQ ID NO: 295. | oligo144 | ATTTTCTGAAGAAAAGCAAGAAACAATGAAATAGCAATAGCTA |
| SEQ ID NO: 296. | oligo145 | AACATGAAAGTATTAACAACCTATTATTCT |
| SEQ ID NO: 297. | oligo146 | TTAGACGGCATTTTGCGATGATGGCAATTCAT |
| SEQ ID NO: 298. | oligo147 | CAAAATAAACAGCATTAGTTGTAAGACGCGGTTATATAAC |
| SEQ ID NO: 299. | oligo148 | GTGTACTGTTCATTTGAAACATTA |
| SEQ ID NO: 300. | oligo149 | AACGGGCCAGAGGAAGGCTTAATTGCT |
| SEQ ID NO: 301. | oligo150 | TTGCCAAGAAACGAGATTGCA |
| SEQ ID NO: 302. | oligo151 | TTTAACGTAGTAACAGAAGTTACAAAATCGCGCAGAG |
| SEQ ID NO: 303. | oligo152 | TTATCCCATTCAATTATTAACAATTTCATTTGAATTA |
| SEQ ID NO: 304. | oligo153 | CATATTATATTTTCCCAAACAGTACATAAATCAATATATGACAAAATT |
| SEQ ID NO: 305. | oligo154 | GAGAATAGAAAGGAAAACAGTTTCTCCCAGA |

TABLE 2-continued

Sequences for all strands required to form the sealed container with lid shown in FIG. 14. Also listed are the sequences for the lock mechanism and keys. The long (scaffold) sequence is the same as that listed in Table 1. *Note that the naming convention is for this Example, and these oligonucleotides are not the same as those in Example 1 referred to by the same name.

| SEQ ID NO: | name* | sequence |
|---|---|---|
| SEQ ID NO: 306. | oligo155 | GTAATAAAAGGGAGTTGGGTAACGCC |
| SEQ ID NO: 307. | key "ab" | CCTTCTAACCTCCCTCTCTACTATCTA |
| SEQ ID NO: 308. | lock seq 1 | CAGCGGTGGTGTCACTGCGCGCCTCCCCGGCCTTCTAACCTCCCTCTCTA |
| SEQ ID NO: 309. | lock seq 2 | TAGATAGTAGAGAGGGAGGTTAGAAGGGAAGTTTCCATTAAACGGCTTT GACCCCCAGCGATTGTGTCG |
| SEQ ID NO: 310. | key "cd" | ACCACACACAACCTCCACAAAACCCAAtttttttttttTTGTAGCAATACTTTAAA GGGATTTTAGACTAAACAG |

Example 3. A Tile Structure with Tethered Signal Strand

Figure 15:
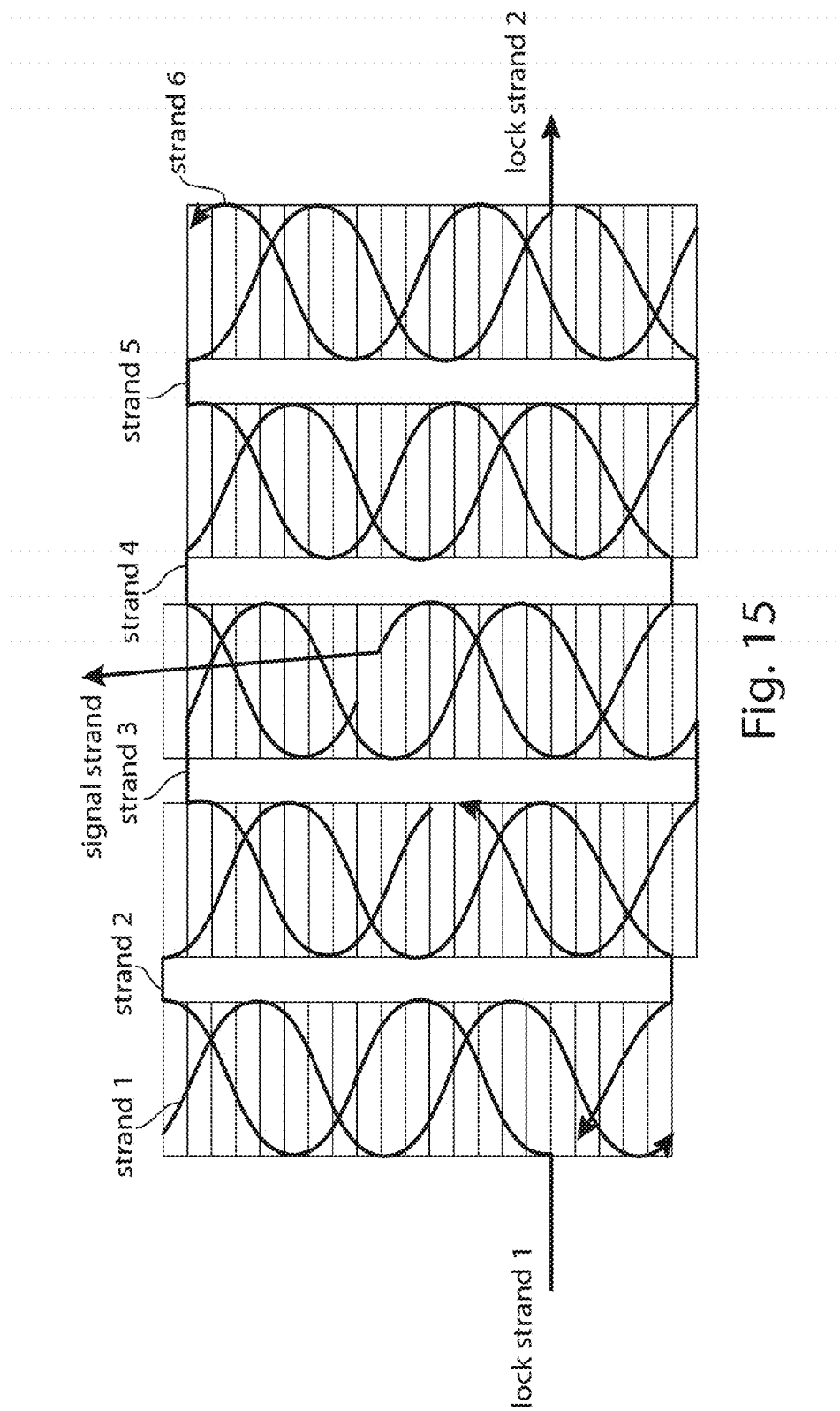
FIG. 15: Schematic of example tile-based sequestering scheme. Six strands are used in this example, with sequences enumerated in Table 3. The 3' end of strand 4 is the output signal strand, covered while the tile is held shut by lock sequences in strands 2 and 5. The structure has a natural "kink" about the strand 3:4 double helix, which constitutes the "hinge" in FIG. 6, and is flexible enough to open or close. Many other tile structures are possible.

FIG. 15 shows the double helical arrangement of an example tile structure with sequestered signal strand. Table 3 lists the sequences.

TABLE 3

Sequences of the six strands forming the tile structure of FIG. 15.

| SEQ ID NO: | name | sequence |
|---|---|---|
| SEQ ID NO: 311 | strand 1 | CAAGACTCGACTAGTGCGAGTC |
| SEQ ID NO: 312 | strand 2 | CTATCT TAACCTCCCTCTCTAGCACTAGTCGAGTCTTGAGAGCTCG TAGCTAGTGTAAGC GACTC |
| SEQ ID NO: 313 | strand 3 | GCTACGAGCTC CTATGTCTCGAATGCTAGCAGC AGCTTACACTA |
| SEQ ID NO: 314 | strand 4 | AGACATAGCTAGACTACTGACGTACATCGCTCTAGCATTCAGTTA ACCCACGCCGAATCCTAGACT |
| SEQ ID NO: 315 | strand 5 | GATCAGGCGATGTACGTCAGTAGTCTAG GACGTCGTCTAGAACTT AGAGAGGGAGGTTA |
| SEQ ID NO: 316 | strand 6 | CTGATCAGTTCTAGACGACGTC |
| SEQ ID NO: 317 | key | TAGAGAGGGAGGTTA AGATAG |

REFERENCES

1. Seeman, N. C. An Overview of Structural DNA Nanotechnology. *Mol Biotechnol* 37, 246-257 (2007).
2. Zhang, D. Y. & Seelig, G. Dynamic DNA nanotechnology using strand-displacement reactions. *Nature Chem* 3, 103-113 (2011).
3. Andersen, E. S. et al. Self-assembly of a nanoscale DNA box with a controllable lid. *Nature* 459, 73-76 (2009).
4. Douglas, S. M. et al. Rapid prototyping of 3D DNA-origami shapes with caDNAno. *Nucleic Acids Res* 37, 5001-5006 (2009).
5. Zadeh, J. N. et al. NUPACK: Analysis and design of nucleic acid systems. *J. Comput. Chem.* n/a-n/a (2010).doi:10.1002/jcc.21596
6. Douglas, S. M. et al. Self-assembly of DNA into nanoscale three-dimensional shapes. *Nature* 459, 414-418 (2009).
7. Rothemund, P. W. K. Folding DNA to create nanoscale shapes and patterns. *Nature* 440, 297-302 (2006).
8. Zhang, D. Y. & Winfree, E. Control of DNA Strand Displacement Kinetics Using Toehold Exchange. *Journal of the American Chemical Society* 131, 17303-17314 (2009).
9. Yin, P., Choi, H. M. T., Calvert, C. R. & Pierce, N. A. Programming biomolecular self-assembly pathways. *Nature* 451, 318-322 (2008).
10. Cho, E. J., Lee, J.-W. & Ellington, A. D. Applications of Aptamers as Sensors. *Annual Review of Analytical Chemistry* 2, 241-264 (2009).

EQUIVALENTS

Those skilled in the art will recognize, or be able to ascertain using no more than routine experimentation, many equivalents of the specific embodiments of the subject matter described herein. Such equivalents are intended to be encompassed by the following claims.

All publications, patents, and patent applications cited in this specification are herein incorporated by reference to the same extent as if each individual publication or patent application was specifically and individually indicated to be incorporated by reference.

What is claimed is:

1. A synthetic system comprising
   (a) a first three-dimensional nucleic acid nanostructure shaped in the form of a container comprising walls, an interior surface and an exterior surface,
   (b) a first tethered nucleic acid attached to the interior surface of the first three-dimensional nucleic acid nanostructure and partially hybridized to a first output signal nucleic acid, wherein the first tethered nucleic acid contains a toehold domain that is not complementary to the first output signal nucleic acid,
   (c) a second three-dimensional nucleic acid nanostructure shaped in the form of a container comprising walls, an interior surface and an exterior surface, and
   (d) a second tethered nucleic acid attached to the interior surface of the second three-dimensional nucleic acid nanostructure and partially hybridized to a second output signal nucleic acid, wherein the second tethered nucleic acid contains a toehold domain that is not complementary to the second output signal nucleic acid, and
   wherein the toehold domain of the second tethered nucleic acid is complementary to a domain of the first output signal nucleic acid.

2. The system of claim 1, wherein the first and second tethered nucleic acids are not integral to the first and second nucleic acid nanostructures.

3. The system of claim 1, wherein the first and second nucleic acid nanostructures are independently selected from the group consisting of closed nucleic acid nanostructures and open nucleic acid nanostructures.

4. The system of claim 3, wherein the open nucleic acid nanostructures comprise two open ends.

5. The system of claim 3, wherein the closed nucleic acid nanostructures comprise a nucleic acid lock.

6. The system of claim 1, further comprising one or more upstream and/or downstream nucleic acid nanostructures.

7. The system of claim 6, wherein the one or more of the upstream and/or downstream nucleic acid nanostructures comprise tethered nucleic acid.

8. A method comprising
contacting a first input signal nucleic acid with the system of claim 1 in an amount effective to release the second output signal nucleic acid from the second nucleic acid nanostructure.

9. The system of claim 6, wherein the one or more of the upstream and/or downstream nucleic acid nanostructures comprise free flowing nucleic acids.

10. The system of claim 9, wherein the free flowing nucleic acids are output signal nucleic acids.

11. The system of claim 1, wherein the first nucleic acid nanostructures and/or the second nucleic acid nanostructure comprises an agent.

12. The system of claim 11, wherein the agent is or comprises a therapeutic agent.

13. The system of claim 11, wherein the agent is or comprises a detectable marker.

14. The system of claim 1, wherein the first nucleic acid nanostructures and/or the second nucleic acid nanostructure comprises a plurality of tethered nucleic acids.

15. The system of claim 1, wherein the first nucleic acid nanostructures and/or the second nucleic acid nanostructure comprises a plurality of free flowing nucleic acids.

16. The system of claim 1, wherein the length of the toehold domain of the first tethered nucleic acid is 4-12 nucleotides.

17. The system of claim 1, wherein the length of the toehold domain of the second tethered nucleic acid is 4-12 nucleotides.

18. The system of claim 1, wherein the first nucleic acid nanostructure is a deoxyribonucleic acid (DNA) nanostructure.

19. The system of claim 1, wherein the second nucleic acid nanostructure is a DNA nanostructure.

* * * * *